(12) United States Patent
Yoon et al.

(10) Patent No.: US 10,265,356 B2
(45) Date of Patent: Apr. 23, 2019

(54) **ENTEROINVASIVE *E. COLI* BACTERIOPHAGE ESC-COP-4 AND USE THEREOF FOR INHIBITING PROLIFERATION OF ENTEROINVASIVE *E. COLI***

(71) Applicant: Intron Biotechnology, Inc., Gyeonggi-do (KR)

(72) Inventors: Seong Jun Yoon, Seoul (KR); Sang Hyeon Kang, Seoul (KR); Soo Youn Jun, Seoul (KR); Hyoun Rok Paik, Incheon (KR); Jee Soo Son, Seoul (KR); Byung Kuk Kim, Gyeonggi-do (KR); Hee Jeong Shin, Gyeonggi-do (KR); Dong Min Kang, Incheon (KR)

(73) Assignee: INTRON BIOTECHNOLOGY, INC., Gyeonggi-Do (KR)

( * ) Notice: Subject to any disclaimer, the term of this patent is extended or adjusted under 35 U.S.C. 154(b) by 0 days.

(21) Appl. No.: 15/538,588

(22) PCT Filed: Dec. 28, 2015

(86) PCT No.: PCT/KR2015/014332
§ 371 (c)(1),
(2) Date: Jun. 21, 2017

(87) PCT Pub. No.: WO2016/108542
PCT Pub. Date: Jul. 7, 2016

(65) Prior Publication Data
US 2017/0333499 A1    Nov. 23, 2017

(30) Foreign Application Priority Data
Dec. 30, 2014   (KR) .................. 10-2014-0192984

(51) Int. Cl.
| | | |
|---|---|---|
| *C12N 7/00* | (2006.01) | |
| *C12N 7/02* | (2006.01) | |
| *A61K 35/76* | (2015.01) | |
| *A23L 2/38* | (2006.01) | |
| *A23K 20/195* | (2016.01) | |
| *A23K 10/16* | (2016.01) | |
| *A01N 63/00* | (2006.01) | |
| *C02F 3/34* | (2006.01) | |
| *A23K 10/18* | (2016.01) | |
| *A23K 50/30* | (2016.01) | |
| *A61P 31/04* | (2006.01) | |
| *C02F 103/02* | (2006.01) | |

(52) U.S. Cl.
CPC ............. *A61K 35/76* (2013.01); *A01N 63/00* (2013.01); *A23K 10/16* (2016.05); *A23K 10/18* (2016.05); *A23K 20/195* (2016.05); *A23K 50/30* (2016.05); *A23L 2/38* (2013.01); *A61P 31/04* (2018.01); *C02F 3/34* (2013.01); *C12N 7/00* (2013.01); *C12N 7/02* (2013.01); *A23V 2002/00* (2013.01); *C02F 2103/02* (2013.01); *C02F 2303/04* (2013.01); *C02F 2305/00* (2013.01); *C12N 2795/10121* (2013.01); *C12N 2795/10131* (2013.01); *C12N 2795/10132* (2013.01)

(58) Field of Classification Search
None
See application file for complete search history.

(56) References Cited

U.S. PATENT DOCUMENTS

| | | | |
|---|---|---|---|
| 8,066,990 B2 | 11/2011 | Yoon et al. | |
| 8,071,352 B2 | 12/2011 | Yoon et al. | |
| 9,211,309 B2 | 12/2015 | Yoon et al. | |
| 9,433,653 B2 | 9/2016 | Yoon et al. | |
| 9,540,616 B2 | 1/2017 | Yoon et al. | |
| 9,950,018 B2* | 4/2018 | Shin ..................... | A61K 35/76 |
| 9,951,342 B2 | 4/2018 | Barrangou et al. | |
| 10,028,984 B2* | 7/2018 | Yoon ................... | A23K 20/195 |
| 2010/0015098 A1 | 1/2010 | Bruessow et al. | |
| 2013/0323209 A1 | 12/2013 | Sung et al. | |
| 2014/0017205 A1* | 1/2014 | Shin ..................... | C12N 7/00 424/93.6 |
| 2014/0356330 A1* | 12/2014 | Kim ...................... | A61K 35/76 424/93.6 |
| 2015/0322409 A1* | 11/2015 | Yoon ..................... | C12N 7/00 424/93.6 |
| 2017/0035817 A1* | 2/2017 | Shin ..................... | A23K 20/195 |
| 2017/0037380 A1* | 2/2017 | Shin ..................... | A23K 20/10 |
| 2017/0037382 A1* | 2/2017 | Shin ..................... | A23K 10/18 |
| 2017/0333498 A1* | 11/2017 | Yoon ..................... | A61K 35/76 |
| 2017/0333499 A1* | 11/2017 | Yoon ..................... | A23L 2/38 |
| 2017/0340685 A1 | 11/2017 | Yoon et al. | |
| 2017/0340686 A1* | 11/2017 | Yoon ..................... | A61K 35/76 |
| 2017/0348365 A1* | 12/2017 | Yoon ..................... | A23L 2/38 |
| 2017/0368116 A1* | 12/2017 | Regeimbal ............. | A61K 35/76 |
| 2017/0369852 A1 | 12/2017 | Yoon et al. | |
| 2018/0000125 A1* | 1/2018 | Yoon ..................... | A61K 35/76 |
| 2018/0119109 A1 | 5/2018 | Yoon et al. | |

FOREIGN PATENT DOCUMENTS

| | | |
|---|---|---|
| CN | 201580071157 | 12/2015 |
| CN | 201580071183 | 12/2015 |

(Continued)

OTHER PUBLICATIONS

Easwaran et al, Molecular and Cellular Probes, 2015, 29:151-157, available online Mar. 21, 2015 (Year: 2015).*

(Continued)

*Primary Examiner* — Nita M. Minnifield
(74) *Attorney, Agent, or Firm* — Ballard Spahr LLP

(57) ABSTRACT

The present invention relates to a Myoviridae bacteriophage Esc-COP-4 that is isolated from the nature and can kill specifically enteroinvasive *E. coli* strains, which has a genome represented by the nucleotide sequence of SEQ. ID. NO: 1 (Accession NO: KCTC 12663BP), and a method for preventing and treating the infections of enteroinvasive *E. coli* using the composition comprising said bacteriophage as an active ingredient.

2 Claims, 1 Drawing Sheet
Specification includes a Sequence Listing.

(56) References Cited

FOREIGN PATENT DOCUMENTS

| KR | 20110041670 | | 4/2011 | | |
|---|---|---|---|---|---|
| KR | 20120111535 | | 10/2012 | | |
| KR | 10-2014-0192983 | | 12/2014 | | |
| KR | 10-2014-0192984 | | 12/2014 | | |
| KR | 20140140698 | | 12/2014 | | |
| WO | WO-2013073843 | A1 * | 5/2013 | ............ | A61K 35/76 |
| WO | PCT/KR2015/014331 | | 12/2015 | | |
| WO | PCT/KR2015/014332 | | 12/2015 | | |
| WO | WO-2016108536 | A1 * | 7/2016 | ........... | A23K 20/195 |
| WO | WO-2016108538 | A1 * | 7/2016 | ............ | A61K 35/76 |
| WO | WO-2016108540 | A1 * | 7/2016 | ............ | A23L 2/38 |
| WO | WO-2016108541 | A1 * | 7/2016 | ............ | A61K 35/76 |
| WO | WO-2016108542 | A1 * | 7/2016 | ............... | A23L 2/38 |
| WO | WO-2016114517 | A1 * | 7/2016 | ............ | A61K 35/76 |
| WO | WO-2017111306 | A1 * | 6/2017 | ............ | A61Q 19/10 |
| WO | WO-2018101594 | A1 * | 6/2018 | | |

OTHER PUBLICATIONS

Davis, Enterovirulent *E. coli* Infection Symptoms and Treatment, 18 pages. https://www.medicinenet.com/enterovirulent_e_coli_eec/article.htm#enterovirulent_e_coli_eec_facts (Year: 2018).*

Intermountain Healthcare, Shigella/Enteroinvasive *E. Coli*, Information for Patients, 2 pages, 2018 (Year: 2018).*

O'Reilly et al, Centers for Disease Control and Prevention, Chapter 3: Infectious Diseases Related to Travel. May 31, 2017 https://www.cdc.gov/ (Year: 2017).*

Clements et al Gut Microbes 3:@, 71-87: Mar./Apr. 2012 (Year: 2012).*

Vieira et al, Am. J. Trop. Med. Hyg., 2007, 76/3:528-533 (Year: 2007).*

Mani et al, Vaccine 34, 2016, pp. 2887-2894. available online Mar. 12, 2016 (Year: 2016).*

RightDiagnosis.com. Enteroinvasive *E. coli* Infection Symptoms, Diagnosis, Treatments and Causes, 2014, 4 pages (Year: 2014).*

Gohar et al, BMC Res. Notes, 2016, 9:80, 18 pages. published online Feb. 9, 2016 (Year: 2016).*

Moriel et al, mSphere 1(6):e00326016. 2016 published: Nov. 23, 2016 (Year: 2016).*

Rojas-Lopez et al, Fontiers in Microbiology, Mar. 2018, vol. 9, Article 440, 17 pages. published;Mar. 20, 2018 (Year: 2018).*

Gohar et al, 17th International Congress on Infectious Diseases/International Journal of Infectious Diseases, 45S(2016)p. 419 abstract only. (Year: 2016).*

Bourgeois et al, Vaccine 34(2016), pp. 2880-2886. available online Mar. 15, 2016 (Year: 2016).*

Walker, Vaccine 33 (2015), pp. 954-965. available online Dec. 5, 2014 (Year: 2014).*

Giersing et al, Vaccine 34 (2016), pp. 2865-2869. available online Mar. 15, 2016 (Year: 2016).*

Wenzel et al, Vaccine, 2017, 35:6798-6802. avialable online: Sep. 7, 2017 (Year: 2017).*

Walker, Vaccine, 2015, 33:954-965. available online: Dec. 5, 2014 (Year: 2015).*

Gerdts et al, ILAR Journal, 2015, 56/1:53-62 (Year: 2015).*

Gohar et al, BMC Research Notes, 2016, 9:80, 18 pages. (Year: 2016).*

International Search Report and Written Opinion dated Apr. 25, 2016 by the International Searching Authority for International Application No. PCT/KR2015/014332, which was filed on Dec. 28, 2015 and published as WO 2016/108542 on Jul. 7, 2016 (Applicant—Intron Biotechnology, Inc.) (Original—8 pages//Translation—2 pages).

Boyd, E.F. and Brüssow, H., Common Themes Among Bacteriophage-Encoded Virulence Factors and Diversity Among the Bacteriophages Involved. Trends Microbiol. 2002; 10(11):521-9.

Center for Health Protection. Epidemiology, Prevention and Control of Shiga Toxin-Producing *Escherichia coli* Infection. 2013 (19 pages).

Hoa, N.X., et al., Isolation and Characterization of Two T4-like Bacteriophages Against Pathogenic *Escherichia coli* of Piglet. African J Microbiol Res. 2014; 8(41):3604-11.

Karmali, M.A., Prospects for Preventing Serious Systemic Toxemic Complications for Shiga Toxin-Producing *Escherichia coli* Infections Using Shiga Toxin Receptor Analogues. J Infect Dis. 2004; 189(3):355-9.

Liao, W.-C. et al., T4-like Genome Organization of the *Escherichia coli* O157:H7 Lytic Phage AR1. J Virol. 2011; 85(13):6567-78.

NCBI, GenBank Accession No. JN986846.1, Enterobacteria Phage vB_EcoM_ACG-C40, Complete Genome. 2012 (99 pages).

NCBI, GenBank Accession No. KM606996.1, Enterobacteria Phage RB6, Complete Genome. 2014 (98 pages).

Werber, D. et al., Preventing Household Transmission of Shiga Toxin-Producing *Escherichia coli* O157 Infection: Promptly Separating Siblings Might Be the Key. Clin Infect Dis. 2008; 46(8):1189-96.

Zhu, C. et al., Protection Against Shiga Toxin-Producing *Escherichia coli* Infection by Transcutaneous Immunization with Shiga Toxin Subunit B. Clin Vaccine Immunol. 2008; 15(2):359-66.

International Search Report and Written pinion dated Apr. 25, 2016 by the International Searching Authority for Patent Application No. PCT/KR2015/014331, which was filed on Dec. 28, 2015 and published as WO 2016/108541 on Jul. 7, 2016 (Inventor—Seong Jun Yoon et al.; Applicant—Intron Biotechnology, inc.) (Original—9 pages; Translation—8 pages).

Non-Final Office Action dated May 23, 2018 by the U.S. Patent and Trademark Office for U.S. Appl. No. 15/538,573, filed Jun. 21, 2017 and published as US 2017/0340686 on Nov. 30, 2017 (Inventor—Yoon et al.; Applicant—Intron Biotechnology, Inc.) (10 pages).

U.S. Appl. No. 15/538,573 (2017/0340686) filed Jun. 21, 2017 (Nov. 30, 2017) Seong Jun Yoon (Intron Biotechnol., Inc.).

* cited by examiner

ENTEROINVASIVE *E. COLI* BACTERIOPHAGE ESC-COP-4 AND USE THEREOF FOR INHIBITING PROLIFERATION OF ENTEROINVASIVE *E. COLI*

CROSS-REFERENCE TO RELATED APPLICATIONS

The present application is a U.S. National Phase Application of International Application No. PCT/KR2015/014332, filed Dec. 28, 2015, which claims priority to Korean Application No. 10-2014-0192984, filed Dec. 30, 2014, each of which are hereby incorporated by reference in their entirety.

REFERENCE TO SEQUENCE LISTING

The Sequence Listing submitted Jun. 21, 2017, as a text file named "08162_0033U1_Sequence_Listing.txt," created on May 24, 2017, and having a size of 213,522 bytes is hereby incorporated by reference pursuant to 37 C.F.R. § 1.52(e)(5).

BACKGROUND OF THE INVENTION

1. Field of the Invention

The present invention relates to a bacteriophage isolated from the nature that infects and kills enteroinvasive *E. coli*, and a method for preventing and treating the infections of enteroinvasive *E. coli* using a composition comprising the bacteriophage as an active ingredient. More particularly, the present invention relates to a Myoviridae bacteriophage Esc-COP-4 that is isolated from the nature and can kill specifically enteroinvasive *E. coli* strains, which has a genome represented by the nucleotide sequence of SEQ. ID. NO: 1 (Accession NO: KCTC 12663BP), and a method for preventing the infections of enteroinvasive *E. coli* and thereafter treating them using the composition comprising said bacteriophage as an active ingredient.

2. Description of the Related Art

*Escherichia coli* (*E. coli*) is recognized to have more than 9,000 serotypes according to the combination of surface antigen (lipopolysaccharide, 0), flagella antigen (flagellin, H) and capsular antigen (polysaccharide, K). *E. coli* is also classified etiologically to enterotoxigenic *E. coli* (ETEC), enteroinvasive *E. coli* (EIEC), enteropathogenic *E. coli* (EPEC) and enteroinvasive *E. coli* (EHEC), depending upon pathogenesis, toxins and O:H serotypes. Above all, enteroinvasive *E. coli* (EIEC) enters epithelial cells of large intestine mucosa, thereby makes ulcers by cell necrosis etc. and provokes bacillary dysentery with diarrhea of blood and mucus.

The enteroinvasive *E. coli* is an important pathogenic bacterium causing diarrhea in pigs. It reduces the growth rate of infected pigs, leading to death and leaves a lot of economical losses because it costs high to treat and prevent this infection. Considering a significant damage in livestock industry by such *E. coli*, it is urgently requested to develop a method for preventing and treating enteroinvasive *E. coli* infections. A variety of antibiotics have been used to prevent or treat such enteroinvasive *E. coli* infections. However, according to the recent rise of antibiotic-resistant bacteria, an efficient alternative is urgently requested.

Recently, the use of bacteriophages has drawn our attention as a new way of treating bacterial infections. Particularly, the reason of our high interest in bacteriophages is because bacteriophage-based treatment is a nature-friendly method. Bacteriophages are an extremely small microorganism that infects bacteria, which are called phage in short. Once bacteriophage infects bacteria, the bacteriophage is proliferated in the inside of the bacterial cell. After full proliferation, the progenies destroy the bacterial cell wall to escape from the host, suggesting that the bacteriophage has bacteria killing ability. The bacteriophage infection is characterized by high specificity, so that a certain bacteriophage infects only a specific bacterium. That is, the bacterium that can be infected by certain bacteriophage is limited, suggesting that bacteriophage can kill only a specific bacterium and cannot harm other bacteria.

Bacteriophage was first found out by an English bacteriologist Twort in 1915 when he noticed that *Micrococcus* colonies melted and became transparent by something unknown. In 1917, a French bacteriologist d'Herelle found out that *Shigella disentriae* in the filtrate of dysentery patient feces melted by something, and further studied about this phenomenon. As a result, he identified bacteriophage independently, and named it as bacteriophage which means a bacteria killer. Since then, bacteriophages specifically acting against such pathogenic bacteria as *Shigella, Salmonella Typhi*, and *Vibrio cholerae* have been continuously identified.

Owing to the unique capability of bacteriophage to kill bacteria, bacteriophages have been studied and anticipated as a method to treat bacterial infections. However, after penicillin was found by Fleming, studies on bacteriophages had been only continued in some of Eastern European countries and the former Soviet Union because of the universalization of antibiotics. After the year of 2000, the merit of the conventional antibiotics faded because of the increase of antibiotic-resistant bacteria. So, bacteriophages are once again spotlighted as a new anti-bacterial agent that can replace the conventional antibiotics.

Furthermore, the recent regulation of using antibiotics is fortified by the government world-widely. The interest on bacteriophages is increasing more and also industrial applications are increasily achieved.

Therefore, the present inventors tried to develop a composition applicable for the prevention or treatment of enteroinvasive *E. coli* infections by using a bacteriophage that is isolated from the nature and can kill enteroinvasive *E. coli* selectively, and further to establish a method for preventing or treating the infections of enteroinvasive *E. coli* using the composition. As a result, the present inventors isolated bacteriophages suitable for this purpose and secured the nucleotide sequence of the genome that distinguishes the bacteriophage of the present invention from other bacteriophages. Then, we have developed a composition comprising the isolated bacteriophage as an active ingredient, and confirmed that this composition could be efficiently used for the prevention and treatment of enteroinvasive *E. coli* infections, leading to the completion of the present invention.

SUMMARY OF THE INVENTION

It is an object of the present invention to provide a Myoviridae bacteriophage Esc-COP-4 that is isolated from the nature and can kill enteroinvasive *E. coli* specifically, which has the genome represented by the nucleotide sequence of SEQ. ID. NO: 1 (Accession NO: KCTC 12663BP).

It is another object of the present invention to provide a composition applicable for the prevention of enteroinvasive *E. coli* infections, which comprises the bacteriophage Esc-COP-4 that can infect and kill enteroinvasive *E. coli*, as an active ingredient and a method for preventing the infections of enteroinvasive *E. coli* using said composition.

It is another object of the present invention to provide a composition applicable for the treatment of enteroinvasive *E. coli* infections, which comprises the bacteriophage Esc-COP-4 that can infect and kill enteroinvasive *E. coli*, as an active ingredient and a method for treating the infections of enteroinvasive *E. coli* using said composition.

It is another object of the present invention to provide a disinfectant for preventing and treating the infections of enteroinvasive *E. coli* using said composition.

It is another object of the present invention to provide a drinking water additive for preventing and treating the infections of enteroinvasive *E. coli* using said composition.

It is also an object of the present invention to provide a feed additive effective upon farming by preventing and treating the infections of enteroinvasive *E. coli* using said composition.

To achieve the above objects, the present invention provides a Myoviridae bacteriophage ESC-COP-4 that is isolated from the nature and can kill specifically enteroinvasive *E. coli*, which has the genome represented by the nucleotide sequence of SEQ. ID. NO: 1 (Accession NO: KCTC 12663BP), and a method for preventing and treating the infections of enteroinvasive *E. coli* using a composition comprising the bacteriophage as an active ingredient. The bacteriophage Esc-COP-4 has been isolated by the present inventors and then deposited at Korean Collection for Type Cultures, Korea Research Institute of Bioscience and Biotechnology in Aug. 21, 2014 (Accession NO: KCTC 12663BP).

The present invention also provides a disinfectant, a drinking water additive, and a feed additive applicable for the prevention or treatment of enteroinvasive *E. coli* infections, which comprises the bacteriophage Esc-COP-4 as an active ingredient.

Since the bacteriophage Esc-COP-4 included in the composition of the present invention kills enteroinvasive *E. coli* efficiently, it is regarded as effective to prevent or treat *E. coli* diarrhea (infections) caused by enteroinvasive *E. coli*. Therefore, the composition of the present invention can be utilized for the prevention and treatment of *E. coli* diarrhea caused by enteroinvasive *E. coli*. In this specification, the *E. coli* diarrhea includes symptoms caused by the *E. coli* infections accompanying fever, diarrhea and the like.

In this description, the term "treatment" or "treat" indicates (i) to suppress the diarrhea caused by enteroinvasive *E. coli*; and (ii) to relieve the diarrhea caused by enteroinvasive *E. coli*.

In this description, the term "isolation" or "isolated" indicates all the actions to separate the bacteriophage by using diverse experimental techniques and to secure the characteristics that can distinguish this bacteriophage from others, and further includes the action of proliferating the bacteriophage via bioengineering techniques so as to make it useful.

The pharmaceutically acceptable carrier included in the composition of the present invention is the one that is generally used for the preparation of a pharmaceutical formulation, which is exemplified by lactose, dextrose, sucrose, sorbitol, mannitol, starch, acacia rubber, calcium phosphate, alginate, gelatin, calcium silcate, microcrystalline cellulose, polyvinyl pyrrolidone, cellulose, water, syrup, methylcellulose, methylhydroxybenzoate, propylhydroxybenzoate, talc, magnesium stearate, and mineral oil, but not always limited thereto. The composition of the present invention can additionally include lubricants, wetting agents, sweeteners, flavors, emulsifiers, suspending agents, and preservatives, in addition to the above ingredients.

In the composition of the present invention, the bacteriophage Esc-COP-4 is included as an active ingredient. At this time, the bacteriophage Esc-COP-4 is included at the concentration of $1\times10^1$ pfu/ml~$1\times10^{30}$ pfu/ml or $1\times10^1$ pfu/g~$1\times10^{30}$ pfu/g, and preferably at the concentration of $1\times10^4$ pfu/ml~$1\times10^{15}$ pfu/ml or $1\times10^4$ pfu/g~$1\times10^{15}$ pfu/g.

The composition of the present invention can be formulated by the method that can be performed by those in the art by using a pharmaceutically acceptable carrier and/or excipient in the form of unit dose or in a multi-dose container. The formulation can be in the form of solution, suspension or emulsion in oil or water-soluble medium, extract, powder, granule, tablet or capsule. At this time, a dispersing agent or a stabilizer can be additionally included.

The composition of the present invention can be prepared as a disinfectant, a drinking water additive, or a feed additive according to the purpose of use, but not always limited thereto.

Advantageous Effect

The method for preventing and treating the infections of enteroinvasive *E. coli* using this composition comprising the bacteriophage Esc-COP-4 as an active ingredient, have the advantage of high specificity to enteroinvasive *E. coli*, compared with the conventional methods based on the chemical materials including the conventional antibiotics. That means, the composition of the present invention can be used for preventing or treating the infections of enteroinvasive *E. coli* specifically without affecting other useful residential bacteria, and accordingly has fewer side effects. In general, when chemical materials such as antibiotics are used, the general residential bacteria are also damaged to weaken immunity in animals with carrying various side effects. In the meantime, the composition of the present invention uses the bacteriophage isolated from the nature as an active ingredient, so that it is very nature-friendly.

BRIEF DESCRIPTION OF THE DRAWINGS

The application of the preferred embodiments of the present invention is best understood with reference to the accompanying drawings, wherein.

DESCRIPTION OF THE PREFERRED EMBODIMENTS

Practical and presently preferred embodiments of the present invention are illustrative as shown in the following Examples.

However, it will be appreciated that those skilled in the art, on consideration of this disclosure, may make modifications and improvements within the spirit and scope of the present invention.

Example 1: Isolation of Bacteriophage Capable of Killing Enteroinvasive E. coli Samples were collected from the nature to screen the bacteriophage capable of killing enteroinvasive E. coli. The enteroinvasive E. coli used for the bacteriophage isolation herein were the one that had been isolated by the present inventors and identified as enteroinvasive E. coli previously.

The isolation procedure of the bacteriophage is described in detail hereinafter. The collected sample was added to the TSB (Tryptic Soy Broth) medium (pancreatic digest of casein, 17 g/L; papaic digest of soybean, 3 g/L; dextrose, 2.5 g/L; sodium chloride, 5 g/L; dipotassium phosphate, 2.5 g/L) inoculated with enteroinvasive E. coli at the ratio of 1/1000, followed by shaking culture at 37° C. for 3~4 hours. Upon completion of the culture, centrifugation was performed at 8,000 rpm for 20 minutes and supernatant was recovered. The recovered supernatant was inoculated with enteroinvasive E. coli at the ratio of 1/1000, followed by shaking culture at 37° C. for 3~4 hours. When the sample contained the bacteriophage, the above procedure was repeated total 5 times in order to increase the titer of the bacteriophage. After repeating the procedure 5 times, the culture solution proceeded to centrifugation at 8,000 rpm for minutes and the resulting supernatant was recovered. The recovered supernatant was filtrated by using a 0.45 μm filter. The obtained filtrate was used in spot assay for examining whether or not the bacteriophage capable of killing enteroinvasive E. coli was included therein.

Spot assay was performed as follows; TSB medium was inoculated with enteroinvasive E. coli at the ratio of 1/1000, followed by shaking culture at 37° C. for overnight. 3 ml (1.5 of $OD_{600}$) of the culture broth of enteroinvasive E. coli prepared above was spread on the TSA (Tryptic Soy Agar; pancreatic digest of casein, 17 g/L; papaic digest of soybean, 3 g/L; sodium chloride, 5 g/L; agar, 15 g/L) plate. The plate stood in a chamber for about 30 minutes to dry. After drying, 10 μl of the resulting filtrate was spotted directly onto the surface of the enteroinvasive E. coli lawns and dried for about 30 minutes. Following drying, the plate was incubated at 37° C. for a day and then, examined for the formation of clear zones on the surface of the bacterial lawns. If a clear zone was generated where the filtrate was dropped, it could be judged that the bacteriophage capable of killing enteroinvasive E. coli was included in the filtrate. Through the above procedure, the filtrate containing the bacteriophage having the killing ability of enteroinvasive E. coli could be obtained.

Figure 1:
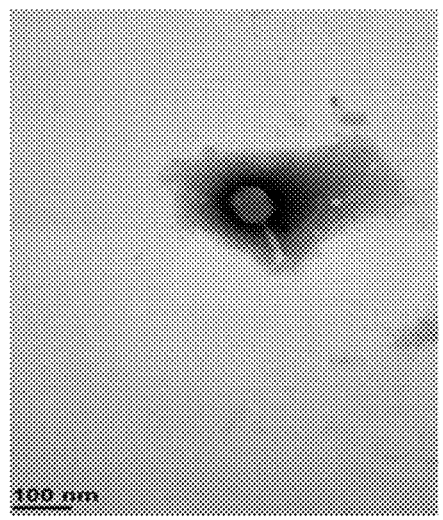
FIG. 1 is an electron micrograph showing the morphology of the bacteriophage Esc-COP-4.

After that, the bacteriophage was isolated from the filtrate confirmed above to have the bacteriophage capable of killing enteroinvasive E. coli. The conventional plaque assay was used for the isolation of pure bacteriophages. In detail, a plaque formed in the course of the plaque assay was picked up by using a sterilized tip, which was then added to the culture solution of enteroinvasive E. coli, followed by culturing for 4~5 hours. Upon completion of the culture, centrifugation was performed at 8,000 rpm for minutes to obtain supernatant. The recovered supernatant was inoculated with enteroinvasive E. coli culture at the ratio of 1/50, followed by culturing again for 4~5 hours. To increase the titer of the bacteriophage, the above procedure was repeated at least 5 times. Then, centrifugation was performed at 8,000 rpm for 20 minutes to obtain supernatant. Plaque assay was performed with the obtained supernatant. In general, the pure bacteriophage isolation is not completed by one-time procedure, so the above procedure was repeated by using the plague formed above. After at least 5 times of repeated procedure, the solution containing the pure bacteriophage was obtained. The procedure for the isolation of the pure bacteriophage was generally repeated until the generated plaques became similar in sizes and morphologies. And the final pure bacteriophage isolation was confirmed by the observation under electron microscope. Until the pure bacteriophage isolation was confirmed under electron microscope, the above procedure was repeated. The observation under electron microscope was performed by the conventional method. Briefly, the solution containing the pure bacteriophage was loaded on copper grid, followed by negative staining with 2% uranyl acetate. After drying thereof, the morphology was observed under transmission electron microscope. The electron micrograph of the bacteriophage isolated in the present invention is presented in FIG. 1. From the morphological observation, the bacteriophage isolated above was identified as belonging to the family Myoviridae.

The solution containing the pure bacteriophage confirmed above proceeded to purification. The culture broth of enteroinvasive E. coli was added to the solution containing the pure bacteriophage at the volume of ⅟₅₀ of the total volume of the bacteriophage solution, followed by culturing again for 4~5 hours. Upon completion of the culture, centrifugation was performed at 8,000 rpm for 20 minutes to obtain supernatant. This procedure was repeated 5 times to obtain a solution containing enough numbers of the bacteriophage. The supernatant obtained from the final centrifugation was filtered by a 0.45 μm filter, followed by the conventional polyethylene glycol (PEG) precipitation. Particularly, PEG and NaCl were added to 100 ml of the filtrate until reaching 10% PEG 8000/0.5 M NaCl, which stood at 4° C. for 2~3 hours. Then, centrifugation was performed at 8,000 rpm for 30 minutes to obtain the bacteriophage precipitate. The resulting bacteriophage precipitate was resuspended in 5 ml of buffer (10 mM Tris-HCl, 10 mM $MgSO_4$, 0.1% Gelatin, pH 8.0). This solution was called as the bacteriophage suspension or bacteriophage solution.

As a result, the pure bacteriophage purified above was collected, which was named as the bacteriophage Esc-COP-4 and then deposited at Korean Collection for Type Cultures, Korea Research Institute of Bioscience and Biotechnology in Aug. 21, 2014 (Accession NO: KCTC 12663BP).

Example 2: Separation and Sequence Analysis of the Bacteriophage Esc-COP-4 Genome The genome of the bacteriophage Esc-COP-4 was separated as follows. The genome was separated from the bacteriophage suspension obtained in Example 1. First, in order to eliminate DNA and RNA of enteroinvasive E. coli included in the suspension, DNase I and RNase A were added 200 U each to 10 ml of the bacteriophage suspension, which was incubated at 37° C. for 30 minutes. 30 minutes later, to remove the DNase I and RNase A activity, 500 μl of 0.5 M ethylenediaminetetraacetic acid (EDTA) was added thereto, which was incubated for 10 minutes. The suspension was further incubated at 65° C. for 10 minutes and then added with 100 μl of proteinase K (20 mg/ml) to break the outer wall of the bacteriophage, followed by incubation at 37° C. for 20 minutes. After that, 500 μl of 10% sodium dodecyl sulfate (SDS) solution was added thereto, followed by incubation at 65° C. for 1 hour. 10 ml of the mixture of phenol:chloroform:isoamylalcohol in a ratio of 25:24:1 was added thereto, followed by mixing well. The mixture was centrifuged at 13,000 rpm for 15 minutes to separate each layer. The upper layer was obtained, to which isopropyl alcohol was added at the volume of 1.5 times the volume of the upper layer, followed by centrifugation at 13,000 rpm for 10 minutes to precipitate the genome of the bacteriophage. After collecting the precipitate, 70% ethanol was added to the precipitate, followed by centrifugation at 13,000 rpm for 10 minutes to wash the precipitate. The washed precipitate was recovered, vacuum-dried and then dissolved in 100 μl of water. This procedure was repeated to obtain a sufficient amount of the bacteriophage Esc-COP-4 genome.

The nucleotide sequence of the genome of the bacteriophage Esc-COP-4 obtained above was analyzed by Next Generation Sequencing (NGS) using illumina Mi-Seq device at National Instrumentation Center for Environmental Management, Seoul National University. As a result, it is suggested that the final genome of bacteriophage Esc-COP-4 has 168,161 bp of size and the nucleotide sequence of the whole genome has SEQ. ID. NO: 1.

Similarity of the genomic sequence of the bacteriophage Esc-COP-4 obtained above with the previously reported bacteriophage genome sequences was investigated by using BLAST. From the BLAST result, it was confirmed that the genomic sequence of the bacteriophage Esc-COP-4 has high sequence homologies with the sequences of Shigella bacteriophage pSs-(Genbank Accession NO: KM501444.1), E. coli bacteriophage RB10 (Genbank Accession NO: KM606999.1), E. coli bacteriophage RB9 (Genbank Accession NO: KM606998.1), E. coli bacteriophage RB7 (Genbank Accession NO: KM606997.1) and E. coli bacteriophage RB6 (Genbank Accession NO: KM606996.1) (98%, 95%, 95%, 95% and 95%). However, their genome sizes were discriminated one another. Precisely, the whole genome of bacteriophage Esc-COP-4 was determined to have 168,161 bp of size, while whole genome of Shigella bacteriophage pSs-1 had 164,999 bp of size, that of E. coli bacteriophage RB10 had 168,401 bp of size, that of E. coli bacteriophage RB9 had 168,395 bp of size, that of E. coli bacteriophage RB7 had 168,395 bp of size and that of E. coli bacteriophage RB6 had 168,394 bp of size distinctly. Furthermore, the number of ORFs (Open Reading Frame) within the genome of bacteriophage Esc-COP-4 was determined to 267 ORFs, while the number of ORFs within Shigella bacteriophage pSs-1 was 266 ORFs, that of E. coli bacteriophage RB10 was 272 ORFs, that of E. coli bacteriophage RB9 was 272 ORFs, that of E. coli bacteriophage RB7 was 272 ORFs and that of E. coli bacteriophage RB6 was 271 ORFs distinctly.

Based upon this result, it is concluded that the bacteriophage Esc-COP-4 should be a novel bacteriophage not reported previously.

Figure 2:
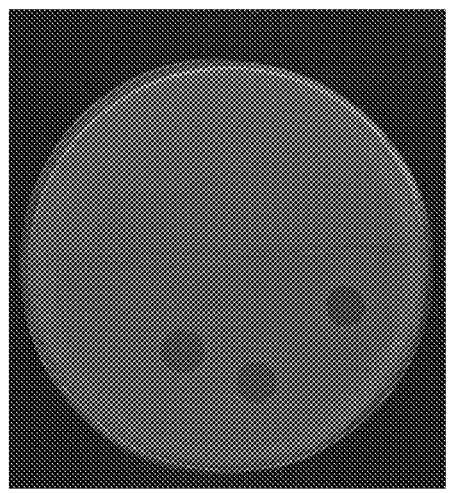
FIG. 2 is a photograph illustrating the capability of the bacteriophage Esc-COP-4 to kill enteroinvasive *E. coli*. The clear zone on the dish is the formation of plaque by lysis of bacteria cells.

Example 3: Investigation of Killing Ability of the Bacteriophage Esc-COP-4 Against Enteroinvasive E. coli The killing ability of the isolated bacteriophage Esc-COP-4 against enteroinvasive E. coli was investigated. To do so, the formation of clear zone was observed by the spot assay by the same manner as described in Example 1. The enteroinvasive E. coli used for this investigation were total 10 strains which had been isolated and identified as enteroinvasive E. coli previously by the present inventors. The bacteriophage Esc-COP-4 demonstrated the killing ability against 9 strains of the enteroinvasive E. coli used in this experiment. The representative result of the killing ability test is shown in FIG. 2. In the meantime, the activity of the bacteriophage Esc-COP-4 to kill Staphylococcus aureus, Enterococcus faecalis, Enterococcus faecium, Lactobacillus plantarum, Streptococcus uberis and Pseudomonas aeruginosa was also investigated. As a result, it is decided that the bacteriophage Esc-COP-4 did not have the killing activity against these microorganisms.

Therefore, it was confirmed that the bacteriophage Esc-COP-4 has the specific ability to kill enteroinvasive E. coli and a broad antibacterial spectrum against enteroinvasive E. coli, suggesting that the bacteriophage Esc-COP-4 of the present invention could be used as an active ingredient of the composition for preventing and treating the infections of enteroinvasive E. coli.

Example 4: Preventive Effect of Bacteriophage Esc-COP-4 on the Infections of Enteroinvasive E. coli 100 μl of the bacteriophage Esc-COP-4 solution at $3 \times 10^8$ pfu/ml was added to a tube containing 9 ml of TSB. To another tube containing 9 ml of TSB, only the same volume of TSB was added. Then, the enteroinvasive E. coli culture was added to each tube to prepare bacterial suspension in 0.5 of $OD_{600}$. After that, the tubes were transferred to an incubator at 37° C., followed by shaking culture, during which the growth of enteroinvasive E. coli was observed. As presented in Table 1, the growth of enteroinvasive E. coli was inhibited in the tube added with the bacteriophage Esc-COP-4 solution, while the growth of enteroinvasive E. coli was not inhibited in the tube without the bacteriophage Esc-COP-4 solution.

TABLE 1

Inhibition of growth of enteroinvasive E. coli

| item | $OD_{600}$ | | |
| --- | --- | --- | --- |
| | Culturing 0 min. | Culturing 60 min. | Culturing 120 min. |
| (−) bacteriophage solution | 0.5 | 1.6 | 2.0 |
| (+) bacteriophage solution | 0.5 | 0.4 | 0.3 |

The above results indicate that the bacteriophage Esc-COP-4 not only inhibited the growth of enteroinvasive E. coli but also could kill them. Therefore, the bacteriophage Esc-COP-4 can be used as an active ingredient of the composition for preventing the infections of enteroinvasive E. coli.

Example 5: Therapeutic Effect of Bacteriophage Esc-COP-4 on the Infections of Enteroinvasive E. coli Therapeutic effect of the bacteriophage Esc-COP-4 on animals affected by enteroinvasive E. coli was investigated. 4 weaning pigs at 25 days of age were grouped together; total 2 groups of pigs were raised in a pig pen (1.1 m×1.0 m) for 14 days. Heating system was furnished and the surrounding environment was controlled. The temperature and the humidity of the pig pen were controlled and the floor was cleaned every day. On the 7$^{th}$ day of the experiment, all the animals were orally administered with 1 mL of enteroinvasive E. coli suspension using an oral injection tube. The enteroinvasive E. coli suspension administered above was prepared as follows: enteroinvasive E. coli was cultured in TSB medium at 37° C. for 18 hours and the bacterial cells were collected by centrifugation. Saline (pH 7.2) was added to the bacterial cell pellet to make cell suspension at a concentration of $10^9$ CFU/ml. From the next day of the enteroinvasive E. coli challenge, the experimental group (bacteriophage solution treated pigs) were orally administered with the bacteriophage Esc-COP-4 ($10^9$ PFU/head) via the same way as used for the above administration twice a day. The control group (bacteriophage solution non-treated pigs) was treated with nothing. Feeds and drinking water were equally provided to both groups. After the challenge of enteroinvasive *E. coli*, all the animals were observed every day whether or not they experienced diarrhea. The observation was performed by measuring the diarrhea index. The diarrhea index was set as follows according to Fecal Consistency (FC) score (normal: 0, loose stool: 1, moderate diarrhea: 2, and severe diarrhea: 3). The results are shown in Table 2.

TABLE 2

| | Fecal Consistency score | | | | | | | |
|---|---|---|---|---|---|---|---|---|
| Days after enteroinvasive *E. coli* challenge | 0 | 1 | 2 | 3 | 4 | 5 | 6 | 7 |
| Control group (− bacteriophage solution) | 2.5 | 2.25 | 2 | 2.25 | 2 | 2 | 1.5 | 1.5 |
| Experimental group (+ bacteriophage solution) | 2.5 | 1 | 0.5 | 0.25 | 0 | 0 | 0 | 0 |

From the above results, it is confirmed that the bacteriophage Esc-COP-4 of the present invention could be very effective to treat the infections of enteroinvasive *E. coli*.

Example 6: Preparation of Feed Additives and Feeds

Feed additive containing bacteriophage Esc-COP-4 at a concentration of $1\times10^8$ pfu/g was prepared using the bacteriophage Esc-COP-4 solution. The preparation method thereof was as follows: Maltodextrin (40%, w/v) was added to the bacteriophage solution and then, trehalose was added to reach 10% of final concentration. After mixing well, the mixture was freeze-dried. Lastly, the dried mixture was grinded into fine powders. The drying process above can be replaced with vacuum-drying, drying at warm temperature, or drying at room temperature. To prepare the control feed additive for comparison, feed additive that did not contain the bacteriophage but contained buffer (10 mM Tris-HCl, 10 mM $MgSO_4$, 0.1% Gelatin, pH 8.0) only was prepared.

The above two kinds of feed additives were mixed with the 1,000 times volume of feed for pig farming respectively, resulting in two kinds of final feeds.

Example 7: Preparation of Drinking Water Additives and Disinfectants

Drinking water additive and disinfectant are different in intended use but same in the composition, so they have been prepared by the same manner. Drinking water additive (or disinfectant) containing bacteriophage Esc-COP-4 at a concentration of $1\times10^8$ pfu/ml was prepared using the bacteriophage Esc-COP-4 solution. Particularly, to prepare drinking water additive (or disinfectant), the bacteriophage ESC-COP-solution was added to buffer solution to reach $1\times10^8$ pfu/ml, which was mixed well. For the comparison, the above buffer solution itself was used as the drinking water additive (or disinfectant) that did not contain the bacteriophage.

The prepared two kinds of drinking water additives (or disinfectants) were diluted in water at the ratio of 1:1000, and then used as drinking water or disinfectant.

Example 8: Effect on Pig Farming

The effect of the feeds, drinking water, and disinfectant prepared in Example 6 and Example 7 on pig farming was investigated. Particularly, the investigation was focused on diarrhea conditions by fecal consistency score used in Example 5. Total 30 piglets were grouped into three groups, and each group was composed of 10 piglets (group A: feed test group, group B: drinking water test group; and group C: disinfectant test group). The experiment was continued for 2 weeks. Each group was divided by two sub-groups comprising 5 piglets each. The sub-groups were divided according to the treatment of the bacteriophage Esc-COP-4 or not (sub-group-①: treated with the bacteriophage Esc-COP-4; and sub-group-②: not-treated with the bacteriophage). The piglets used in this experiment were weaning pigs at 20 days of age and raised in a separated room placed at a sufficient distance from each other. Each sub-group was divided and named as shown in Table 3.

TABLE 3

| | Sub-groups of pig farming experiment | |
|---|---|---|
| | Sub-group | |
| Item | Treated with the bacteriophage Esc-COP-4 | Not-treated with the bacteriophage |
| Fed with feeds | A-① | A-② |
| Provided with drinking water | B-① | B-② |
| Treated with disinfectant | C-① | C-② |

Feeds were provided according to the conventional feed supply method as presented in Table 3 with the feeds prepared in Example 6. Drinking water was provided according to the conventional water supply method as presented in Table 3 with the drinking water prepared in Example 7. Disinfectant was treated three times a week with taking turns with the conventional disinfectant. That is, on the day when the disinfectant of the present invention was sprayed, the conventional disinfectant was not treated. The results are shown in Table 4.

TABLE 4

| | Fecal consistency score of pig farming experiment | | | | | | | | | | | | | |
|---|---|---|---|---|---|---|---|---|---|---|---|---|---|---|
| Group | Fecal consistency score | | | | | | | | | | | | | |
| 그룹 | d1 | d2 | d3 | d4 | d5 | d6 | d7 | d8 | d9 | d10 | d11 | d12 | d13 | d14 |
| A-① | 0.2 | 0 | 0 | 0.2 | 0 | 0 | 0.2 | 0 | 0.2 | 0 | 0 | 0.2 | 0 | 0 |
| A-② | 0.2 | 0.4 | 0.4 | 0.4 | 0.2 | 0.2 | 0.4 | 0.2 | 0.4 | 0.4 | 0.4 | 0.4 | 0.2 | 0.2 |
| B-① | 0 | 0 | 0 | 0 | 0 | 0 | 0.2 | 0 | 0 | 0 | 0 | 0 | 0.2 | 0 |
| B-② | 0.2 | 0.4 | 0.2 | 0.4 | 0.4 | 0.4 | 0.2 | 0.4 | 0.4 | 0.4 | 0.2 | 0.4 | 0.4 | 0.2 |

TABLE 4-continued

Fecal consistency score of pig farming experiment

| Group | Fecal consistency score | | | | | | | | | | | | | |
|---|---|---|---|---|---|---|---|---|---|---|---|---|---|---|
| 그룹 | d1 | d2 | d3 | d4 | d5 | d6 | d7 | d8 | d9 | d10 | d11 | d12 | d13 | d14 |
| C-① | 0.2 | 0 | 0 | 0.2 | 0 | 0.2 | 0 | 0.2 | 0 | 0 | 0 | 0 | 0 | 0 |
| C-② | 0 | 0.2 | 0.4 | 0.2 | 0.4 | 0.4 | 0.4 | 0.4 | 0.4 | 0.2 | 0.2 | 0.4 | 0.2 | 0.4 |

From the above results, it is confirmed that the feeds, drinking water, and the disinfectant prepared according to the present invention were effective in reducing the animal diarrhea. Therefore, it is concluded that the composition of the present invention could be efficiently applied for the improvement of productivity of animal farming.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended Claims.

What is claimed is:

1. A method for preventing or treating infections of enteroinvasive *E. coli* in a subject, the method comprising a step of administering to the subject a composition comprising Myoviridae bacteriophage Esc-COP-4 (Accession NO: KCTC 12663BP) that is isolated from nature and can kill enteroinvasive *E. coli* specifically, which has the genome represented by the nucleotide sequence of SEQ ID NO: 1, as an active ingredient.

2. The method according to claim 1, wherein said composition is administered to the subject in the form of a feed additive, a drinking water additive, or a disinfectant.

* * * * *

```
                              SEQUENCE LISTING

<160> NUMBER OF SEQ ID NOS: 1

<210> SEQ ID NO 1
<211> LENGTH: 168161
<212> TYPE: DNA
<213> ORGANISM: Bacteriophage Esc-COP-4

<400> SEQUENCE: 1
agtatgaata taattaataa gattttttgga attcaataca ttaaagtcac atataaagta      60
acgtataaag gtccgtatac cgatgaacat gaagaaccac aagttaagtc tattatatta     120
gaaaaggacc ctaactggcc agttgaattt cgtcttcctt gctatagtca ttgggctgat     180
gttgaaatta taagtattga aaatgtctga gttagagatt agaagcaatt ttagatggcc     240
atcatgcgca ttaagtaatt tcgcccaatg gcctttttgtt atggatagta tccaatttgg     300
aggtctcgaa ggattcctcc aagggtgtaa ggtgaaaaat gttgaacagc aacgtcgtat     360 atttggggtta tccgggcttg ccgcccaaca agctggacga gcttatgcta gagctcagga     420
ccgtggcacg ttgttctggc ttggagttcc gttttcaaga tactctccag cgtggaaaga     480
attatacaca aatgcatatt ttgaagcagc gttccaaaat aagggctttc gtgatgcatt     540
acaagcctcg aaaggaaaag ttttgaagca cagcatggct agtggtctaa caaaagatga     600
tacaatacta accgaagctg aatttattga tgtgttaaac ctattaagag actctctatg     660
aagcctacta ttttaactga tattgatgga gtatgtttaa gctggcaatc aggacttcct     720
tattttgctc agaaatataa tcttccgtta gaacatattt taaaaatgat ccaagatgag     780
aaatttattt ctccaggtaa actctttaat tgtgatgaag aacttggtgt caagttaatt     840
gaaaaataca atcgttcaga ttttattcgt tacttgtctc catataaaga tgcattgtgc     900
gtaattaaca aactaaaaga agattataat tttgtggctg ttacggcatt gggtgattct     960
attgacgctc tgctgaatcg tcaatttaat ttgaatgctc ttttttcctgg tgccttctca    1020 gaagtaatga tgtgtggtca tgattcttca aaagaagagt tattcaaaaa ggcaaaagag    1080
aaatataacg taatttgtta tattgacgat ctcgctcacc attgcgatca tgcgagtgaa    1140
atattaaatg ttccggttta ttggatggct cgaggagagc gtgacaatat tccaaaaact    1200
gctcagcgag tttatacatg gaatgatgta gaaaataagc tttttttcgcc gaaggaaaat    1260 aaagaaagtt ttgatagtga aaaagctata aaagatttaa ttgagaagat ggttaaaaac    1320
gattcttttc cttggaacac tacctggaga acgcctggat ttaatcctta taatcatcta    1380
```

```
tatcatccat atcatccata tcagacacat ccatttcaga catggaacta tattaaacct    1440
ggtggcatag agtatttgta aatagacct acttgtggtg ataatatttt ccaaggagca    1500
ttctaatgtt tgtcgttcac actatttatg aaaatgaagg taatattaca cgtgattatg    1560
gtcacgtaaa tcaattttt agatgcaatc cagaattccg tgctcaaaaa gacgaacgaa    1620
tttttaaaaa atgtgtagaa caaggtttca tttacgtcaa gcactggatg caaggaaata    1680
aagttagaac tacatatcat aagtctttgc ctgagcttaa tgatgaattg atttataata    1740
gagatgtaaa tcaaactctg aaggatgaac aatgattctt aaaattctga atgaaatagc    1800
atctattgga tcaactaagc agaagcaagc aattcttgaa aagaataaag ataacgaatt    1860
gcttaaacga gtatatcgtc tgacttattc tcgtgggtta cagtattata tcaagaaatg    1920
gcctaagcct ggtattgcta cccagagttt tggaatgctg actattaccg atatgcttga    1980
cttcattgaa ttcacgttag ctactcggaa attaactggc aatgcagcaa ttgaggaatt    2040
aactggatat atcaccgatg gtaaaaagga tgatgttgaa gttttgcgtc gagttatgat    2100
gcgagacctt gaatgcggtg cttcagtatc tattgcaaac aaagtttggc cgggtttaat    2160
tcctgaacaa cctcaaatgc tggcaagttc ttatgatgaa aaaggcatta gtaagaatat    2220
caaatttcca gcctttgcac agttaaaagc agatggagct cggtgttttg ctgaagtccg    2280
aggtgatgaa ttagatgatg ttcgtctttt atcacgagct ggtaatgaat atctaggatt    2340
agatcttctt aaggaagaat taatcaaaat gactgctgaa gcccgccaga ttcatccaga    2400
aggcgtgtta atcgatggcg aattggtata ccatgagcaa gttgaaaaag agccagaagg    2460
cctagatttt cttttgatg ctcctgaaat cagtaaagct aaagagtttg ccgaagtagc    2520
tgaatctcgt actacttcta atggaatcgc aataaatcc ttaaaaggaa ccatttctga    2580 aaagaagct caatgtatga agtttcaggt ctgggattat gtcccgttgg tagaaatata    2640
cggtcttccg acgtttcgtt tgaagtatga tgcacgtttt tctaaactag aacaaatgac    2700
atcaggatat gataaagtaa tttaattga aaaccaggta gtaaataacc tagatgaagc    2760
taaggtaatt tataaaagt atattgacca aggtcttgaa ggtattattc tcaaaaatat    2820
cgatggatta tgggaaaatg ctcgttcaaa aaatctctat aaatttaaag aagtaattga    2880
tgttgattta aaattgtag aatttatcc tcaccgtaaa gaccctacta agcaggtgg    2940 attattctt gaatcagagt gtggaaaaat taaagtaaat gctggttcag gcttaaaaga    3000
taaagccggt gtaaaatcgc atgaacttga ccgtactcgc attatggaaa accaaaatta    3060
ttatattgga aaattctag aatgcgaatg taatggttgg ttaaaatctg acggccgcac    3120
tgattacgtt aaattatttc ttccaattgc gattcgttta cgtgaagata aaactaaagc    3180
taatacattc gaggatgtat ttggtgattt tcatgaggta actggtctat gaaagcttac    3240
ttagaaacaa ttgtcgttgc tcaaaaagaa ggtggagatg tttctacttc tgtatcacaa    3300
attatgattg aatttataga tgcgtatgct taataaaat tcacagaaac atttgatgcc    3360
tatgaaaaag gtccaaagtt tgaaatatac cgtactctct taccaataga ttattaaagg    3420
ccttcgggcc tttaattta aaatagaat aaacactaga gaggatatga tggaactcat    3480
tacagaatta tttgacgaag atactactct tccgattaca aacttaaatc caagaagaa    3540 aataccgcaa atttttcag ttcatgttga tgacgcaatt gaacaaccag gctttcgttt    3600
atgtacctat acatctggag gtgatactaa tcgcgattta aagatgggcg ataaaatgat    3660
gcatattgtt cctttacat taactgctaa aggttcaatt gctaaattaa aaggtctcgg    3720
tccaagccca attaattaca tcaattcagt ttttactgtt gcgatgcaga cgatgcgtca    3780
```

```
gtataaaatt gatgcctgca tgctccgtat tcttaagtct aaaactgctg gtcaagctcg    3840
tcaaattcaa cttattgctg atagacttat ccgtagtcgt tcaggtggca gatacgtcct    3900
tcttaaggaa atctgggatt acgataaaaa gtatgcatat attatggttt accgtaaaaa    3960
tgccaattta gaagacattc caggtgtacc tcctatttca actgagttat tcacaaaagt    4020
tgaatcaaag gttggtgatg tttatgtaga tgttaaaacg ggtaatgctg ttcctaaagc    4080
tgttgctgtt gctgcttcta ttgctttaga aaatgataag cgcacggatc aagctgttat    4140
tcagaaaact aaaattagtc gtcgattagc agcgcaagct caatattcta ctgttgatgc    4200
ttcacttcag ggtgatagct tcgccgctaa gaaatatcaa gagtttgaat ctaaagttcc    4260
ggtatataaa gcagaaggac caatgaactc tggcgttatt cagattggtt caaacttcgg    4320
caaaggagct atcggtggta tgagaagtgc ttctcgtttt aaatctaacg attatgaact    4380
agaaagcttc cgaaatcata ttgcattggc ccatgcacgt ttacgtgatc cgtctatcag    4440
actgcagagc gatataacac atcaaggttc tcaagaatat ttaaagaata aagaattctt    4500
tgattataaa accgataaaa ttttgagcga tctcgctgac attaatattt ctaatagctt    4560
tgatgttatt aagaaaatta tcaatgattt agttaaaggt tctaaagcta cgccagacga    4620
aaaggtagct attattcaat ttgtcatgaa tggcatttat aaattgatta atgaatctgc    4680
tgctcaggca tatgaatacg caagcaccga agtaactcca aaaggactga ctcaggctga    4740
gtctgatgta attgaagatt attgtgcaga ttcatatgtt gaaatgaact cgttcctttt    4800 aggtaaaccca gattctaccc gtgaagaata catggaacga gctattaaac acatcgagac    4860
tctggattct gcattcgcca aaggatcagt tcttcctccg ggaactacgc tttatcgtgg    4920
tcaagaagtt acttttaaaa ctttacgcca taatattgaa aataaaatgt tctatttcaa    4980
gaacttcgta tccacatcgc ttaaaccaaa tatcttcggt gagcatggta aaaactatat    5040
ggctctagat gattccggcg cagtattttc tggtgaagga gaaggttctg ttgatgctga    5100
agatttaatg catatgggca gtcattctgc ttatgcgaat gaagatgctg aaactagcgt    5160
aggtatggta attaaagggg ctgagcgaat caaagttatc gttccaggtc atttatcagg    5220
atttccatca gaagctgaag ttattctacc gcgtggaatt tgttgaaga ttaataaagt    5280 aagcacgtac atgatgaaag aaactgctta taacaagtat ctaatcgaag gcacaatcgt    5340
tcctccttct gaacaattag aagaatcggt atatgatggc gatcatctaa tggaaactgg    5400
tgaagttcgt ccaatggctg ggtttaatca attccttgta gaagaatcaa agaagaggaa    5460
aaacgaagtt tctcaaatct tggcttcttt ggttaacatc aacagaatgt ctaaaaagtt    5520
caagatgtag tttacaagtc cctcgtgttg tgttatagta gtcttactga cataacatga    5580
ggaacacaaa atgaaatctt ctttacgctt tttaggtcaa gaacttgtag ttgaaggcgt    5640
tattcctgct gataacgctt ttaatgaagc agtttatgat gaatttatca aaatttttgg    5700
aacagataaa aagttcggaa ttttccttc tgaaaatttt tcaaagccag aacagactga    5760
aagcattttc caaggtgtag taacaggtaa atttgagtca gaagctccgg taaaaattga    5820
agtttatatt gaagacagtt tagttgcttc agttgctgct ttcatttcat tccgtaaata    5880
aaaatatggg gacctttcgg tccccattgt tatattgctc ctaatatttt actctgcgag    5940
ttgacaattc ccgtcatagt attaatgttt gaaatgcttc cagcagttcc ccctaatcta    6000
ctaagtcgtg aaagcgaatt agataatcca gtaacgcctc cactatttcc gagaacgctt    6060
tgaataccgt ttatagcagc agattcaagc cattcagggg cagcttgtct atcaactgct    6120
ccagcctgca tgactctata cgcaaaagta acatcaaacg tagttatttg gttatctcca    6180
```

```
tcatatgata actcaggagc gctcactgac actggaatgc atccggtgaa catcactgca    6240
gtatgaggta atccattacg agcatgaaga ttaacctgaa tatctgcctc gacatcttgt    6300
ggcaaagcac gcagtccagt tactgggtct tgaacagcgt taacccagtc ttgcattgca    6360
cgatagttac aagcttctga atccattcta aatgaaataa ccaaagggtc taattctctc    6420
ccagttatac gaatattagg agagttatag ttccagtcag tttcatagga taatctattc    6480
tctggcattt ttacagaata tatcatcaac ccagatgagt tatatgccat gttaaagaag    6540
tcaattaaat atgtaccaac tgtaaatgag cccaataaac tttgaactgt acgttgactc    6600
atggcaccaa taagatattt actaacccct gattttctta tcagttttg tgtgccagca    6660
gtaattagcg tggtaattcc ctgattaata tcgccttgag acaatcctaa ccagtctgaa    6720
tttagaccca aattattata agaaaagttg ctaattgaac ttatcaacga gagcttta     6780
gttgatggag ttgtcgcaaa aacgcagcta acatattat tacgttggaa atctgcgttt    6840
attgcttgat tattaaattc ctctaaagaa tacattaaaa agtccccgca tataaagaag    6900
cacgatttaa cgtgataatt tctctcatag taatctcaag agtaaatgta ctagggaggt    6960
ttggagcaat agctaatccg ttaaagttac cattaggtgt tttatcaaat ctgatgctct    7020
gtatttggca tgggccaaat atttccgttt ttccatcaaa cttagatgtt gcaccaaagt    7080
ttttcaccat ccaaattgtt gggtttgaaa ctactagaac gttagttaaa ctcgatgtca    7140
ttttctcaaa tagtgtttta tttttagctg cgtcttccgg agataaaggt tcaattaatg    7200
tagaacgata ccaatcatct aaataccct ttatttcagc agcatattga gatttgcccg    7260
tttcaccata agaaaaatag ttaaaatatt gatagatatt gataatagcc atcaaatctt    7320
ctgttgaacg cggagtcaaa tcccatgtaa acactttagt tctattctca gcaccaccat    7380
acatacttct ggctgtcgta taaatctgtt cattattatc agccattata ccttgtgtta    7440
tactttccag tgccccaaat actgcagttg aagcaatatt acttaacaca ccagtagcag    7500
tacctccgcc tctgctgata agactttctt gaacatcatt aaatctatgt gatgatgtat    7560
caacgtcaga tttagatctc ggtaaaagaa tgtttgcgac aggagcttta cttattgttc    7620
ctgaattatt gtttgatatt aatccatttg atagttttga tactgtacta ctaatagtgt    7680
ttctagctgt acttaaaata ctcgaagatg aagaagagta gttagatctc atcgatctaa    7740
gacttccaga atccctagat gacatattgt atgcagtaaa taataatcca ttcttatata    7800
ggtctgttac ctggaagtcc cctgtagtgt cattaccact agcacgccca gttggaaact    7860
gggcagtgta tgttttagtt gctacttctg atttagtact ctgtccggct gaaattttct    7920
caccggactt tttaattaaa tcagcagtta tttctttaac aattgccata ttattcctta    7980
attaactcca gtcgcatcaa atacaccagg agcagtcgtg ctcgttacgg gtgtcatatt    8040
atgaacgaca gtattttct taataacatt attagtatta ttgattgaag gagatgcttg    8100
ttaacagga gcttgctgtg ctttgttctt ttctattacc tggacttgtt ttgcttctgg    8160
cgatttagca gaagtttgag gtttggcatt aggctgattt ttcttgagct cttgataagt    8220
agcatcaatt ttagaaaatc tagcagcaag ttctttttta actgccggtg aattatttaa    8280
atccgggtca tccatccgtt ttttaaggtc ttcataggca gcttcaactg atttaaccgt    8340
tgagtcttta ctcatatcag ctgaattagc gtattcatca aaacgattca tagcagcacg    8400
agcttcatta gctttcatta aagcaatttt agcttcctcc ggagaaagtt gctttaattt    8460
ttcttcttcc tctgctctct cttcatcagt cgttagtgct tctttattat caacaccacg    8520
aatccagtta gatgcacgag ttttccagtt cgcaattttg tctagcccctt ttgctattgg    8580
```

```
accaagatcg ccattcattc ttttatattg ataatttgca acttttttctt ggtcttcttt      8640 gctaagagaa gcatttgtag tattttggaa attttctagt gctcttcctt ctacttcgtc      8700
agcagtgtct ttcatgccag gaataactcg aagaattgcc gcagataatt tagccattcc      8760
aagttgaata agctctccta aattaaaaag aacctttcca agcccttcta caatagctgc      8820
tgtcaatccg ccccaatctc cggcttccca cagcttctta attttatcaa tagaactaaa      8880
gatgctctgt aataaaggac cccatgttcc ggtttcgcta gagaatttag taaagtttga      8940
actaaacaaa tcccaagcct gcgaaaattt atctgaccaa tatttaaagt gaaccatcag      9000
cagatctatt ccaacaacaa cagcaatat cattgcagtc attttagcgg cttcaatagc       9060
agcactgacg gtatacttaa atagcatgct tgatatttta tcagtaattg aaatagattt      9120
cttaaatccg aaatcaacag tctttgttaa tttatctaaa gcttgagata attttaagtt     9180
aaatgcgtct ttttctgtt tttcttctgg cgattcttgt ttgggttcaa ctggctgagg       9240
ggtagggaaa aaatcagcat caggatcatt attaaccgct tcaggagctg gtaataaagg      9300
accaacagat tcagctgtat catcctcaac gactttaaca ggaatagcgc tttcaaccgt      9360 ggctaaaacta gttcctgttt gttgaattcc ggctgtctga attttttgct ctagtaaact    9420
cgttaattta tctaatttac ttccgagcga ttcgccaatt tctttattaa tattgttgcc     9480
aatttcgaca gtttcagcaa ttaactcaga accagcagta gtatcactca ctgcgctttc     9540
tacattgtca attgctccaa ttatttcatt cgattttctct tcaacggttt gagctattaa    9600
ttcagaagca gcttgagcat catccaattt tgtagaaatg tcattaagcc cagataaagt     9660
gttagaagcg gatttagccg cttcctgaac tggtttatta tctgaaataa cttttctacg     9720
catcgtttgc atttcttgtg gcttttttcat tcaaataatc caataatatt gccaattcca    9780
gttattggac cattagggcc aggaattgct aaagttgtaa aaatatcatt tgcccatttt     9840
aaaacgaatg ctggcatctc aagaaaatta atttctttaa cttcatcatt gaccttaagc     9900
aagcatttag ataacatatc gctcaccgtt aaaaattgtt caaattttcc aggaggtcta     9960
aaataaaatg tatttccttg gtattgaaat tctaatcttt ggcacacata acatcatta     10020 atgtcataag tataaccatc tatttctta cgagatttaa tctttccatt aaattccaat     10080
aaatgaatag aaacgaaatc aacttctgct ggtgataaat tcggacaaat agaatcaata    10140
agaagtttta aattttcatc aggacctttta acatcttttta aaatgttata atgtttaaga  10200 cccatttttag gaatagaaac ttcttttattg cttattggaa gaactacttt cttcagtggt  10260
agtatcagat ttaaattcat ttttaacctt aactgggtct attgtttcca gtttcgttgc    10320
attagtgaac atatatagat gagttactga attattattg gataattcat ggataacttc    10380
atcaacgtaa aattctgttt taaattggtt tttactatca ttaaaaataa ttttaacgcc    10440
aggagtcaag ttaaaattac cgacagtaga acatttagca tagccatcgt attgtgccat    10500
agtttgaaga cgaatagctt cttcatatcc attcctataa gtcatttcag aataagcacc    10560
tgaccttgat actacaatag agttttcgcc cttttcctgta gtaatcattg gcaatgaaga   10620
atctaaaaat gaatgagcat agatagtagc attttttcatt gggtcgcgtt tatgaggatt  10680
cgatttagtc aaccaaacga aatcatatgc taatggatat tttaattctt ggatgaattg    10740
acctattaaa gatggctcac cgacaatcat tggatacggt tcttgattta tcatcatatc    10800
atagtccatc atgttaactc ccatgatgtc ttgccacaca aatacaaatt tgtcacttcc    10860
tacagctaga gcaacttccc tgacatacga caaatagttt tcaaatgtgc tagtccatgg    10920
```

```
aatatcagga acataagcat ttatagcatt tattgctgga gttaataacg tgcgatcctg    10980
ataaatgacg ccaagcattt cctttataga ttcacctgca tcagagaaaa acggtctgcc    11040
aaatttaaga ttttctatgg aatgaatagt tcccaattca atagcaatga tgttatcacc    11100
ttttgaatct acagatacag aaaaatgctt acatccataa attcgtgttt taacattatt    11160
aatatcgttt gcattagcta cagaaatctg aattatttca tttccatcca tttttgtatg    11220 gatatttta gaatcataaa actgcagcat tccttcattt cggccataaa gagaatcccg    11280
catagttaat gtggtaatag tagcagctaa ttcaacaaat ctattattac tccaagcgtc    11340
gtagctatca ataatttaa cgctgagatt tggatatcct gggcgttgca acatactcat    11400
tattgtttat ccttctcaat cagttttaat acgaatccgc gctcagcagg aatcattttc    11460
attattgaat ttaagctata attacttttt acgagcgtgt gattgatttg ataaaaagta    11520
aatatttcat ctgggttaac taatagctta aacacatcta ctatatcagt gtattttttt    11580
acatacttat tacaacatga catatgcaat gttaaattaa taggattcat tgcatcgaga    11640
attttttcta atgtttctat ctcgatggca tcaacaagtt ctatttgact cgattcgctg    11700
atttccttcc aatcatacca catttcatct acttgaacag aatgaatatt ttcagtaatc    11760
atctttgctt tattttcata aaactcagaa ggaaacttta atttaatttt aacattagct    11820
acatcaaaaa caggttcctt taattctttt tgatatattt caaatggaac tgtcttttct    11880
tttttacatt ttgacatac aaatgtgacc ggtactttag ttttacctat tgaccctaca    11940
aatacctgca aaaatataaa tggttgccaa gtcttcggat agtctccaaa ataatcagca    12000
attaaatcag caattatttc ttttttgttct tgtggtgacc gatgttctat atcgtttcga    12060
actaacaaaa aatctcgata atcttctacc gtaaatggtt taaaacgatg aacaccatct    12120
ggtaatttac aacgaataat gtttgccata gatgctcctt ttattctatt tataaatatg    12180
ataaataaag gagctaaata tgtatgaata caaatttgat gcgagagttg gttctaaaat    12240
aatcaactgt cgcgcattta ctcttaaaga atatctagaa cttattactg ctaaaaagaa    12300
cggttcagta gaagagatcg ttaaaaagct aatcaaagaa tgcacaaatg caaaagattt    12360
aaaccgccaa gaatcagaac tactgctgat tcatttatgg gcacattctc ttggagaagt    12420
taatcacgaa aactcctgga agtgcacctg tggaactgaa ataccaaccc atataaatct    12480
attacataca caaatagatg caccagaaga cctctggtat acactgggtg acattaaaat    12540
taagttccat taccctaaaa ttttttgatga taaaaatata gcccacatga tagtatcatg    12600
tatagaaacg attcatgcta acgggggaaag cattccagtt gaagacttaa atgaaaaaga    12660
actggaagat ttatattcta tcatcacaga gtcagatatt gtagctataa aagatatgct    12720
tttaaagcct actgtttatt tggctgttcc aattaagtgt ccagagtgtg aaaaaactca    12780
cgctcatgta ataagaggac tcaaagaatt ctttgagcta ttgtaatggc aaatattaat    12840
aagctttatt ctgacattga cccagaaatg aaaatggatt gggacaaaga tgtttcaaga    12900
tctcttggat taaggtcaat taaaaatagc cttttaggaa ttattacaac caggaaaggg    12960
tcaaggccat ttgacccaga atttggatgt gatttatctg atcagctttt tgagaatatg    13020
actcctctta ctgctgatac tgttgagcgt aacattgaaa gcgcagtaag aaactacgag    13080
ccgcgtattg ataaattagc agttaatgta ataccggttt atgatgatta tactctgata    13140
gtagaaatac gcttttcagt catcgataac cctgatgata ttgagcagat aaaactacaa    13200
ctggcttcca gtaacagagt ataatgcttc acgtataaac gtggtataat gaatctaagt    13260
ccatccaata acaattgaat agagaacaat atgaaattag aagatcttca agaagaattg    13320
```

```
aagaaagatg tgtttataga ttcgactaaa ttacagtatg aagcagctaa taatgtgatg    13380
ttatatagta aatggctcaa taagcattca agtattaaaa aggaaatgct tagaattgaa    13440
gcacagaaaa aagttgctct taaagctaaa ttagactact actcgggacg aggagatggt    13500
gatgaattta gtatggaccg ttatgagaaa tcagaaatga agacagttct atcagctgat    13560
aaggatgttt taaaagttga tacttcattg cagtattggg gaattttatt ggatttctgt    13620
agcggagctc ttgatgctat taaatcacgc ggatttgcta ttaagcatat tcaagacatg    13680
cgagcatttg aggctggaaa ataatgagat atagcattga tgatgctttt aattatgaag    13740
aagaattcga acggaaatt caattttta tgaaaaagta taatcttaag cgtcaggata      13800
ttcgtatcct ggccgaccat ccatgtggtg aagatgtact ttatgttaaa ggaaaatttg    13860
ccggatatct tgatgaatat ttttattcta aagatatggg cattgatatg catatgagag    13920
ttatataaat agatatataa tttagaggag acaatcatgt cagataagat ttgcgttgtc    13980
tgtaaaactc caatcgattc tgcattggtt gttgaaacag acaaaggtcc tgtacatcct    14040
gggccttgtt ataattacat taaagaacta ccagtttcag aaagttcgga agaacaatta    14100
aatgaaacac aactttttgct atagtgtgac ctttagtcta tagttttggc ccttcctttt    14160
tggttgggcc ttttttaatt taaaagcttt cttctacttc atcgtctgaa tcttctaatt    14220 cagctcttt tcctgccaaa gcatctctca cagagatgtc atcagtatct tttaattcag    14280
tttctttaac tcttttctta taataagctt caagttcttc tagaccttct attgtttgac    14340
aagaggcaat tttacccata aattcatcaa tagaagcttc ataaagaaat tgtttaaatt    14400
ctagtaacat cttttctcc aaagggccga agcccttata aattaactgt ttttctaagt     14460
attcttagtt tgtacattga taatccagta gctttagaag catctttcat gcagttatac    14520
ttaacaccat ttacttctat aggtttagca gctgggttat tagctcctga attatctggc    14580
atgttatctt taattttctg aatagattta gcggaatgtt tccttccata catgccatta    14640
tttttacctg attgattgat agaatgcaat cttttagctt cttcagtcca ttttgttggg    14700
ttcattcttt tagtttttact aattttactt ccccacgtaa ttggacgatt tttcatgagt    14760
tttgacatat attgttatg ttcttccgta tggtgttttc cgtaaaatgg attaccttca     14820
cctgattgaa gttttgccat tttacgacgt tcccaggcgt aagatttatt aacgtgtctt    14880
tcatgagtat ttgaattcat tcccatacat ataacggctt taattatacc gtaatggttt    14940
ggatgaattt tagctaaaag tttatgagct ataaaatgct cttcagctgt tagttctacc    15000
aaattacact tatcatctgt accacccata catctaggaa ttatatgatg agtttcagtg    15060
tatccattaa ggcgagcccg attctgggct ctattaatta aattatcata tattaattta    15120
taattcaaag tttaacctct ttcatcacat aattaaactt ctcatcagca taacgctgaa    15180
tacgatcaag tccatgtttt aaaagatagt ttaaatgcga gtatttttta gaagatgttt    15240
ttgatttaga aactacgccc gcgtcatcta tgaggtccca gaccgttgcg attgttttag    15300
aaccatgctt acgtaatacg cgacctattg tttgtaatac aataatttta gatttaacac    15360
cgtgtgctaa aacaacgtga tgcagatttt taactgaaat accggtagaa aatacaccat    15420
aactagctac tataattatt cctttaccgt tttcagctaa ggttttcatt atattgcggg    15480
tttcggtatc aacttcccct gatacgtaat aaactttatc gtattcattt ttaattaaat    15540
cgaaaatagc tttaccgtgc gatacgtgtt taaacatgac aaaagcattt tcatcttttt    15600
gcgcaagctt aatagctaat ttagcgatcc atttatttct tttactgagc ccagtaataa    15660
```

```
tttttatttc ttcttggtaa gttttttccct ttaatttagt agtgaactca tcgggatagc   15720
gaagaaaaat actattaatt tttaactcag ttacttgtcc atcttccatt aatttagagg   15780
tcgttactgg cttaaatatt tcaccgaaca ttccaacata ctgcattata ttagctttgc   15840
catcgcgcaa tgaaccagac aaaccaaatt taaacataca gttatttaaa cctgatatga   15900
tagatgaaat acttttttcct gtagcaagat ggcattcatc attcatcatc attccaaact   15960
gtgagaacca ttcttttggt tgttttacta cagtttgcca tgtaccaaca acgactggtg   16020
catcattttt atatttatca tcttttgatg ctccaccgcc aattttcttt atcattgcat   16080
gactgaataa acgatagtca acaaagtcat cagccatctg agttgtcaga gcagttgttg   16140
gaacaatgat aagaattttg ccttcataat tttccaaata ataccgagca agcaaagctt   16200
gaattaaaga tttacctgcg gatgttggaa gattaagaat tctacgacga ttaactaatc   16260
cttcgaacac tgcatctttt tgataccaat gcggttcaat tcttttatttt cctgaataga   16320
tttctaattt agaaagccat tcatcaaaat cttttcttga taattcttct ttttcgttaa   16380
tctgtgggtc aatccaggct ttataaccaa agttatcaca gaacttttta atttgcccga   16440
ctaagccgaa tggaagaagg cgattataat ctaaaagacg gattcgtcca tcccagttgc   16500
catatctgaa gcgaggatta aacctatatc catcggcctc aaacgaaaag aaatctctta   16560
attcgtggaa cgtgctctct tcacaatcga tgcgtacatg actaaagtcg tgaaaatgta   16620
ctttaatatc cataattatg ccttactaaa tttgccttta gagtctcttt tcatgagacg   16680
acctttaata aatccatcgg gaataataca gtctggttgt attaatttat ttattgctcc   16740
attattgacc caaaaagttc ctgtggtagt cggtttgact ttacatcctt ttctggactt   16800
tctattaaga tgaaccatcc cttttacaaa tccttctgga acaagttctc cgggtttaat   16860
aaaaatattt ttagttccat tggtgtaaca agttgtacct aataccgtgc ccggtgagtt   16920
ttcaaatctc ttagcggaag attctttcat ctttgctata acctctgcag tcataacaat   16980
tccaccaatt ccaccaggtt tcatattata ataattttttg ctttttatta gttcaggagt   17040
tataatttct tcttcataca tgtacgcttc ttcggaagtt ttaaactctt ttagtattgt   17100
tctagagaaa ttcttttcac catatttctt tatagcctgc tgaattgcct taccggaacc   17160
aaggtagcca tcattcaagt catcagtaga gtgttttcct atatacttttt taccatttat   17220
tagatttgtc gtttcatata caaagtgata catactatttt tccgagtaat aaatatatct   17280
atatttatac tgaggaaata ttatgataga taaagattat attgcagagc tgaaggctct   17340
tgatgataat aaagaagcta aagctaaatt agctgaatat gctgaacagt ttggtataaa   17400
agtcaaaaag aataaatctt ttgataatat cgttaatgat attgaagaag ccctccagaa   17460
gctcgctagt gaacctatgc cagagactga tgggttatct attaaagact taattgatgc   17520
tgctgatgct gcagacggat taaaatatga cgatgaagaa gtcaatccag aggcagcact   17580
tctgattgat tctccggtta aatctgacat taaaattgaa gtagtagaaa cggataaaat   17640
tcctgaaaat accgatgttt tgattgaaga tactcctttt gttgaagaaa aattcgaaca   17700
ggctgtagct gagattattg aatctgagaa gccgtctgta tttactcttc cggaaaactt   17760
tagtccgaat cttcagctga ttggaaaaaa tccaggattc tgcactgttc cttggtggat   17820
ttaccagtgg attgctgaaa ctccggattg gaaatctcac ccaactagtt ttgagcatgc   17880
gtcagcacac caaactttat ttagcttaat ttattacatt aatcgcgacg gatcagttct   17940
aattcgtgaa acacgtaatt cttctttcgt aacattaaaa taaggataac ttatggcttt   18000
tacagttgat ataactccta aaacacctac tggagttata gatcagactc agcagtttac   18060
```

```
tgctacaccc agtggtcaaa ctggaggtgg aactattacc tatgcttgga gtgtagataa   18120
tgctccgcaa gaaggatcag cggcaacttt tgattatgta ttaaaaggac ctgccggtca   18180
aaagactatt aaagtcgttg caacaaatac agttccagaa tctgaatctg aacctgaaac   18240
agcagaagct acgacaacta tcacagttca aaataagaca cagacaacta ccttagctgt   18300
aactcctggt agccctgatg ctggagtgat tggaactcca attgaattta ctgctgcctt   18360
agcttcacag ccatcaggtg caaacgctac atatcaatgg tacgttgacg gttctcctgc   18420
gggcgaagca actggcacta cattcaatta cactcctgac gcaagcggag ttaaaacaat   18480
taagtgtgta gctcaagtaa ccgcgacaga ttatgatgca aaggaagtta cttctaatga   18540
agtgtcactg actgttaata aaagacgca gacaactacc ttggcagtaa ctcctgatag   18600
tcctccagca ggagttattg aacagccgt tgaatttact gctgccttag tttctcaacc   18660
cgttggagcg tctgctacat atcaatggta tgtagatgat tctcaaattg gtgaagaaac   18720
taactctaca tttaactata ctccaactac aagtggagta aaaagaatta aatgcgtagc   18780
ccaagtaaca gcaacagatt atgacgcaaa aacagttact tctaatgaag tatcattaac   18840
agttaataag aagacacaga caactacgtt agccgtaact cctgctaatc ctgccgccgg   18900
ggtaattgga accccagttc aatttactgc tgccttggct tcacagccac cgggagcgtc   18960
tgctacgtat cagtggtatg ttgacagttc tctggtcgat ggagaaacta ctactacatt   19020
taactatact cctaccacag ttggagctaa acagttaag tgtgtagcgc aagtaactgc   19080
agaaaattac aatgaaaagg aagttacttc taatgaagta tcattaacag ttaataagaa   19140
gacaatgaat ccacaggtta cattgactcc tccttctatt aacgttcagc aagatgcttc   19200
ggctacattt actgctaatg ttactgatgc tccagaagaa gctcaaattg aatattcatg   19260
gaagaaagat tcttctccag tagaagggtc aactaatgta tacaccgttg atacatcatc   19320
tattggaagt caaactattg aagttactgc aactgttact gctactgatt atgatagcaa   19380
aactatcaca gcagaaggtc aagttcaggt aactgataaa gttgctccag aaccagaagg   19440
tgaattgcct tatgttcatc ctcttccaca tcgtacttcg gcttatatct ggtgcggttg   19500
gtgggttatg gatgaaatcc aaaaatgac cgaagaaggt aaagattgga aaactgaaga   19560
tccagatagt aaatactacc tgcatcgtta cactcttcag aagatgatga aagactatcc   19620
agaagttgat gttcaagaat cacgtaatgg atacatcatt cataaaactg ctttagaaac   19680
tggtatcatc tatacctatc cataatcata aggggcttcg gcccctttct tcattttgaa   19740
agcacacaaa acacactcag aaaatgatgt atataatggc accaactcga taacatgaga   19800
ttgattatga gaactgaggt tgtggtgttt actcttcatg agtctggaaa gtcattcatt   19860
gaaattgctc gtgaattgaa cttacaggca aaggaagtgg ctgtattatg ggctcgagct   19920
atgactgcta gaataaaatt tgaaactcga gaaaagttg tctatagaaa aaggcatatt   19980
aataaaaagg tgaaaaatgg aacagtatga tcttatgaa aatgaatctt ttgctaatca   20040
attacgtgaa aaagcactta aaagtaaaca gtttaagtta gagtgtttta ttaaagattt   20100
ttcggaactt gctaataaag cagctgaaca aggtaaaaca tattttagtt attattgtac   20160
tgctcgcgat aaattgatta ctgaagaaat tggtgattgg ctgagaaaag aaggatttag   20220
ctttaaagtc aatagtgatc agcgtgatgg tgattggtta gaaattacat tttgaggatt   20280
aattatgttt aaaagtata gcagtcttga aaatcattac aattctaaat tcattgaaaa   20340
actttacagt ttaggattga ctggcggcga atgggtagct cgcgaaaaga ttcatggcac   20400
```

```
aaatttctca ttgattattg agcgtgataa agtaacttgt gctaaacgaa ctggtcctat   20460
tcttcctgct gaagatttct ttgggtatga aattattttg aagaattacg ctgattccat   20520
taaagcagta caagatatta tggaaacttc agcggttgta tcttatcaag ttttttggcga   20580 attcgctgga cctggcattc agaagaatgt cgattatggc gataaagatt tttatgtatt   20640
tgacattatt gttactacag aaagtggtga tgtgacttat gtcgatgatt atatgatgga   20700
atcattctgt aatacattta aatttaaaat ggctccactt ttaggtcgtg gtaaatttga   20760
agagctgatt aaattgccaa atgatttaga ttctgtcgta caggattata attttacggt   20820
agaccatgct ggattagttg atgcaaataa atgcgtttgg aatgctgaag caaaaggcga   20880
agtatttacc gctgaaggat atgtattgaa accttgttat ccttcttggc tgcctaatcg   20940
caatcgtgta gccatcaaat gcaagaactc taaatttagt gaaaagaaaa agtctgataa   21000
gcctattaaa gctaaagttg agttgtcaga agctgataat aaattgctgg gaattttagc   21060
ttgttatgtt acactgaacc gagtaaataa cgttatttct aaaattggtg aaattggtcc   21120
aaaagatttt ggaaaggtga tgggactaac tgttcaagat attttggaag aaacttctcg   21180
tgaaggtatt actctaactc aagcggataa tccttctttg attaagaagg aattagttaa   21240
aatggtacaa gatgtacttc gtccggcttg gattgaattg gtaagttaaa taaaagggaa   21300
ccgaaagggg tccctttgtt ttattcatca atgataattt ttggtagctt aacacctaat   21360
aaaacagaca aatctgaacg acccgccatt ttatccatgt ctccaccgtc aattactctt   21420
gcttcttttt catcttttgc tacagtgtaa ggatttgcag ataaagcata tctaactaat   21480
aaaccgatag atggctgcaa actttctgga tcaactacaa ctttaaatgc acctacatgt   21540
tcagggtcat ctaagtcaag gccttctgta tacggagcat agaaaattga tccaacaatt   21600 tcttttttcac caatatttttc tactacaccc acgattacat aatccaatgg gctgttggta   21660
tcgcaataaa gcggtaaacc attagctaag aacccgtagg cattttgtga agatatttg    21720 tcatcttctg gtttatgttt taaccaacct gatgcagcaa gaatcgcagc ggcgcgagct   21780
gaagcaacac agaacgttgc tgtataagtt gattcttcct ggatatgtga accatttca    21840 cacaccattc ggtataatga acgaccagct tcaggtgcag atgcataact caaatcaatg   21900
aatccagtat cagtaattcc tgtaacttta tagcgttttg atactgtaat caaagactgt   21960
agaatatctt tattgattc atccgccatt tcggttgcaa gcaaatcttc caagaaatta    22020
ggagcatcga atccatttgc ttctaaatct tgtgctaatt caactgtgat gccagtttta   22080
agtttacgag atttaactgc ggtttgccat ttattaatct ggaatctagc atccgcaatt   22140
tcactatcag agctttcaaa tttacttgtt actgcagcat cagaaaatag acgaaccttt   22200
aaaagaacga ttgcaatctg aagagctaat tctaaatcgc tttcttcaat atcagcaaat   22260
ggtgtatctt ctaatacttt ataaacgata ttattatatt tgaataaatc gcctttattg   22320
agagttaatt tagactcttc tgttaattct gtgatttgtt ctcggtctac atacccagct   22380
tcgccggcgt aagtagcacc agttttaaat gtaaattcgt tatctgggtt aaggtatttg   22440
ataccataaa aagcagcaac aggttgatta gttcttgcg ttgctacaat gtcagaatat    22500
attaatttag tggtagcgcg agtcaaagca acgagatttg ggcgaccgat tgagttgcta   22560
ttcgttgtgg ttgattcgcg cagaagttcg ttgattttag ccattgcgct ttccttttgg   22620
tttatatgat ttatttatac cataaaaaca actaaaggga cccgaaggtc ccttaaatcg   22680
tcaaagatta gatacctttta acatatacac ggcggaagta agcgttttta ccaaggctat   22740
tcagaataga aggcataccg ctctggatgc gagaagccgg agcctgagca gcggattctg   22800
```

```
caaatgggtt gataccgata ccgtaacgag ttttgaatcc cattactggt tggaagttct    22860
tcggatcgga accacgcagc ggagtcagag ctacatatgg agcgtagtaa ataccagcat    22920
ccatttcgtt cggacccttta taacctacag tgaaataatc ctgtttagca tactggtcga    22980
tatatacacg gtatttacca cccagaacac cagcaaatac tgacttggta gtatcagtgt    23040
taaagccggt agccagaccc tgtgcagcat aagaaatgcc agtatcaact gaagccagaa    23100
cgttaactac gttacgggaa gcgataatga agttaccttc accacgaccg gtctgacgag    23160
caatttcaac tgcttctttg tcaatctgga acaacagagc tttaaaggat tcacccgccc    23220
agcgagcacc acgaatatca atcggatcct ggaagtcaaa tacaccagct ttagaacccg    23280
gagtcagggt cataccagat ttaccaacct gagctgagta gttaatccaa tcaacaactt    23340
cacggttgat ttccaacatg atttcggtag ccagaatacc agacagttca gcatcagcat    23400
ccataccgtg aacagcgcgg aggtcttgtg ctaattcgat agagtaagca gctttcagct    23460
gacgagattt agcttcgata acttgtttat cgatacggaa gcccatttca ttccatgggt    23520
tatcggttga accgttgaaa ccttcctgaa gttcagcgat agaagtagcc ataccttcag    23580
cgatttctac cagtacacca gcttccattt gtttcttaat ttcagcatct aatttagcag    23640
cgtcagttgc gcttgcacta attgttactt gagcagaagc ttgcagatac acagtaccag    23700
tgtcctggaa gaagtgagta tagatatcac ctactgtggt ttgtgtgcta gcagccagag    23760
ctgtgaattt cttagcagca ccctgaccag agaacattgc atctggacca tacattgggt    23820
ggaatgcttc tttagcgcca gcagcgattg ggtctttacc atatactgca cgcagtgcga    23880
atacctggcc agtcgggctg ttcatcggct gaacaccgca aatatcgaaa gcaatcaggt    23940
taggaatagc acgacgtacc atacccataa cagctgggcc aatctgagtt actgcgccag    24000
aagtttgacc agcagcgatg ttagtagcgt tgtaaccgtg gtcaccaccg atttcagctt    24060
ctgttaagaa agaaccgaac gcctgagcga ttttttcgtc tttgtattct ggagctgtct    24120
ggaaatcttt ttcctggttt tcaaagattt tagcgataat cgcttgtttg ctattagcaa    24180
tttccggtaa accttcacct tccagtaatg gcttccattt gttcaaaagt tcagctttag    24240
ttttgatagt catttgtgtt aacctttaaa attagaaacg agatgcgact ttcgcatata    24300
cacttacaat atcttctgca ccaggtgcag ctttatcttc tacagcttca gtgacgaaat    24360
tcagtccggc tgcttcagta tcaggagtat ttataccctc agtaatagtg ctttcatctt    24420
tattagactt cttccaccatt tctacgatgg cactcaattt acttgagaat gcatctgaat    24480
aatccatacc ttcgaccaga gcagagactt tttcttttg agactcagtc agatctttag    24540
tactttcgct caatgccact tcacgctgca cataattgat atatgcgtcg cgcatattga    24600
gttcttcgaa cagacgagct gattcttctt tatgttcttg cagctcttct tccatttcag    24660
ctacaacatc aactgattct tctggaacaa cgacgttgtg ttcaacaaag agctcttta    24720 atccaccaag catggattca aacagttcgg ctttgatgcc tttatcaact gctaatttat    24780
tttcagcgag ccattctttc gcaagatggt cgatgaattt agaagcttgc tcagcgattt    24840
tcttctcagc tttttcttcg gcttcttctt tatttttttc tacttcttct tctgcttttt    24900 cagcaattt agcgatatga gattcagcta atttaacggc gtgctgcttg acggtagctt    24960
cgaatacagt gccgaaagtt tcttttgctt ccggagaaat attaactgat tcgaaaatac    25020
tatcaagagc aacggaagca tcaattttt gcgcttcagc aatcagttgt tctttaagca    25080
ttttgtagtc ctgttgttta gataataata tttataacgc ttttttcatg gcctctgcga    25140
```

```
gagccatata ggcgtcatcg gcacttgtat cggcttccgc cgtctgtgat tcggtaattt   25200
ccttaggagt tacccatgca tctggagcac ttggacccca tactgcatca acacctacag   25260
ttaatttgaa tccttcgttt acgatacgat aacctttatt tgtgtcagtc aatgaaccta   25320
atccacgaga agaaactcct ggaatccatc cggcacgaat attagctgct aatttatctc   25380
caggaccatg gtcaccttca ataacacgag ctcgtccgta tacgtcattt cctttccacc   25440
acatatcttc tataatgata gcggcttgca tcgggtcaac attagcgcgt ggaggatgat   25500
ttaattctcc gagagcttgt ttagttaaaa cttgctcatt gatatagtct tttaccgctt   25560
tttctaatat gcgttttgga taaagacgtt tatttctatt gacgacttcc gcttgcatga   25620
atattccttc gatgtataaa ccaggtttta aaccgaggtc ttttccatca tgagattcaa   25680
gcattggcac gccatcaata atttcgccag gttgacccca gtttcaatt agtaattggg   25740 gttcattcat tagcttaatc ctaatgcttt acggcgttta agagcttttt tacgcttacg   25800
ctgagcacga gattgacctg ctgggttggc aatcttcgtt ttggtagctt tgcgagcaat   25860
ttgtctacgt tttgctttag acagcccggt ggtttgaaat gcattacgtt cacgcgtctt   25920
gcggtcttta gtacgtgtaa tttcaccacg agcagaaaca tgtttaacga tgaattcatt   25980
tagcggcatg tcttcattaa tagaagctaa tgcaattgct aaatcagttt catcatcaag   26040
catattctcg acaattgtat ttatatcgtc tttatttaaa gcagaagaca attcgtcaaa   26100
gcgaccctgt gcttcaggaa taagtgcttc gacattctcg agaactaatt catgagtttc   26160
agggatcaga agcattattc atcatcctcg tcttcgtcat cttcgtcaga gtctttgtct   26220
tttttgtcgt ctttatcatc gctatcttca tcatcctcgt cttcgtcatc atcctcatca   26280
tcaggttctt caccttcgat taagaaattg cgagcgatag cgattttttc ttctttaatt   26340
aaatcaatcg ttcttgcagc catggcttca gcaaagaatt tacgagcggc tacgaggtcg   26400
tttgatttaa tagcttcaat taaaccttcc attaaaaatc ctcttgttct tggtcggggt   26460
cttggaaacg agcctcttta gactcttctt caatttgctt ggcttcttgt tctatttctt   26520
catcagtcat ctgcaaaata tctttcatag cagttctgtg agaaatatat ttaccaataa   26580
atggttctgc catggttagc atattaattc ttcgttccaa aatttctgct tctttgagtt   26640
cagtaaagta gctatcccga tgaaattcta tcttaatatt atttatttca tcattccact   26700
catcttctgt gattatacct ttaagcaaca gatttgtttt aagcggatct aggaaaactt   26760
cttcaaactt gtgctgtaac tcacgaataa atttagcaaa cgttaattca tcacgtgtaa   26820
tgctagttcc agaatcaaac atcacaccgc cttgttggtc ttgcgggatg cgtgaaagag   26880
gaacacgtaa tgccatataa agagcttgtc taaaccaacg aacatcttcc atattaccag   26940
tattatcggc accaggaaga gtatcaactt ctgtcacagc tttaccatcg cggcgctgta   27000
accaatagtc ttcggtcata gacatattat gctgttgatt ttttatttta ccggtcgatg   27060
cgtcatatac tacacggttt ttcatcgtgt tcatgacatg ttgcatgtgc tcggcagctt   27120
tacgagcagg catattacct gtgtctacat accaaacacg acggtcagga gcacgagtaa   27180
tacgataaat gacaacagca tcttctaata attttaattg gttagcaggt ttaacagcac   27240
gatgcaaata cccgatgata ttttaccac agcaatcgac taatccagaa tgggcataaa   27300
cgatggcagc tttaggaatt tttatttttg tgccagcttc atacattcta ccatcacatg   27360
catatgattc gtgcgcagta tcatatataa aatactcttt gtaacctta actattttg   27420 tgccagcttc agtttctgtt ataatttcac gaacatactg aacttgacga gggtctaatc   27480
tacgtaattc ctttatgcct tcttttggac gttttggatc aataatttta tgaaagaaaa   27540
```

```
ttcttgaatc tacataccaa cgtctaaaat gatcagaacc ttttcgttga aacgatagat   27600
gatttaacac atcgctaaat tcatctaaca tcatatttt  aattttt gga ctaaatttag  27660 atttatccaa atttaacgct acgacttcag tatcatcttc atagacgata gcgtctgaaa   27720
cgatttctga aactgcatta tctacttcat agttattcat gagattacga tatgtatcaa   27780
taagctcacg agtagttttc attcctggtt catatgaacc aaaaattgtt tggaatgcag   27840
cattataagg agaagcagct tcgttcgagc ttacttcaaa ttctcttgct ccatcatcaa   27900
gctttggggc tgtaatggaa acaagatctt ctttttcttg gtctttaaaa tttcgttcgt   27960
ccattttagc ccatggagca aacaaactta atacattaaa tttcattgta ttctccaaat   28020
gggaattata gttatattta taatggactt ctctgcttta agcaggatgg ggatttctcc   28080
ccattcattt tattcccaat aatcgagagc aagagttact tcaaaagttt ggatttcatt   28140
gtttgaatcc caatctaatt gaagttcacc cacgttagta ggccacaggc ctttaatttc   28200
gacttctttt gttacggttt tagcgtcacg agcatattgg cgaacaacag cgctcttttt   28260
atattctgct ggttttccac cagtaatttc gttccttgc  ccagcagcaa tgctttgcca   28320
atcaacaaac ttctggcgag catcatgtgc ctcatcgttc attactgtaa cagtccagtc   28380
atcgaatgta cgatcgcctg ctacgttaat tttacggttc ataaatccga ctggaatttt   28440
ttctacaata ccagctggta aagcagtggc tttacattga aacgtaaaat tttgtccaag   28500
ataagaaatt tctacttgga ataagttagg tcgagcaaaa tcaccagatt caaacgctcg   28560
tgttacatca tctacaaaca tattagcctc tgtagtattt atatccctat gtttaaccta   28620
gggcatatag aattaaagaa ttaaggatat agtgtattta tatggcctgc cgaaacaggc   28680
ctttagaatc attctagtaa atcccaaaga tctacactat ttcttttga  cttttctcgg   28740 ttagattccc aagtgattat ttctaaatta ttaataccgc caattatttt agcaggaatt   28800
aaattatcaa aaccgtattt gatagatacc ttgtgatcaa gttggtaagc accttctgta   28860
ccacacactc ctatcttatc agcattcggc cattttgacc aaattttctt atgcttacga   28920
gtttctttat ataccaatga aatatattca cgcatttcag atttatttgg gttccatctt   28980
ggatgattta cgccatgcat acattctact gttttttcctt tattcgcgga accatatgaa   29040
ttattgcgca ttttatcttt atgacggcaa tcacgacaaa tatcagtgtt tcttccaatg   29100
cgttggttat attcaattcc acattatcg caacggcatt ttacatacgc ggtactacct    29160
ttaatgtctt caactttaac atcaatttca taatacataa atccatgttt aaccgctcca   29220
agaggtgtta atttataacc ctttgattga taatgtttaa aatttgacgg tacaattttc   29280
actttaacaa acttagaaat aatcacttgt ttcctcgaga ataggggccg aagccccata   29340
atcaattaac ctgcaagacc agttaactca tcgaaatctg caccagtagc agttgcgacg   29400
aaattcaaag taatataatt tatactgcgc gccggttgga tgtagaatgt tgcaacaaac   29460
tcatttctat caattactga cggagtgtta tttgttgtat cgcaaactac acgatattca   29520
taaattccac cgagagcttt aattccctgc aagtactggg aagtttctgt gcggaacgat   29580
gaacgagtaa acgcgttgtt taattcgaac aaacgatatt ttgaactacg tccgatattc   29640
gttttcaaca tattaaacag acgacgaacg ttaatacgat caaatggaga aggaacagaa   29700
gtagctgttt tatcaccata caatacgtaa ccatcaccac ctgtaccagt tactgggttg   29760
atagcttctt ggtataaacg gtcgcgctga gcttggcgag tttcaatagc aagtttaata   29820
acgttaagaa tctggccacg attataacca gctggagaca tccaagtctg agaaacgtta   29880
```

```
tcagttctcg cgcataaacc agcaatatca gctgctaatg gaacccaacg atttacatca    29940
ttatatttgt catactgata cttgtagtta ccatcaattg ctgcgtaggt tgaactgata    30000
ttaaagttat tatcagtgta tgaacctgct gcagttctcc aattgactaa gttatcaaca    30060
gcacgagtta caggaattcc aactacagtt tcacgcggtg gcgagcacag tactaagcaa    30120
tcttggcgag catccccaat tgaaacgacg tgttttttgga cagtagatgc tgtttctaaa    30180
gattcaccgg cacaagaacc cgcaataaac aactgaacat caacagattc acggtcagca    30240
aagaagtccc aagcttccat caaatctcct gctgttactt cagcatttga tgataatcca    30300
ccagacagag ttaaaattcc agagaagcct tctggccagt tttgtgcagt tgcgaaaata    30360
tattctgaac cacctttttgc gaaaaagtcg tcaatataga tgttactatc gtaaatatct    30420
ttttcacctc gctttgtcga aagaacaacg ctttgaacaa tagcatcatt gcgacgaact    30480
atgatagcgt attgtgaatc agtttgtggt ccatatccaa acactgcttt ggcagtagat    30540
gcgcgtgttc cgccacctgg ataaattgga agtaatgcag aagcaccttt tgcgtagtca    30600
gctttagata cgatttcaat ttcgattttta tcgcccaact cgcccggata aagagctact    30660
actcctggaa ttccatattt ttcgagattt gcctgaaagt caacagctgt catagcagct    30720
tcggcatttt caatttcagc taataaaata ccagaatcag taataatttt tccaagagtt    30780
attactgcgg ctaaaccaga ggaagacgaa gaaatttccg cggtccagtt agaacctaat    30840
gctggatatt cgcctacttc tttcgcttta gcgataattt ttgcggtagg aatattaatt    30900
ttcttaattt ttccatcagc atctacttcg gtaactttac attctgtttc aatgtcttct    30960
gaaacatact taaccgtgat tttatctcca accgcgtagt tactacctgg ggtagaaata    31020
gtgtattcaa tattaccggc aatcggagat gagtttttag cggtatctct atcgacagca    31080
cgcacaactc gcaaatcatt tccgtattgt aagaaattca ttgcagacat aaaatagtca    31140
gcagtttcag ctgtaggttg accaaaagta ttaactaaat ctacttcatt tgtaacctgt    31200
ttaatttgaa aagcaggacc ccactggaat ttaccggcca aagctgctgt accagtagag    31260
ttattaacca cggtgctttg aaccgtagtt tctttgagct caatgcccgg agataataaa    31320
gtcatttttta atcctctttta atatgcttta atatatttat accattgaca taccatgaga    31380
tactggaaca tactcagcag aatgaaccga atcaacaaat atgactggag cgtattcatc    31440
acccatatct tggagttctt ttgaaaacac ttcagatgct agtcgcatgt catctttgtc    31500
agcataatca ataaattttg attgtgttga taaccatcca aaaattacta aagacattac    31560
taaatcgtca tgataacctt cttcagccgc ccaagacacg cctttttcac taaacgttct    31620
aaactcttga atagttgcgc ggtgatgaat aataagctta tcttttttcaa taaggtcttt    31680
taatgtagag catcctactg cttttcgttcg tttagttttgc ttcattccta aatcagtata    31740
tgaatcgcaa ataacgcctt cgtattctaa atccatataa agtgatttcg caactgacac    31800
accagtacta tttaattcaa tataaactgg gcattcatta tattctacta aataacgcat    31860
aacgatgtcg ggtagaatta aatgagaaat agtgtttgag tgtaaaacac caacttgttc    31920
ccacacatca tcggtaacat caataatatg taaagcgtgg taatcttgcc cacgaccttc    31980
tgagcagtct agagttgcaa tatattttct atctggttca gggcttttaa atcgatgaaa    32040
accatgatca tctggagtta cttcaatgaa atccataaca gccaatttca ttcctgaaat    32100
taatgtacca gaagtccctt caaacgccgc agtgtgttct tgacgaaatt gagctaaagt    32160
agaaccatta atggtttgta tgctccattg ccatccatcg tcaaaaatat cttcatcgtt    32220
ataaagacgt tctttaactg aattccaaat agcagtgtat ggttcaaacc ctgatttacc    32280
```

```
ttcaacagca gcagtccaaa tatcataaaa atgatttaat ccattaggag tcgtagtaat   32340
aataattttc gaacgacgac cagatgaaat tactggctga atagcaagcc aggaatcatg   32400
gaagtttgga ataaatgcgc attcgtcgat ataaatcatt gcgaacgagt taccacgaac   32460
tgcgtcagga gaggaagcat aggctccgat tgaggaacca ttatcaagtt caatagaccc   32520
tttattccat tcaacaattc ctggctgtaa aaagtcagga agcagttcaa ttgcttgctt   32580
agtacgatct aaaacttccg cagacattga gcctttgtgc gcaagaatac ctacagcttt   32640
atccttatta aagcatacaa agtgtgcaag aaaaatagct actacagttg ttttaccaag   32700
ctgacgtgat aaattacaaa cagtcatacg tttagatgac attattttga gcatatcacg   32760
ctgatagtca cgtaattgaa cctttatgac accatagtca atatgagtaa tggcgcagta   32820
tgtttctgca aaatacacaa tatcgtctcg gcattttttc cattcctcaa ccatttcacg   32880
agtccactgc gttttaatat tagctcgttt caagttagga agacccatat accgagatct   32940
tttattattc ttatctttat aagtttgaaa taattcaggc ttatcagaat tatttggaat   33000
ttttactatt ttgtgtagac gaagataatc actgaatttt tcaggatacc attttccatc   33060
ccactgtgat tttatccaat gaattccatc ttcatctttt ctttctgcta agctcgggtg   33120
ttttattaaa attttttccag cttcgtttaa cggatggaaa tcatttaatg cattaatcgg   33180
ttgttccatt tatcaccttc tcacgagctt cttgagcctc gtaagcatca ccaatttcgt   33240
ccattaattc tgttggtgaa cccatgaata ctgtcgcatt ctgaatattc atttgacctg   33300
taggaacagc gcctttggtg ccaacctgct cagatgtaat atctttcata tctttgtgaa   33360
gcttcagtat ttctctgttc gtcgtagtca tttgccccat aagagttgca aatacttcca   33420
tgtgacgagg agaatcagca ttctttgccg tctcaagaaa aatcttggct gcgtccatta   33480
gcatttgttg ttgaaaatgc atatttcgac gaactactcc ataatcatct tctaagtcag   33540
gagtacggtt ttgaggattg cttttaactt ctactaattg cagaggttca tatactttaa   33600
tttcctcccc gtcaattccg gggaggtcag aaatatctaa aagtttgttt atatcaagac   33660
cttccataat aacctctatg ttcttgggcc aggaggttct ggcggtgttg gtctatttac   33720
attgctagtg aaagtttgtt ttactgttcc atcccagtct tctgggttaa tatctcgagg   33780
aacaacttcg ctatctacag attcaaaaac accttcgcca tcaggcaaat ctcttgtatt   33840
ggcgtgaaaa tctgtataag tagtacgaat taatccttct gcatcatcta ctggaggata   33900
catccatcca tttacttcaa atgttagtga ccattcaatt ctacgacgag ataaattatc   33960
tccatctata gcttcatcta tagcagcaga catcagtaca attttaatat cccttttaaa   34020
tggaatatca tttccaaact gttcgtacat agttgtatta aaatgaggtt gaaaatatgg   34080
aagaatctgt tcaactattt gaaacatatc atcttcgtag cgagtaaaga tactcaattc   34140
ataaatcatt ttaataggag atggattata ttgtgatact acggaagttg cgccttttttg   34200 cagtaaattc tgatttaaaa tgtttgtttt aaatggagca ttatagctaa aatcaactaa   34260
atgtaaattt atacgaggta gaatagtttc aactttagct acatcttctt gcgaatttat   34320
cgatgtccat ttatttaatt tcatcatgaa gtgttccttt gatgcatacg taataggaac   34380
acgtataaac ttatcaccag attctaactg acgtttgatt tggatatttg aaaacaaatc   34440
gcccatcaag gtagcatatc gtctaaaaga cgaattataa aaataaccaa acatgatttc   34500
tcctaatctg ggcttaattt agtttataat atttattaat ccatgaaatc attatcaaat   34560
gggctagatt cgaaagattt gcctctatta ttgacaacaa cataaggttc aacatattct   34620
```

```
ttagcttcag aattaatttg atctacttca gcatactgat caatcttaat atcatgaatg   34680
ccattaagat tgcgaacagg atttaattct aattcactaa attctggaat gttaattcct   34740
tcattttcct gtagaactgg attaatttct tctccagaat aaatgaattt acctgctgta   34800
attttacgaa tagcgttttg gcctaattga taaaatggat catatggttc aacccagtta   34860
atttcgaata agctgttatc cataggaaaa tatattaaat ccccttcctt gggttctttt   34920
ccgttaactt ggtgtttaaa caaatttgga ttaatagaca aagttacttc atcctgtact   34980
tgcataccaa agttaccaaa gaatgattta gctccttcat atccttcaaa tgaatttaaa   35040
tatgcagcaa atttccaagc tttagtaaat ttattttttta ggtcttcgcc gaatatcaaa   35100
tcaggagaaa catactctct tggaacatag tagcattcta cacctcgcat ttgaatgctt   35160
tcagctacta atacatcagc taatatttgg ctgttttat aatgattgaa atttacataa   35220
ggatttagta tttcagtttc attagtctga gaataaccag tgcgattttc taatttagca   35280
aaaagatttt tatcataagt agccatatta acctaccaaa attccaaatg gaggatcgag   35340
caagtataat tcttcgcgta atgcttcttt ttctaatcga gcttcttcta ttaagcgttg   35400
tccatcaatt gtaacaccgc ctggaagcat catgccttgg tgacgtgcta aaatttggcc   35460
atttaattct ttagctaaag ctgtagcata gtctttcacc caacgattat tataagcacc   35520
ttgcttaaca tctgggtctt gacccacaac acgacctact aaattatggt ctggattatt   35580
atatcgttca gataatgacc aactatcttg cggaccaact gttccatatc ctactgtatt   35640
tccaaccatt ttgtttgtat caatgtatga tttagtccag ctttctacga taatcaaatc   35700 atattttgg aagtttccca tgactttgag ttgttcattt gctgaattga ccaaaagtc   35760 tggaatagga gaaagcatat cttgcatcat tcccatgtaa ctggtaagct gggtaaaata   35820 ccctaaaatca gctccaaagg cgtttggtcc ataaaatcta ttacaagaag tccccatgcc   35880
accattaata ccagccattc ctaaaagaaa gtcagtaaac catggatatg tagcgtttcc   35940
gtccattgac gttattgatc caacatttgt acgtaaaatt cgagttactg cgaatacgtt   36000
tgaacctctt aaatcgaaga ctccggtctt atatttttct tcgtcatctc ctacataaaa   36060
tacatgaaaa cctttgttaa gtccatcaaa atggtattca ccgtataatt ctagggcacg   36120
ctggatgcaa tcatagattt gatcgggtgt taactcaaca ttaataattg gagcccctaa   36180
acgtcttaga atgacatctt tgagttcctt tggattttga gaattatatc ctgcacttta   36240
aaaatccttt ggggccttgc ggccccatgt tatgctggtg ataaaaaggt agaaagtaat   36300
acccattcgc cgtctttacg aacgtaagct tgaccatctt ttggagcttc aggaatataa   36360
cctgcttcct gtaaagtctg aacatccgcc tgtaatgaag atacattact tttaatacta   36420
cgcatttctt gattaataga agaaatgtta gtttcattag cttttattga attagttaat   36480
ccacgctctt ctaccgttga accatttgga tttgttccat ttactaattt atttaatgtt   36540
acaacctgtc ctttaattcc agtagtgtta ttaccaattt caacttgcaa gttttgaaca   36600
tcattgttaa gtctattaac agaagtttca atagttgaaa ccctatttaa aagagaccca   36660
ggaggagaag gctgacctcc actagaatca gttccaacga tttgatttag ccatgaaacg   36720
tttgctcgta gtccagatga agtgttttca ccaacaattc catttaaaaa ctcaatagat   36780
gttgtattat ctttaatttt accttttaata ctagaaggaa tatcatctga gccaattgat   36840
gtttcaatga cagttaatcg ctgtttaaca cctccgcttt tatttagctc atcagttaaa   36900
gctgaaattt ctcgtgtatt agtgttaaca tctgtgatta ttgaagtatt tcctggatat   36960
ccaatagaag ttttgataga tttaatttcg gaattaagat taatttgtga ttgatctaaa   37020
```

```
ttatgcacac gtgaatatat actttcacta aatgaaggcg gtctttgtcc taattcctgt   37080
ctaagatttc ctacttcgat tgtaagcgaa cctacatcag attcaataaa ttttttcttcc  37140 aaatcactta gacgtattcc ttgggaagtt atagcatctg tattattaat gatacggtgc   37200
ttcatccccg tgctgctatt tcctacaaca ggaagaccat taatatcttg tccagcatat   37260
tgtcctagtt ccctttaat ccacagcaaa tcatttctaa tcgttctata aactgaattt    37320
gcttgcgaat taaatggacc aatatcagaa agaatattat caaccgtagt atttgtacca   37380
tttaatatat cagtatgttc acttgtgagc gtctttaaac ttgatatatc attttttatta 37440 acgctgatct gtgatagcgc ttctatatct cctgatacat ctaaaatacc ttgaatagtt   37500
ttaatatctt cctgagatgt ttcaatggca gttttaagaa ttcctacatt ttcgtcgaga   37560
acctcgacgt ttttaaacac ggaaacagtt ggtctattca ttgacccatc gtttccatac   37620
ttagtactag ctcctaatat ttcttcacca ttttaatcc atgaaatacg ttcctgacct    37680
tcgccaggaa cgctatcaac aaaaggtaac tcttttaatt caatcatttg taatccttag   37740
taatgaattt taataatata gtttaatgat atattccatg gtctagtttc ataaccaatt   37800
aatccttcac gattaagtgt accaaggggca tctctcggtc cacctaattc aaatccatca  37860
ttagtgaagt atgaagcgtt atcccagtcg gcatattttc tagttccaag atatccttga   37920
taaacggacg cgccaaatgg agcttcatgt ctttggtatt ctcccagcc accagcatgt    37980 ttatggtatg acatttgttg tgcttgaaca ccgccaacat gcattccgtc acatcctacg   38040
ccaagtctat cctttccata accatcttgt cctcgttgat ttaaaatatg acctcctgtg   38100
ccagctcctc tgacgaaaag acctcgcata tcaggaatgc cagggttatt ccaatcacca   38160
ccaaatcttg ttccaactgt gtttctataa tcaggatatt gatctcctga cacggttcca   38220
ccatggcaca taatccaacc tggaggtgca gaatcacccg caaacatcat aatagttcca   38280
actggaaccc tttcagacgc atatctttca gtggcaacag gttgatcacc attttttccac 38340 ataccgccgc gcgaccaaat tccatttgct gtaagatggt ctaaatttaa agaaccatta   38400
atagtttgtc caccgcgtgt attaattaca tctgcgttcc atgctaatgc tccagagcca   38460
tcaccctcgg gggcaatacc ggcttgcgtc gttaattta ctacaccgcg catagaacca    38520
gtagctcctc gaccatttaa tgtttcgcct gttactgcaa catctcctaa attactgtta   38580
atttccgatt gtgttcctaa acgtataaca cccttatatt cttgtgttgc aacagaattc   38640
ataaaggtat acggagaaat tgcatatcct tcgcggagag ttccttgacg agtttgcgca   38700
acagtagata attgaactac acctctcaca gattctgatg cagtatcttc ggaaggagct   38760
atttgtgaaa ttaattttat tgcaagtttt tgcgttttta atggagtcat tgccgtagta   38820
tcatcaactc cagctaaagc tgcaggtgta gatgatattt taataactcc atttgatgat   38880
tcagatgaat acctgttttg gaatacatcg tcagtatggt atttcaattt tgtggagtt   38940 atcgacgaat tattatctga gccttctaaa gtttcttcat ttgttgaata gcgtgttaaa  39000
ccatatttag tttcagtagc atttggatac aataatcttg ttgctaatgt agccggtgta   39060
acgattttag aattattagt tccatctaaa acctcttgct ctgacgcaat cattgctatt   39120
cctttaactt ccatagttgc atcaggaata ccatttacgc cgatattact tattttgat    39180 aatgcagact gcactgtcgt gacagtgtca ggaaaattcg atcctactgg atcgaattta   39240
acatattttg attcatttga tacgtgctga tatgtattgt tactcatgct attctctcaa   39300
aataataaaa tactgtaggt tgtgtgtgac tatctagcgt aacagtttgc gcacctaata   39360
```

| | |
|---|---|
| attgccaagt tccataccca ggtttagaag gagaaattat ttcttgtttg aaagtaattc | 39420 |
| ctttatcaga gtattgttct aagatatgtt cttgattatc taaatactta acttgtattt | 39480 |
| tatttcctat ggtaggatgg tcttcaaatg aatcaattgc aataaatttt gcaaccattt | 39540 |
| cctgcagagc tgttctaacg gcactggtaa attcgattga agtcattcca ttagtagctt | 39600 |
| taacaggaat gccaaacatg ttaacaataa ccgggtcacc tggtttggct gaagtatcag | 39660 |
| taacagttcc ttcaaatgac caatagtctg tttgctgcac gccagtagga gatacgccac | 39720 |
| ttatattaac taatacagct ccaacctgtt gctctgccat atttctaaca tcattaatag | 39780 |
| cagattctac atttgggtca taaaacccctt ttgctatttg tgaaattgtt acagcaccta | 39840 |
| ctggctgatt attcataacc gaaatatcat ttttcttagt tctaaaacca agaaaatctg | 39900 |
| ctaagcggga ataactcccc gctttattat taagtaaact cattatgcaa tccttatcca | 39960 |
| acgtataca gtaatagacg gttgaatatt actaatatta gcaggaggag tatgtgaaga | 40020 |
| gtttgttgtt gcgtaatctt cacgatattt tgtatatata ggaccagttt catctgggtc | 40080 |
| atattggcaa cctccaataa taaccgatcc attttcgtct tcaattaaaa ctctttcgtc | 40140 |
| ggttttagtt gcaggaagat ttgcgttttc aagcgttact gatgttgttc caaccgttcc | 40200 |
| acctgccgta tgtgaaggat ttccgctaga atctaaatca ttattgttta aagcaaagtt | 40260 |
| tggatccgta acatcatcat tccatcctac taaaacttgt cctttaccaa ataatttcca | 40320 |
| tgaaccaaat cccatataag tcaccggatt atttgggttt atagcatttt cataaattga | 40380 |
| accaacagga taaatgctgt cgaaaataga tgatattgaa ttatacgttc tagtataaga | 40440 |
| atcaacttt tcaacatttg gccaaccgat tttatcaaaa tctgttaagg ccacatcacc | 40500 |
| agtaacttca gtagatgatc ctttactaac ataacggtca tcagtcaatt caatgatgtc | 40560 |
| atcttttct aaaagagttc ctaaatcatt attgaaccat gttataacga taatgtcacc | 40620 |
| ggattcaaat tttctatcaa ataaaagact gataggtttt ccgtcttcat attctataga | 40680 |
| ataatcggtg tttgattctt tccattcgcc accaagagat atacatcctt cttgcgtatc | 40740 |
| tgaattagcg ccttcgcaca aaaacagagg atatccagct gttccagcct gctgctgtaa | 40800 |
| aattccatta aaacgaacct caagagagtt cggattaatt ggttcaccag gaattaatcc | 40860 |
| aaatgcagaa aatggaattg atttcatcgc cgataaatca gtaacataaa tgcttccttc | 40920 |
| taaagaagtc tttgatgtta gttttgaatc cagtactttt atttggcgtc ttgtatatga | 40980 |
| acttctccat tgtgatacac catccataaa tgtttcaatt tgaacagtgt caccaatatt | 41040 |
| acaaggctgt cttaatcgaa tattaaatcc atcaagagga actaattcgc cttcattttc | 41100 |
| gcccggagaa ccaaagtcac tgttttcgct aaatacatca ccgtaatata attcgttacc | 41160 |
| acgatgtttt actctgatgt tattgacatt ataactagtt ccacggaaaa tatctaaaaa | 41220 |
| gtcagtttgt ccttgaactt caactaaaaa ttctttacga gctacattac taatgtctga | 41280 |
| actgataatt ttgtcaattt gcttattttt gacatattcc cagcgtcctg gagcacaata | 41340 |
| aactaactcc aaatcactga attgaatatt aatttcaacc gatgatgacg acccttttaat | 41400 |
| tgtatcgcca gaagcagcta ctagtgtaac tggattaatg ttccatgttg caaatacatc | 41460 |
| cctagctcta attactttat tataatcatt aacagttcct ttaggaagtt gtagtgttac | 41520 |
| tctcccagac gaagtattaa tagcgtatga ttttccccat tctgccgtta gtgtttgccc | 41580 |
| agatgaagcg ttataagttt tccaggcacc ggctgaatat ggaacatcac catcaccgag | 41640 |
| ttcataataa agctcatcaa agttttcatt tattttata ccacctttac gcaggtagtc | 41700 |
| accggtacca tcatctacaa cattaccgat attaatatttt tgtttcatta ttgagccacc | 41760 |

```
ccgattttct gcgtagcgat aactttaact gctgctctca tgccaacaat agaagaactt   41820
acagtcgctg ttacataatt tgttttaata ctaaatgcaa tattagcgat ttcgtcttct   41880
tcggtttcat ttccaacccg catgacagca tattcagaag aaattacctc tgaattaaca   41940
gtatctacaa gaatatttat ttctgctgtt ttaattttc ttccatctac cgattggcat    42000
gtaactagca atttagccat attgtattca gtacgatgaa atagtggaat atcaactgac   42060
ccggatgtag aaatattcca tgtaccttca gctggcgatt ccttttggcc aaacatactt   42120
tcaatagaat aattccaaac agacgtagaa ttatcagatg aaatacagcg taaagttact   42180
ttactatatg gactagttac tactaaatta cctgaaacac ctttttattga atcaatcgct   42240 tgaatcgtta aaggattagt aactgatata gatccatttg agttaataaa ttcaacgcag   42300
tcaccaagtt cgcctctttc aatgataact ttaacaccta cagtagaggt atcaatatca   42360
tgcctagtac caacttttac tggagttgcg tactctgcaa tagagtgttt ttgataatat   42420
ccagtagcat gaataatttg gccatctgct ccagtgccat ttgctactgc cattttacgt   42480
tgatcgccaa acgcattata aattgcgtta aaatcactat taattttatt accaccgtcg   42540
aataagatat caccagtaga agcgttacca atttcgccgg tatcaatcaa tttctttggt   42600
tcttgaatga acatagcggt ttccttatga gtttatagta tttataaaga aaaagggagc   42660
ccatgggctc ccttaattta aaatgtaaac agaatattga tttcttctgt ttgatccatt   42720
gccatgataa taggtggcct attttccata taaatcattt cgcccgaatg cctcattaaa   42780
tcttccggat cataataatc cttttcagct ttaacgtttg ggtcatttgg atgaacttta   42840
gcttcaagag gattggtgat tattgatatt tgtctaaatc ctttatttcc tggtaatgca   42900
gcatcaggaa agtaaactga atctaaatat gctttaaaac ggatagtatt tgccttaaca   42960
cggtaaatta atccaaaatc atcttgttgc caagtgagat tatcttcata cccccatcta   43020
gccgggtctt cttttaattc ctcaggccaa ggaactacga tatattcatt cgtgcatcta   43080
tttatagata catcaggcgg aatctcaaaa agatattccc aaacataacc gtcgccgggt   43140
tcgattgttc cttcagcgtc tcctcgacct tcaggaggag tcattgacct aacagaagga   43200
gtccattttc cacctaactt aagacattca tccttattag ttaaagatgc tattgaacac   43260
gttccggtat caggaacatc taaacaacga tatactaacc agcctgcgcc tgattcagta   43320
gcattgtaag gagctgagtt acacactaca atatcgttaa ttctaaatgt gtatggatcc   43380
ggatatctag tatctcccca atctctacga ggaataactg catcaagcat agatggaaga   43440 accttacgg ttcccatcat atgagtccac atgtcagtta cacccaatac agaatcagtt    43500
ggataaggtg gagcaaagcc cacctcattt tcatttgatg accacggttc tgatcttcca   43560
aatgtgataa agatagtgtt tttatccgga ccacttccaa ttgaattata aaaattcaac   43620 atttttctg ttctaaattt tgaagtaact atcgcacgat agataacact tgaatcattc    43680
atctatttta acctgtgttg gattttcagg gtctcttgga tttcctatat tatctttag    43740 acgtttatta actaaatctc taaattgcgc aaacgttgtt ccagatgcgt caaatagagg   43800
actcattaat ttgcgtcgtt cagaaggcaa ttgaccttga aatattgaat tgttattttc   43860
agtattatag tcatcaggaa gaggatattc tacaccagcc attgggccag gctcataaat   43920
tgcttcgcct gttaccgaat catgctcaat ttcaccagtc ggagtcaatt tagctactct   43980
atcagcatat tcagtaggca atccagaatc ccatttgtag ttttttgtatt tattaattat   44040 agtctctgta tgtttaagag ttaaaccaac attaataaac atcgttaaaa gggtaattgc   44100
```

```
tataaatcca aatcctactg gatgaacaaa acgaataacg tcagatttcc agcgggaaga   44160
aggcaaattg gatttaattt tcattacata atatgatcga cttctattaa tatagtctat   44220
attattttga agcaaatcct ttcctttaac tccacgaata atttcgcctt caaaactagg   44280
aagtctttct gctttaactt cttgaccagc aattaatctt cccaaaagat tatgaatagt   44340
tacggtccat tgcaatttac cattagaata gcttctttct atataagtaa cattacatct   44400
tcctgtagct gtataaatcg tttgtcctac taagtcttcg gtcaaagaat cagattgaac   44460
gattatatca tattcagtac cagccccaga ttcgatttca atttcaactt cttcattata   44520
aagaacttta aaagaaatt tgtatgatgc ttcaattcct ttagtagaat aaaaatcata   44580
gctgcgtgat tcgaaaaatc ttgcgacagc atcacgtttg tcagcattta aataaatgtt   44640
tcttttatat atctctgacc acaaatattc ccatgcatgc tcttctcgtg gatatttgtt   44700
acgaattaaa tttcgtaaat tgttatactg agttccatat ccatcagaaa gatattgaat   44760
atatgcttcg caaatgctt caaaattcga atcctgcaac aaataagaat caggcatcat   44820
tgtgccaatt aatggtctta aatcagggtc agctaatcca cgctcttctt caggcgacca   44880
aggagtttca tgttcttggt tttgtaaaaa tgcctttaaa aatactccag ttggcttcca   44940
aataatttct actgtatctc taacacgata attaaaatca tagtaagaaa ttatttcacc   45000
ggaggattta taaaaaagca tcccagatgc atattttta aatccagtga atttaacatt   45060
tggcattact atagtgcaat cgccgtcatc ccagtattca tgaactaatc tatctggaga   45120
tgtttctgga aaattttcaa taactttagt gtattttaaa tcagcataaa ctactacaac   45180
tctatcagag ttgtttatcc aacatcgtgt gttagatttt ttagaccaat taagaatgg   45240 ttctgcatag tatttcattg gctgaggcgt aaaagtttcc caatcagatt tttcatctgc   45300
tataaatgcc atcatatgat aatgcttatc agctaaccat tcacgaggaa attcatattt   45360
aacggcaccg attaactggt attttgatgc agtttcaggg tcattaacaa tattatcact   45420
taaaaattta aaattactcg aagatagcga aactaattta ccgtcagttg acatattcgc   45480
ataccctggt tgaatacgtc ttctttcttc ttcagtattg ccaaaaactc ttttccacgt   45540
ttttgtgtca tgatttaaaa catatattcc tttatcagca gaatcaatta tttttgatgt   45600
tctaggatta gcatttaatg tttcaacttc accaataata agagcaaaaa ctttatcacc   45660
gatagaatcc attttatagc atactgcttt aggatttcca gttatagtca tagtatcagg   45720
ttcaaaaagc ctttccgaat atgttggaga taatggatca gaatctatag gtgcattact   45780 cgttttatg tatctaactt tgtctctggc gacaacgtaa atgtaatcat cggtgcaagt   45840
aatagcttct gcaatgcgat atacattcgc tggtaaagtc gcgtaagtgg caaaaatttc   45900
tacatcaaat cctaaatgta attgatcgcc aagtttagcg aatgttatat cctgcgaact   45960
aaatctgaca tcgtcagctg accatctgac atcagtagat ttgcggccat agaaaatctt   46020
gtcgtatcct agaacgtatg ttgtgttcgc agattggtaa tataccgtct tagataaagg   46080
atatcctaca cggtcattga agagctttac agctttccaa gtttgtcctt tatcattgga   46140
tactttaact acaggttgat agcgctcaaa aaggtataaa atcccttctg attccatcaa   46200
ataaactcgg ttaatatcct tacatacttg ctgaatagaa ccttgtattt catgatactc   46260
attttcacca ataataaaat tgcttattga tgaaacatca acatatgatg gactgaattg   46320
aaaagattca ttcatcaatg cagccattat agtgtcatta ttaaaattga cataaccaga   46380
attattaaga gtaaattttt cctgaatgaa tttattggct aattgcattt caatcatgtt   46440
ttgaaatgta taagcatttg tagcaaaagt ttcaaactct tcagtataaa tccaatcaga   46500
```

```
ctgctcaaaa tcttgtgcag ctgtagctac tctaataaca tatgatgtca atgggtcagc   46560
atcatcaaaa aagaagctgt tatttgcagt atatcctaag ttaatccatc tgtattgatt   46620
actcgggaga ttttcccccg agtttgtttt tgtctcagcg atttctacaa aatagtagaa   46680
attagcacca acgtcatccc agcgcacttg cacctgattt gcggataact tggaaattct   46740
gagactagtg actgaaggtg cttttactgt cattgtgata taggctccaa atcgatagtt   46800
aagtattgtg gacgtaagtc atttcaaat acaatcagcg aaccatcgcg agtaaagata    46860
acatcatcgg ttgggtcaga atataattca atagtctgaa cttcaaattt ttcagatgtt   46920
aaattaattt tagcgatatt ccaataaatc acatcagctg gataatttat ttcaccgata   46980
acatagtatt tgtcgcgtcc atcagaattt gctaatttgt taaaatcgtt gcctgaatat   47040
ggctgaatgt tttcattttc tgtaacatcg ccagaagcaa atggaccaat aataacttta   47100
ccaattcctt tagaatctcg gtctgttgat actatgcgaa cgtcatataa tacatcttct   47160
tctaaaccag tatcaggatt tacaaccttt cgtccagaat aaatgaaaaa cgtattagat   47220
tccatagaac gatctttat ttgattattg tatttaatac ctgcttcagg cgttttatag    47280
aagttttgta cttcacgaac aatttgaatt gtcgctgatg agccaatgat agaatgatct   47340
gcatcatcta catatgtcaa catcttagat ttagcgaaag atgagttaaa aatttctaca   47400
tcttcggtat aataacgatc aattttatca attatttgac cttcgagcca ctgttcggat   47460
tcttgcagct tatttaaagc atatgtgact tttaaattag tcttaataaa aagataatta   47520
ggagaaataa ttgacggtgt aataggagct aaattatagt ctttgagata atttttaata   47580
tcttcgcgct gtacggtagt taaatacaga cctgatttag gtttagcagc aataaatgca   47640
taaccaggtt tagtagaatc agtgaaagtc tgaactgctt gaataataga accaaatctc   47700
tctgaaacga atgtatcata gtcagtcgca gttacgcagc gttgctgggt ttcgcgttta   47760
atagtaccca attcgcgaat acgttcaata tcttctggat cgccgccgcc atctgcccca   47820
acaaaatctg ggtcatcgtt tggattttca ttaatgttga tgacagttat atttgtcaat   47880
gtatctgcgt atgaaaatcc gactgcacca ttcgcatctg caccgttagt actgatgtac   47940
tcaataacaa tcgtagagtt ctgggtaggt ttaagacctc caatataatt agcagtcaat   48000
gctccttctg ccgcattaac agaaatctcg ccttcaccaa aataaaactc agtattccca   48060
tcaatagttt cacgcatgta gtaaattgtt gatgtagaac cagcatgaac cattgacttt   48120
cttgtccagt taatccattc tgctccatca acgtatagtt taacttgatt tctatctata   48180
tttttgtcat aaatgataat aggtgttaat ttatcataga tgatttcagt tcttactata   48240
cgcccctggg ctaattttaa acgcggaaaa tattggttat ttttatcacg aatagcaata   48300
acatcttcgg tagatacaaa gttgtaagga ttaacgaaag tatcctttgc atatgctaaa   48360
aagcgagtac cacgaggaat agtaatgtaa tttctattca atgcgtctgt gcaagttagc   48420
ataatttcag tttgagcagc tgattttgaa gtaggtaaat atccattatc ttgtgcagct   48480
tgaactactg aactacgcaa attagcagta cgcataaagc tttcgtacaa ggcagcatta   48540
ccaaactgct gaatgtataa tgtattataa gccaaaaggt cgcacagaac gtttaatctt   48600
gagccttcaa aatcataatc caaaaattca ttttggccat taagccattc aatgaggttt   48660
tgttttattt cagcaaatgt accccgacg aatatctcgg gaatagcatt tgctgttctt    48720
gttaattgat aatttacagg ggtatttgcc attttaaatc ctatttaatg aatactttag   48780
atgatgcctg agccacagta tcaccgcatg atattggatc agccatttga acagcttcct   48840
```

```
ttccagtgac atatacctta gaagttctag gttgtgtcac tccgccatgt gtttcatatg   48900 gcttttaat  ttctgtgtgt tctgtaattg gatcacctgc tacgagaaca gcaattcctc   48960
cagtgaatac tttactttgt gtagcattca caactgttgg aggccatgct tcatggccgg   49020
cagtaacaca cttatcataa cttaatcctg acatttatgg cctctcatac acgtagcttc   49080
tcaatttatt agcccaacga ctccaatttc caactatagt ttttgtgtaa tttttaacga   49140
gagtttttct tattggagct ggaggatcag tcggttcagt agtatcagaa gatgacctag   49200
aattactgcc agaacctcca gattcacttt gttcttggta gtcatatatt aatgttactt   49260
cgtaagtgaa tgtcttctgg aggttttgag gagctttcca taaatataat tgagtattag   49320
aatcagttgg aaggtcttcc catgaagcag cagtttaaaa ttcattatct aaacgatatt   49380
tcaatgcgtc atttccaaat ccaaatacag attcatacgt tccatgtaaa cgattttctt   49440
ctactaaaac cccaggagtt tcttcgtaac tagttatatt tatagatact aacgtttcac   49500
ctgtttctaa ttgagcggta aaggtgacgt cgatagaaga accttccatg gattctccta   49560
aatcagcgct cattggaagt atattagcca atgtcaatcc tcgatccatc aattgtgtat   49620
tgaccagatg aaatagaact catagatgcc attttttctg tccaatcgcc accaacgtcc   49680
caatcaactg tcccagcaac tttccaagaa agatttccat ttactgtatt agtctgattt   49740
ccttcaacta aagtggtagc atctcccttta actgtaatgt cagcattacc ttcaactaca   49800
atagtaacat taccttttgac taggatagtt ccattacctt caaccgtctt agtttcatcg   49860
ccacgtacaa atattgtatt gcttccatct atttggtgga gacgattatc catgttgtaa   49920
taaatttctg atccaccgac gttagtcttt ttatcgccag ctaccaaaaa attaccatcg   49980
gcatttgtta tatcatacaa attatcaaca gttttcttg ttcttcttcc tgacggtgat   50040
acttcctcat atgttccagt cggatgaact aatctgtatc gttcttgccc gggggtatca   50100
tcaaattcct gaatatgacc gctttcagtt tccattgtgt gaacatacgg atattcgcct   50160
ttatatgaag aaacaggttc tttgaataaa attctcgaat cattcggaat aggagggtca   50220
gctggatcag aagactttgc tacagcagca gccattgctg acaaagacct agccggtgtt   50280
ttcacttcaa taccgtatga ttccaaatta cccgtaagaa taatcatggt aacacgggat   50340
gcacggcctt ttgtttgttg ataccacaat gaatcacgac cagctttata tgccttttcc   50400
caatctccgg ctaacatagc agttaacatt gtgttaaatt tagctacacc accaacaccc   50460
atctgaaatg ccatattttc taatgccatt tgacgagaac gattaactgc ttgccaaact   50520
gggccaactt tagaatgtga tttaatgtca cgttgcatat cagccaaatc acgttcaaac   50580
aaagttaccg cttcttccat tgtaatagaa cctggatttc cggtaatttc acgaccaact   50640
tgttttgata aaactttatt aatttgagtc atatcacgaa ctggctgctt catgataaga   50700
tgaccaatac caattgtcgg atatccttca gtatcccaat aaacttttag tcttaatcct   50760
tcatcacggc gaagcatttc agccattgac atatttggat tatcatcagt tggaatttct   50820
gataatggtc tatcatcagg atttatcgca gtgtctagat tgctatcttg gataaatatta   50880 gaagacgaat catatcctgc ttctccgcct tggtttaata cgttagtatc atttcctaaa   50940
cgtctaggat actgtccagt tgggtcagaa aatccttcaa gtctattagg cttttcgcga   51000
actattccac catacgtgcc aaggacaatt ccgttagttt tccatttgtc taaaaaatga   51060
ccataaactc tagttccttc taccggacca gtaacggagc ctccaattcc agacattgct   51120
gcagaagtta taggttgaat aactgacatc catggtaatt tatcagttgg aatacccatt   51180
acgtcgcctt gtgctctttg aggtggatgc agaccaacta cacgaacacg aacacgacct   51240
```

```
aattttaatg ggtccattct atcttcaaca acaccaacaa accaattaag gttattactt   51300
atcatttcca taagatttct ccattatacg tataaggtcg ttcataaatg aatttatgtc   51360
tgattttgct attattttta tttgacgaag ttttcattt tcaagaacag cagcttcata    51420
cgtatcgacc gcagcaagtg ctccttcata ttgaggatat tttctagctt tatcgccttt   51480
gtcataccaa acatatggat tatcatcgta tgatattaaa ttataaaatt tttcaccgtt   51540
ttcattcaca tgatatacta tttggtctcc acctacgttt ttgtattttt gtatagatgc   51600
ttgataagca gcttcttgcg aagtaatcca tccataatac ggatcataat tatcattaca   51660
catcaataaa acccaataca actgcggatt tccatatata gcatttgcta attcttccgg   51720
gcgtggtgaa cctttaatat aataagtacg taagcggtat cccgcaagag cacgtttgaa   51780
atagtcttta tagtttctaa aaatatctgt cataggaata gtcggcgcgt ttttattcac   51840
cgttttggcc gcatattcaa tcggatcaaa aaatgtaaag agcatgggcc ctcctgttta   51900
taaatatatt atctatttat aaggagaatc caatggcata ttctggaaaa tgggttccta   51960
aaaatatatc aaaatataga ggtgacccta aaaaaattac gtatagatca aattgggaaa   52020
aattcttttt tgaatggtta gataaaaatc cagaaattat tgcatggggt agtgaaacag   52080
cagtaattcc ttattttgt aatgcagaag ggaaaaaacg tagatacttc atggatattt    52140
ggatgaaaga ttcttctggt caagaatttt ttattgaaat aaaacctaaa aagaaacac    52200 aaccaccagt taaaccagca catctaacaa ctgcagcgaa gaaaagattt atgaatgaaa   52260
tttatacata ttccgttaat actgataaat ggaaagcagc gcaagcttta gctgaaaagc   52320
gcggaataaa atttagaatt ctaacagaag atggattacg agctcttggc tttaaggggg   52380
cataatggct atttttcaaa taattaatga aagcactccc caagttccaa aggttaagca   52440
atcattaaac gaaagaaat ggattcagat aggtcttgaa tacaaaaagg ccaaagcaaa    52500
aggaatgaca ggaaagcaat ttgctgaaga aagaggaatc aaatactcta cgtttacttc   52560
agcaatgtca aaatatgctt caggaattaa aacagctgaa aagattcaaa agcttgaatc   52620
aaaaccaatg aataaactca ataagcaaga aagacaactg cttatgataa attcattcag   52680
gcaaacattg cgtgataaaa ttcgtaatga aggtgcagca attaataata aaaccaaaaa   52740
gtggtttgct gaaactatta acaagtaaa ggacataaa gttgttcgcc cgcagccggg     52800
acgaatatat gcttttgctt atgatgctaa acacaaggaa actcttcctt actgggataa   52860
atttcctttg ataatttatc ttggtttagg taaacataat ttaatgtacg gattgaactt   52920
gcactatatt ccacctaaag ctcgtcagca atttctagaa gagcttttaa agcaatattc   52980
aaatacacct actattacta ataaaacgaa attaaaaatt gattggagtc aagtgaaagg   53040
atttaggggt gcagaccaaa tgattaaggc atatataccc ggtaatatta tgggtagcct   53100
tgttgaaatc gccccgaaag actgggcgaa cgttgtgtta atgccacttc agcagttcgt   53160
ttcaaaagga aaacgtttct ctgcaaacaa agtctggtca aatatctaat tctattatct   53220
tccattcttt tctattgttt gttctaattg gaattgaatg gaagggactt agacccatta   53280
taccaccaac atttataaag cattatgagg aatatatgtc gcaagcactg caacaaattt   53340
ttaaccaagc aaatacaact aactttgtag tatcaatacc gcatagtaat actacatctg   53400
cttttacttt aaatgctcag tcagttccta ttccaggaat taggatacct gttactgata   53460
ccgtgactgg gccgtttgga ctaggccgag cacaacgtcc aggagttaca tttgagtacg   53520
atccacttat cgtgagattt atagttgatg aagagcttaa gtcgtggata ggaatgtatg   53580
```

```
aatggatgct aggaactagt aactatctta caggtgaaaa tactgcccaa aaaacaggtc    53640
ctgaatacat tacgctttac attttagata atagtaaaac tgaaatcgtg atgtcaataa    53700 attttatat aa gccttgggtt tctgaccttt ctgaagtaga atttagctac acggaagatt    53760
cagacccagc cttagtatgc acagcaacga ttccttatac gtattttcaa gtagaaaaag    53820
atggcaaaat tatagcagaa gtttaatgct tcagtttcat gtgttataat cttaactaaa    53880
tttgaggaga acatatgaa a ctaatctttt taagtggtg taaagcgtag tggaaaagat    53940
actactgcag attttatcat gaataattat tctgcagtta aatatcaact tgctggtcct    54000
attaaggatg cattggctta tgcatggggt gtatttgcag caaacactga ctatccttgc    54060
ttaactcgta aagagtttga aggaattgac tatgatcgtg agactaattt aaatctgact    54120
aaatcagaag taatcacgat tatggaacaa gcattttgct atcttaatag taaaagccca    54180 attaaggcg tatttgtttt tgatgacgca gttaatttcg tagcatttaa taagattgct    54240
gacgttataa ataatattga agatcaatgg tcagtccgtc gtctgatgca agccctaggt    54300
acggatttga ttgttaataa cttcgaccgc atgtattggg taaaattatt tgctttagat    54360
tatcttgata aatttaactc aggttatgat tattatatcg ttcctgatac tcgtcaagat    54420
catgaaatgg atgcggctag ggcgatgggt gctacagtaa ttcatgtagt tcgtcctggt    54480
caaaaatcca atgatacaca tattacagaa gctggattgc caattcgtga tggcgattta    54540
gtaattacaa acgatggttc tcttgaagaa cttttttcta aaattaaaaa tacactaaag    54600
gtactataat gtctgaacaa actattgaac aaaaactgtc tgctgaaatc gtaactctga    54660
agtctcgtat tcttgatacg caggaccaag cggctcgtct gatggaagaa tccaaaattc    54720
tgcaaggaac tttggctgaa atcgctcgtg cagtaggtat cactggcgat actatcaaag    54780
ttgaagaaat cgttgaagct gtcaagaatc ttactgctga atctactgat gaagcaaaag    54840
atgaagaata atggaattta aagacttttc aacgggtctt tatgtagcag ctaagttttc    54900
agaattaaca cttgatgcgc tggaagaact ccagcgctct ttacgtgttc ctaatccagt    54960
tcctagagaa aaaattcatt cgaccatatg ttattcaaga gtaaatgttc cgtatgttcc    55020
atcaagcgga agttttgaag tagcttcttc tggacattta gaagtatgga aaacacaaga    55080
tggatcgact cttgtacttg tgctagattc tgaatatctg cgctgtcgac acatgtatgc    55140
gcgggcacta ggtgctacac atgattttga tgattacaca ccgcatataa cattgtctta    55200
taatgttggg cccttatcat ttagcggtga tgtacaaatt ccggtcgtat tagatcgtga    55260
atacaaagag cctcttaaac tcgattgggc agatgattta aaataatttc acaaagttgt    55320
ttacatgctg atgaggtagt gatactatta tctcatcaaa attaattagg aaaataaaat    55380
gaaaactttc aaagagtttg ctacaaaaac tactattact gaatcttctc atggtatgga    55440
agtaaagctt ggaatggctt tagctgaagc tgagcgtctt ttctctcgta ttaaagaact    55500
tgctgctgca gtcgatcctt catctttaa aggagaccaa actaaagtta aagcactttt    55560
agcattatgc tcagatgcag gagaaattgc taaaaatggt tctaagatga agaaacgatt    55620
agaagattta aaataatttc aaaaagttgt ttacacaggg ttttagtagt gatactatta    55680
ccctatcaac taccgaggag aataaaatga aacgttgtga attaattcga aatgttgcta    55740
ttgcaatttc tgcttccgct tttagttttt caatgtttgt tggatttata tgcggattat    55800
tgactacagc agaaaatgtt ttttcacttg tagtagcatt tttaattggt ttaatcgcta    55860
ttgttatgga taaaatttct aaaggtgaat aaatgaatat taacgaatat tatgtttatg    55920
ctggggatta tgcaaatcct tctcatttg aaggtaattt aatacctgat agagttttta    55980
```

```
atactccttt tgaagcgtgg agttgggttg aaagtaaaaa tggattttct tatcgttatg    56040
ttgaagtaac tgattggaaa ggaactaaat atcctaaaga gcattattat gtagacccat    56100
ctaaagtaaa ttttcttttg ttcgcaggcg ataattacta tccttgcggt ggatatgatg    56160
atttgattgc gtatgctgaa acagaagatg aattacgcca aattattgaa gacaataaat    56220
caaaacgatt tggcgatagt tttgactggt ggcaaatcgt aaatgcccat acacatacta    56280
ttgttgataa aggttaataa tgattcttta tgcgaaagta tcatccattg aaaatggata    56340
taaatatgat caagaagcag ctaaagcctt gattgatgat tatggcattt taacatgttt    56400
tgaagttgaa aaggtttaca ttgatcgttc atcttctcaa gttaaattag tgaaggaaga    56460
ccgtaaattt aatacagtaa attttgattt ctttattgaa acggaaaaag gtcctcttga    56520
atatgatatt ttcaagaatc ctttgggtct tgaatgcatc gtaaatatgt attatcataa    56580
atggtaaata tgctttaaga attatttgtt attattaact catatcgcac tgattaatac    56640
cctctatcat caaggttct tgcttgagag cctttgttaa taattgggaa tcatattatg    56700
gatactaaat tagctgaaat ttttgaagga aaacatccaa attttagtac aggaaagctg    56760
aaagataaaa taataaaaga aaatattttt ccatatgagt gcgcaatttg taaaatttca    56820
aaatggcaaa ataagcatat tgttctgcaa ttagaccata ttgatggaaa taacaaaaat    56880
catcttaaat caaatttaag attattatgt ccaaattgcc attcgcaaac tgatactttt    56940
gctggtaaaa atattaaaaa taataaaaag cgttataatg ttagtgatga agaaattta    57000 aacgcactat taaattcggc tactatatca tctgcaatta cttcattagg tttaagtaaa    57060
ggcggaaact ataaaagatt cattaaaatt gctaatgata taaaattata tcatttactg    57120
gtaaatatta tgaaaagat tttaactgat gaaatttacg aagaattagt taaaatcgat    57180
tattctaaat ttggatgggt tagtaaagct gctaaaataa taggtataag cccacaaaaa    57240
gctagaaaat ggatagaacg aaagtgtcca gaattgatag aacaatcttt ttcacgtaat    57300
aaataatata gagcgagaat ggtcaaattg gtaaaggcac agcacttaaa atgctgcgga    57360
atgatttcct tgtgggttcg agtcccactt ctcgcaccaa atttgcggat atcgtataat    57420
ggcattacct cagacttcca atctgatgat gtgagttcga ttctcattat ccgctccaat    57480
ttaatttact ccgtgtagct cagtttggta gagcgcctga tttgggatca ggaggtccaa    57540
ggttcaaatc cttgtatgga gactggaggc gtggcagagt ggtttaatgc accggtcttg    57600
aaaaccggca gtcgctccgg cgactcatag gttcaaatcc tatcgcctcc gccagttttg    57660
ctgatttagc tcagtaggta gagcaactca cttgtaatga gaaggtcggc ggttcgattc    57720
cgtcaatcag caccaaggcc ctgtagctgg aaggttcaag caagcgactc ataatcgcca    57780
gatggtggtt caattccacc cagggccacc aaattaattt ggggagttat cccgtagagg    57840
tagcggtgtg gactataaat ccattgtcat tgcgactcgg gtggttcgac tccatcactc    57900
cccaccaatt tggatgtgta gctcaatggc agagcgatcg cctgttaagc gattggttat    57960
aggttcgaat cctatcacgt ccgccaaatc cgaggcatag ctcagaagga agagcaagga    58020
ccttctaagt cctaggtcgt aggttcgatc cctactgcct cgaccaaaca agaaaccggg    58080
tcgctaccgg taagtcgtcg gactgatgtt ccctgagtaa ggactgacat tatcaaatct    58140
ttacgatctg ttaatgtccc cttacatcac agcagaaacg gcgcacagaa ttatcgattc    58200
gaggaaatat ctttgccgta agccgagtag cgttttttgac ggaacgttcg gatatggtcg    58260
agatatggcc ttttaaaaat attgagtagc gtcaactgct taataaccgg gttcgaatcc    58320
```

```
cggcgtttcg tacaaacact tgccttagca ggtggaaccc cgacaaggtt gccgcaaggc    58380
ttagccccga ccgaaaggtt ggggcttttt agtataaata tagtagtata ttaaatccac    58440
gaattaaaac aggaaataag atgaaatcat atgctcaatt tttaaatgaa gcggtgttaa    58500
atgaagcatc tagcaccgaa attcaagctg tcgcaaaagc agccattgca gcgggtaaat    58560
attcctataa agatgcttct gacgaatcac gattccaatt tgctcgcgac atgaaagcag    58620
aaggatttac gggaaatgca gttagtatgg cctggaaaag tttagttgct actggcgctg    58680
cttttgcaaa gccttcgggt aaacctgctc ctaaagcaga tcctaaagcg cacaagaaa     58740 aaaatatcgt taaggaatt atctctaaat atgaagctat ccttaaagag cttttagtaa     58800 tcaaaccga aggccaaaag ttagcccgtg cttatagttt caaagataat ccacatgttc     58860
actctcttga gtatgttgaa gacatccaaa aaattattaa agaccgcatt tggtctgcta    58920
aacaaatcaa ataacattct tagccccgac tgaaaggttg gggcttttta gtttgaatca    58980
catagagaat gctgctacgg atagtaacaa agtaataaat aattaataac caaccgataa    59040
attatttcaa ggattttaaa tgaaaaccta tgccgaattt ttaaccgaag cagcaaaatt    59100
accatctgaa gcagatctta ctaaagtatt cttccaattg gacccaaaag accgcggcga    59160
ttttcttaag tggaaagcta aagctattga aatgtacaac atcgataata gttcttttac    59220
aatgagtcaa gaaaataaat tcaataaagc attttttcaaa atttctaaga aattggcatc    59280
tggcgctcag gttcctaaat ctgtattagc tactcctgaa cgtgcacctg ttaaaatttc    59340
taagaatatg ttcgacacta aaaaatacgt taatgctttg aataaagctc ttgatgcatt    59400
ggatgatgca aagaaggcag cccgcgatct tcaagacgtg tacaccgatt ttgatcgtaa    59460
aactaaaggt tctatttcaa atagcgaacg caatagtgta agtgtttatt ctgatagcct    59520
tgatgttctt ggcgatgcgt atactgaaat taaaaatcgt attaacaccg catctaagct    59580
aaaagctgct gccgaagcta taataactaa actaggcaaa taattttaaa tccctatcta    59640
aatgataggc cttttttggta tctaggcctt tctggacctc tctaggcatc atttagttta    59700 tacccttttat aatatattat cctatctttt aattgcccat ccctgcccta gaattcccta    59760 aaaatttta aaattttttc acaaaactat ttacatccct gttcttccat ggtactatac    59820
aactatcaac tactgataca gaaaaacaac ttggagaatg aaatggataa ttacggcgaa    59880
ctgttcaact tctttatgaa atgcgtttca gaagatttcg gtcgtacagt gaatgatatt    59940
aaagttatcg gtcctgacca tccgatgttt gaaacttacg cagtaatggg taatgaagac    60000
ggacagtggt atactgtaaa ggttgtgatt aacatgttca cagcagaagg ttatgttaaa    60060
ctgtcttcta agtttaccca cgataacgac gaaatcgcag aagaatattt caataatatg    60120
aaataagttt acataggctc atgattgaga tattatgagc ctacaatttg aggaaaaccg    60180
ctatgtctct ttataccgaa ctgaatgaaa cttccgaaaa atcttttgat gatatcttat    60240
caataatgca aaaacaggta ttagaacagc ttagtgaagc cgcaagcaat gggcacaagg    60300
cttgtcgagt ccaaagccca catcgccgca tgtatgaacg ccctcttatt aattggctag    60360
aaagcgaagg tcttacagtt aagatttgcc ctgctaaatt tgatgtccca cgtattctta    60420
atatttactg ggataaaccg gctgagaaat tggttgagaa aagtgaccct tgggttgtta    60480
atgtaaaaac atgtgacagt ggatgctcac ttgaggtgtc tgctgtaatt aaaggcactc    60540
atggtgaaaa atcatggggt tggcctagta agataaaga atcgtgtta agtgtaaaag      60600 ctactagtat tagtactcct atagctaaaa gcattatcgc cgccgccgtt gaagaagctg    60660
aacgaatttg taaaattaaa aatagtttac atctcttaaa tagtatgata taattcttcc    60720
```

```
acagatttta tttttaatca acctaaggaa atactatgaa cacactgaag aaaattgttg   60780
aatttattcg cactaaactt ggttctgcta tggctaaaaa tttatctgtt gaagaacagt   60840
atactgctgc agcagcaaaa ctacttgata aaattaaaga tctaaaaact gcttctgtta   60900
aatctattaa tgaagaaaaa cgtattcgtg aacttattgt cgaaaagaat cgacaagccg   60960
aatcaaaaga gcgtgaaatt cgtaaacttc tttccgaagg tcaagatgta acaatgcatg   61020
ctaaactcgg tttactatat cgtcgaacag ctgagcagtt gactactaag gctgacggtt   61080
atgctgaaat gcgaattgaa atcgccaaga aagtagttga gttagatgat gctcgtcaag   61140
aacttgcggt taaattggaa tatatccgtg aaactcgtgc agcaaatgcc cttggaatta   61200
gtactgccga tgatgtagtt gaaattgcag cactgactaa ggttgatatt gaagataccc   61260
ttgctcgagt tgaaaccttt aacggtaata tttctggggt tgaaactacc tctgccgatg   61320
ttcaggaata cattaattct ctgaaataat gataaggggc ttcggcccct tatacttgga   61380
gtaaatagga atgaaaatga aaatgcaaag tgatttcaat tcaatgtttg aagagttcca   61440
aagacaggtt gatgttccag accaattact aaatgctctt aaacgcatgg cagaaggacg   61500
taattattat tggggtctt catacgaaac tgatgaaagc cttccggaa gattttctag   61560 aggtaaaaag tctttaatac gtcctggaat actcattaac agtattgaat caattcattc   61620
attgacgtgt gattttgatg ttgaatttac tgatttcatt tctcctgaat ggacggtttg   61680
ttatttaaac gacgattatg attatcttgg cgtttatagt ttaagtgacg catggtttaa   61740
acgtaattta caaaagtcaa atttattcta tattgatact acggtaaaat ttcagggaaa   61800
gaaatatttc tttactctta tagttgattc tgaaacaaag catgaaaata aacgtattct   61860
tagtaaaaag aatatcttaa ctattgttga tgatcttttt gataaattag tggaaaatcc   61920
taattttgaa agcgatttat tattagaaaa atttgttaag gaatgtagag aatatgtcaa   61980
agccatcact ataccttcca gtaaaacctg tgaagtatga accaaagcgt cagctaattt   62040
ctactgatgt gttaataggt cctgtggtag ctgtatcatt tgtgattttg ctaattgctg   62100
gaatggttat agacgttatg actgatattg aatctggtgt aatatttgga gcaacactaa   62160
ttcttccatt ggtagttccg tttttattag tacctgtaaa ttgggtagga tactggtatc   62220
aaggaagaca ctatcgtaaa cgtgtacgtg attggaaagc ccagtgcaaa aagattaaaa   62280
aagaacatca gcttaaactt gctgcgtatg aatttgatga aattatgaaa tttgttaagg   62340
aatcacgatg caaaagccaa aactaaataa agtcaaatat tcttttttctg agtcattttt   62400 aattttgct gtggcgttgg ctgcagctct tgcgggtagt cttattggat tgttaattga   62460
ctgttttatt ttaaacatcc gcagtaatgt cagcggtata gtagatataa tagaagtttg   62520
gagcgaactt cattatacta tagtaatttc attattttca ttctttggta ttattttata   62580
ttttcattat gataatttta aaataaattg gcaaagaaaa aaggattaca aaatacaatt   62640
aaaagaatat aataactaca tgtcttatat tgaaaatgaa tcaatgaaag agtttgtgag   62700
tgattgtagg aaaatcaaat gattttaaaa actcgctggt atgatttaga tgatggggac   62760
gatggcattt cagttgatag agttgactgg agcggctgtt ctgaagatac aaagaaacga   62820
ttaattaggg agtttagaat gggatatcaa gcagctaagc catctactgt aacagatgat   62880
aagttcgtat gtattcaaaa cggtcgtgct aagttaacga acgctgattg gtttacaggc   62940
aagaatatgc tttatggta tatcattagt cttcctgtgt catcattcgt attttatttc   63000
tttggaaaaa atccaatgga tagaatagga gattgggctc tttttactct gcttgttaat   63060
```

```
attttttataa cagcagtaat atcaggaata tggtgcgtgt tcattgaaat gccatggcgg   63120
ttacgtaggc agcaaaagat ttttgatgaa aagaaatata cccaaaattt aaataacttt   63180
atcactgaat gcaggaaatt aaaatgaaaa cactatcagc tggtattatc tttatgacag   63240
aagataaaga tttatttatg ggacgagtta ctggttctcg taaacctgga atgatggcac   63300
atcgctggga tattccaaag ggccgtgtag aaagttctga tttgaatgca ctggaagctg   63360
caaaaagaga atgctcagaa gagactggtt ttatcgatta taattcagac cttctagaag   63420
acctaggtgt atttaaatat tctagtaata aagacttaca gttatttttat tatacgattc   63480 cagtagagca tgagatgttt agaaattgcc attgcgagtc ttattttgaa aataaagatg   63540
gtgttatgat tccagagatg gatgcttttg cccttattcc tcgtactcag tggcaatatg   63600
tgatgggtcc ttcactttac cgaataatga acagcctctt ttaatttata aataccttct   63660
ataaatactt aggaggtatt atgaatatat ttgaaatgtt acgtatagat gaaggtctta   63720
gacttaaaat ctataaagac acagaaggtt attacactat tggcattggt catttgctta   63780
ctaaaagtcc atcactaagt gttgctaaat ctgaattaga taaagctatt gggcgtaatt   63840
gcaatggtgt aattacaaaa gatgaggctg aaaaactctt taatcaggat gttgatgctg   63900
ctgttcgcgg aattctgaga aatgctaaat taaaccagt ttatgattct cttgatgctg   63960
ttcgccgctg tgcattgatt aacatggtct tccaaatggg ggaaaccggc gtagcaggat   64020
ttactaattc ttttacgcatg ctccagcaaa aacgctggga tgaagcagca gttaacttag   64080
ctaaaagtag atggtataat caaacaccta accgtgcaaa acgagttatt gcaacgttta   64140
gaaccggaac ttgggacgcg tataaaaatc tataaagttg tttactttct cctagaattg   64200
tgatagtata ttaacagtta cttggaggga taaaatgact cgtattaatt tgactttagt   64260
atctgaactt gctgatcaac atttaatcgc agaataccgt gaactgccgc gtgttttttgg   64320 tatagttcgt aaacatgttg caaatggtaa gcgggttaaa gattttaaaa tatcttccga   64380 gtttattttta ggttctggtc atgtcacgtt cttttacgat aagttagaat ttttgcgaaa   64440
gcgtcaatca gacattataa cggaatgctt aaaacgtggg tttagtataa aagatactga   64500
agttcctgac atcagcgata ttccagcaga atggaaaaat gattataatc catgcaaatc   64560
agctattaag ttgagtcaac aacgactcga tgaaaaaatt ttaatgaagc catactggta   64620
taaatactac ggtaaaacta tttacatttta aaggaaacac atgaaaacat atcaagaatt   64680
tatcactgaa gcagctatta attctcaaat tatcgctgaa tcttttactg atcttttgaa   64740
atttaaaaaa ggtcaaaaaa tcactgctgt attggatgat ggtacagaag ttgagatgga   64800
tgtacaggga tataattatg cagtagatgg aaaactgtat aataaatctc atgctaaatt   64860
tgattcattt gacgattttg ttaatacagt tgaagatgaa aaaactcgta gatccattgc   64920
aactggcgac gctaaggttc ttatggcaca cggtcatgaa cgtatccgcg ctaagcagaa   64980
taaaatgggt gaagataatt ttgcattagt tggttatcaa tctggtaaac aaacttatgg   65040
ttatcagcgt actgctacca tgtataacaa aaatggtaaa atcgctttcg tgaatagcaa   65100
aggctctatt cagtacgtca aatcattcaa ataagcaaat aagaaatatg gaacaagct   65160 ggacctcatg attctatgag ggattcccgc caacctgtaa taaggtcgag cccaagtgcg   65220
gtaatgggta aatacagaaa tggacaattc atgcgccatg gaatggccca aatttagaga   65280
gaataaaatg agaacatttt taactggtcc ttatctatcc ctgatgaatg ctttttacaca   65340 ccattctgat gctagagtag aagaaatttg taaaaacgat tatattccac catttgaaga   65400
cttgcttaaa caatattgta cacttcgact agatggtgga cgccaatctg gtaaatcaac   65460
```

```
tgctgtgact aactttgctg ctaattggct gtatgacggt ggaacagtta ttgttctttc    65520
taatacttca gcttacgcta aaatttctgc aggccacatt aaaaaagaat tttctcgtta    65580
ttctagtgat gatatacgtt ttcgtttatt tactgattct gtccgtagtt ttatcggtaa    65640
tagaggcagc aagttcagag gtttatcgct ttcgcggatt ttgtatataa tcgatgagcc    65700
tgttaaatct cccgatatgg ataaaattta cgatattcat attgaaactg tacaatactg    65760
ttgcaatagt aaatgttgca ccggtggtat tactcgtcct caattttttg tgatcggaat    65820
gcaatgatga cagacacaca gcttttcgaa tatctttatt tttcgccaaa aactattaaa    65880
aataaattgg tgaatcattt tgaaattttg gcaaataata atgtcttgag cgaatttat     65940 cctaagcaat acaaattaca aaaggtgta ttcaaggat gcagagtttt gtgtactgct     66000
cctaatgcaa gattaatgaa taaaattcca tattttacca tggaatttat tgatggacct    66060
tttaaaggac taatcaccca aagtttaatg gcatatgatt ctgagccatt tttaattaaa    66120
gaacagtctt ggataaattt attttctaat tgaggttata tgaaagcata tcaaattctt    66180
gaaggcacac ataaaggtac tatttatttt gaagatggta ttcaagcacg aattattgtt    66240
tctaaaacct ttaagagga ctcttttgta gacccagaaa ttttctacgg tttgcacacc    66300
cgtgaaattg aaattgaatc acatcctaca gttaaaattg aaggtggtca cacctgaac    66360 gttaacgttc tgcgtcgtga aactctggaa gatgcagtta agcatccgga aaaatatccg    66420
cagctgacca tccgtgtatc cggttatgca gttcgcttta actctctgac tccggaacag    66480
cagcgcgacg ttatcgctcg tacctttact gagagcttgt aatggcaaag ataattattg    66540
aaggttctaa agatgtgtta aatgctttcg ccgagtggtt tagtaattca ggcgaacagc    66600
aatttaatga agcatggacc atgggtgata ttgatggaat ttatcctacg acagaaattt    66660
ctgttcaagg atatggcatt catgaaccta ttcgtttagt tgaatatgat ttatgtactg    66720
gtgaggaagt caaatatgat tgaagatatt aaaggttata agccacatac tgaagagaaa    66780
atcggtaaag tgaatgctat caaagatgct gaagttcgtt taggacttat ctttgacgct    66840
ttatacgatg aattttggga agcactagat aattgtgaag actgtgaatt cgcgaagaat    66900
tatgctgaaa gcctcgatca gttaactatt gctaaaacga aactcaaaga agccagtatg    66960
tgggcttgtc gtgctgtgtt ccaaccagag gaaaaatatt aatggctcaa ttaagcgcag    67020
ggtttggtta tgagtattat actgcccctc gtcgtgtatc tgttgctcct aagaaaattc    67080
aaagtcttga tgacttccaa gaagtagtcc gtaaagcttt ccaggactat gcgcgttatc    67140
ttaaagaaga ttcacaggac tgtcttgaag aagatgaaat tgcttactat gagcaacgtc    67200
ttgaacagct aaaaacctg catgaggtcc gtgcagaagt ttcaaagtct atgaataaat    67260
tgattagatt taaagaataa ctgtttactt ttcctcttga ctgtggtata atttttctat    67320
cagttaagag gagaataaca tgactatcaa cacagaagtt tttatccgtc gaaataagct    67380
tcgtcgtcac tttgagtcgg agtttcgtca aattaacaat gagattcgtg aggcatcaaa    67440
agcagcaggg gtctcatcgt ttcatctaaa atattctcag catcttcttg atcgtgcaat    67500
tcaacgggag attgatgaga catatgtttt tgaattattc cacaaaataa aagaccatgt    67560
tttagaagtt aatgaattcc tgagtatgcc tccgcgtcct gacattgacg aggatttat     67620 tgatggggtt gaataccgtc ctggacgttt agaaattaca gatggaaatc tttggcttgg    67680
atttacagtt tgtaaaccta atgcgaagtt caaagacccg tcgcttcaat gcaggatggc    67740
aattatcaac agtcgtcgtt taccaggaaa ggcttctaaa gcagtaatta aaactcaatg    67800
```

```
aggtaagcat gagaaaagca ctactcgctg gtctattggc catttcaatg atggcgcata   67860
gctccgagca tactttcagt aatgtccaac tcgataacat gcgttacgca tatcaattcg   67920
gggaacaatt ttctaaggat ggaaaatata aaacacacaa aaatatccac aagagcggat   67980
tgggtcatat aatggctgct attttgtggc aagaaagctc tgccggagtt aatttaaaat   68040
ctaaaccaaa gcatcatgcc tatggaatgt tccaaaatta tttgccaact atgcgagcaa   68100
gagttaagga acttggttat aatatgaccg atgctgaaat aaaaagaatg ttgaataaac   68160
ggtccaattc agcttcctgg gcgtacattg aactttctta ttggttaaat atacataagg   68220
gcgatataag aaaagcaata tcctcttata attcgggatg gaatgttaaa gcaggttcta   68280
aatatgcttc tgaagtccta gaaaaggcta attaccttaa aaataataaa cttttggaaa   68340
tagtaaatga ctaaaatttt ggttttatgt ataggattaa tttcattttc tgcttctgca   68400
tcagcagata catcatatac tgaaattaga gagtatgtaa atcgtactgc cgcggattat   68460
tgcgggaaaa ataaagcatg ccaagctgaa tttgcacaga aattaatata tgcatataaa   68520
gacggagaaa gagataaatc aagcagatac aaaaatgata cattgttaaa acgatatgct   68580
aaaaagtgga ataccttaga atgttcagtt gcggaggaga aagataaagc cgcttgtcat   68640
tcaatggttg accgtttagt agattcttat aatcgaggat tgagtactag atgattgtaa   68700
aatatatcaa gggcgatatt gtcgccctat ttcttcaagg taatattatt gcgcacgggt   68760
gcaattgctt ccacacaatg ggctctggcg tagcaggtca attagcaaga gcctatccca   68820
aaatttaga aatagataaa accactaccg agtacggttc tcgtgataaa ttaggcgata   68880
tgtctattgt ttttaaacat aatcctacag gatttggtat atgctataac ctgtatacgc   68940
aatatgaacc gggtcctaat cttgattatg gtgctttagt aaactgcatg atagaattaa   69000
atctacaggc agaaaccctt ttgtttaaac cagtaattta cattccacgc ataggttgcg   69060
gtattgctgg tggtgattgg gataaggttt ctaaattaat tgacatgttt actcctgata   69120
ttgatttaat agtggtggat tatgaaagta cattacccgc atccgtttga tcctaaaaac   69180
aaagtggaaa ttattcgtca atgggaacgc atttgccgta ctaaatgccc aattaatagt   69240
ccacatgatg tagataaaga ctatattgga acattcgttg aatatacctt tattgataag   69300
aaaggtcgta acaacatgt agaagaatat tgcttaaagg ttacatggtt atgagccaaa   69360
ctagtattct taaaaatgcc cactgcgaaa agtgtgaatg gccggttgtt tttgctttat   69420
gtaatgatga atggcttgc gatttcgatt attggtgcta ttgttctaat aaaggatgca   69480
tcaatcataa aggtgaagga ttttattcag gattttatcc ttatcctgat ttcgttaaag   69540
aaggtaaacc aaaatgaacg atgatttaaa atatcaatta ttacgtgaac ttgatgtttt   69600
gattgaactt tctgcgcaaa aaggatttat aattggatca ggtcaaaaag accccaacgg   69660
tcattcaatc gtagcggtta tgaatcagaa acgagtcatt ttaaaacttt tggggattga   69720
catactgtga gcctaagcaa agaacaaaaa gacagactat tttctcttat tcacgaagtt   69780
atggataaaa atagcgaatt ggaaaaagtt tgtgatgaat gcggtccttt taataccgac   69840
gaatacgaag aactgtgtaa agatttcgac gataaagaac aagaacttat taattatata   69900
aattccttat gattactcgc gaacaaaaga acgaaatatt attttagtt ggtgaaatta   69960
ttagtttaga aaaggatttg tcttttgaaa tatcttctga atacgagat gccgaaacat   70020
attacgaatt agtaaaatct atcgataaag ctgaaaatga tttagaaaca tatttagaaa   70080
atttaactaa ggactaagat ggcgagttta attttactt atgcagcaat gaatgctgga   70140
aaatctgctt ctcttttgac tgctgcacac aattataaag aacgcggaat gggtgtatta   70200
```

```
gttcttaagc ctgctattga tactcgcgat tctgtctgtg aagtcgtttc tcgcattgga   70260
attaaacagg aagcgaatat tattacggat gatatggata tttttgagtt ctataaatgg   70320
gcagaagcac aaaaagatat tcattgtgta tttgtagatg aagcccagtt tttaaaaact   70380
gaacaggtgc atcaattaag ccgaattgtt gatacatata atgttcctgt tatggcttat   70440
ggtctaagga ctgatttcgc tggaaaatta tttgaaggtt ctaaagaact tttggcgatt   70500
gcagataaac ttattgaact aaaagcagtt tgtcattgtg gtaaaaaagc tattatgaca   70560
gctcgattaa tggaagatgg aacaccagtt aaagaaggta atcaaatctg tattggtgat   70620
gaaatttatg tttctttgtg tagaaaacac tggaatgaat taactaaaaa gctcggttag   70680
tgcaaaagtt ataaataggt ttatctaact aaaggggtat atatgctaca attaactgaa   70740
aagcaacttc gcaatcttac tgttcttcaa ttagatgaaa ttcgtaggga agttggaaat   70800
atcatttcag ctttgcgtcg agaagtatca ctcaaccaat ctccggcaga ctatactaga   70860
ttgcgaaatt ttgaaaaata ccttgataaa gttaaggccg tgcatcggca taaagtaaat   70920
acaggacaaa aatgatagga ggcctttatg gccttaaaag caacggcact atttgccatg   70980
ctaggattag cgtttgtttt atctccaccg attgaagcga atgtcgatcc tcattttgat   71040
aaatttatgg aatctggtat tagacatgtt tatatgcttt ttgaaaataa aagcgtagaa   71100
tcatctgaac agttctatag ttttatgcga acgacttata aaaatgaccc gtgctcttcc   71160
gattttgaat gtatagagcg aggcgcggag atggcacaat catacgctag aattatgaac   71220
attaaattgg agactgaatg aaattcagcg acttttcaca aagtggaaaa ccttcaaagg   71280
cagatgaata cttaggttta ttaatggctg cacaagctta ttttcattct gcacattttg   71340
aaactaaaag ttatgctaga cacaaagcat acgattttat tttctctgag ttgccagatt   71400
tgattgataa atttggtgag caatatttgg ggtattctgg tagaaaatac acgccttcta   71460
ttccagatgc cagtaaactt cctaccgaca caattaaaat gattgatcgc atactagacc   71520
aatctaacag catttataaa gaaatgcctc cagccattca aagcacgata gatgatatta   71580
ctgggatgtt ttaccagagt aaatatcttc tttccctcga ataacattag tctccttcgg   71640 gagactttt  tcattttacc ggtttacttt ccatttgagc tgtgatacta tacaactatc   71700
ggataaagag gagaacatca tgaaaattga agcactcaat caagaaggaa atatctacgt   71760
catcattaat ggtgattttt tcgtcaacat ggatgaagtt actagtgaag aacttgtaga   71820
acttcttaag aaacgttatg atatgtgtga tgaagctgca actcacatgg cgtgtgcaat   71880
attctctctt tcatatgtgg tggaataatg attagcattg aacaagcaga taaaattaaa   71940
gaattggtag ctttaattcg caaagcagat gaggaactta gtgactttgc ttggttttcg   72000
tcaggcattg caaataaagg tattgaaaaa tttgaagcta agttgataa  tgctgtagaa   72060 gctttagata tgtttcttga tgaaattatc gatcataata cgagagttta agtatgctaa   72120
cacgtgaaca gtttgaaaaa atcattaaat tagcacgtga tattgaaata gattcatatc   72180
agttggcagt tgagcattgt gaaggatact catacgatgg tatagaagca gctaaaaagg   72240
atttggataa atccaaagct aagttagttc aatatcttga aatgattagg tggaataatg   72300
aaaactgaaa agcagatgtt tttaatgaag ctaattgaag aatatgctaa tgcagtttct   72360
gactatgagt attctgctcg agaaagaggt acagctttcg caaggaaga  atgaaaatt    72420 atggttgatg ctcacacaaa gcttcagaat tttattgaaa acgtcattta atggtttaca   72480
agttggcaag gttatgatat agtaatcttg tcaactgcca aggagaagag aatgaaagtt   72540
```

```
ttgtttgttg tgtatgtgat gattcaatat aattacccaa tgtttactta taatctggtg    72600
aacaatatta ttgatattat tcaaggagt atgtaatgac aagtgaacaa gcttttaagt     72660
taagagaatt aattgaaact ttaattggtg aataatgtga gctttccgaa attagaagta    72720
ggtgatttag tcttaacaaa attgtggaat gacgctcaat cagtgaaaat ctgtcaatat    72780
cgtggagcaa caggtaattt gatgtacacg atttataacc cagaaatttt gttagagtgt    72840
catttggaac gttttataaa agacaccgat agtatgcctt atagtgtatc gattgtacgt    72900
aaatctgata caaggaata ctctaaaatt ttaaaacaaa ttcatgccaa taaaaaggat     72960
taatatgaaa cgattagtac tagaagttag ttcactttt ggtgaattag ctatagaaaa     73020
agtaaataat atgtatcgtt tgacgcaaga agatgatatg atgtatttta cgcctagtga    73080
aatcattcat ttaacccaaa ttgaaaatcc ttatactgat aaaattgtaa gcattaatga    73140
tgagcataaa attcattttt attcttcatg cccaggattt aatattgaaa gcgagtcaat    73200
atgcctatca gttattcatt gggacagttt tatagataag attaaatatt tttattattc    73260
taatgaaaga aaacatagtt taaaatggtt taaaaattgc aatgctatta ttactaacgc    73320
ttgcaatcag aatgatgaaa ctgttttaaa cgtatcaaaa tgttatgaag atggagatgt    73380
cttaactatt cgtcaaattg atgattttcg atcgcatatt gtcacattta ccaaagacga    73440
agctattgcg ctaaagactt atcttgattc tgtcattcca actatgattt caaagtgagg    73500
aaatatgttt atttcaagtg gaagtggttt aattcgcgtt gaatttaaaa atgacatctt    73560
ccttagtcaa ggagatgata ttattaaaat gagttatgat gaaattaaga aaatttgtca    73620
cattcttgaa agtcgtggaa aaggaaatgc tactatcgat ataggtgatt tatgggtgac    73680
actttatgaa gtatccgaag gatttaacat tgaagatgaa acaacatct tagctattga     73740 taaaagaagc gatttgtttg atgtgttaaa agtttatgaa cagtcaaacg gtggaagaaa    73800
agctgcattg atttatcaaa aaccacattc atgcggaact gcttcaatta tttcagatat    73860
tgaagatgaa actgatactt atatgtgtgt tttaaaagct ggtggtgacc gtcatccgga    73920 tttttatttct attcgtcaaa acaatggaga aatttcatta tcaaaatcag aagctgaagc    73980
tatgattaag tatttaacaa ctgttacacc ttcaatgaaa ggataattat gattattaat    74040
gaaaactctt ggcactataa attattcaaa ctgtttaatg atgaatggaa acgacctaag    74100
acactgtgtg catacttttg gtctattgtt atccctacat ttttcgtttc tttttcgga     74160 tgtactatac tcgcaggtct aactattatc tgtgcagaaa tcatgcagaa atggcttatt    74220
tttggtagtt tatggactct tattccatca gcatttatac ttgccatttt gcttgtttta    74280
cttattattg gttcatttgt tattcctgca caactgcatg aaaaatataa agattataaa    74340
tggaaaaagg attatgcttt acatgtagaa aatattgata gggcgtataa aggtttacct    74400
cctattcaac ccaagaaatc tattatcgtc gaatttttaa aagcgcgtaa agctaaagta    74460
tgtcctgtta ttgaatataa ggctgaatga tgaaaacagt aatgaaaagc tattttggta    74520
gtcatcttta tggaacttct actccagaat ctgatgtaga ttttaaagaa atctttgttc    74580
ctcctgctcg cgatattctt attggaaatg ttaaagagca tatgagtaaa aacactaaca    74640
acacatcatc taaaaacact aaagatgata ttgaccatga actatacagt cttaagtatt    74700
tctttaaatt agcagcagat ggtgaaactg tagcattgga tatgctccac actccaccgg    74760
aactagtagt taaatctgat ttgcctgatg tatggaagtt tattcaagac aaccgttctc    74820
gtttttatac gaccaacatg aaatcctact taggatatgt tcgcaagcaa gcttctaaat    74880
acggtgttaa gggttctcgt ttggccgcat tacgtgatgt gttgaaagta gttaatcaaa    74940
```

```
tccctgagca atgggttgat taccaagaag acggttccat taagcagcgt cgaactaaag    75000
ttgaagatat taagcatcgt cttccagaga acgaattctg tgaatgggta ttccataatc    75060
atgagaaaac aggtccacaa acgttctaca ctgtgttggg tcgtaaatat caaacaacgc    75120
tttctcttat tgagcttaag cagtcttga ataaacttga tgctgaatac ggcgaacgtg    75180
ctcgtaaggc tgaagcgaat gagggcattg actggaaagc tctgagtcat gcttgccgtg    75240
gtggactcca actattggaa atttacaaaa ctggtgactt agtctatcca cttcaagacg    75300
ctccatttat tctcgacgtg aagttgggta acatccatt taaaactgtt caagagtttt    75360
tggaagatgt tgtcgatcaa gtagaagcag catccattga agcttctaag aacggtatgc    75420
agcaaaaagt agacatgggt ttctgggatg acttccttga gagggtttat cttgaaaacc    75480
accgaagtta ttataaatga tagggagcct tcgggctccc tttttatttt caaaatttt    75540 tcacaaaaca gtttacaagc ataaagcttt atggtactat acaactatca actgatacgg    75600
atttggagaa taaatgaaa actgtaacta tcaataaggg tatctacttc ggtaaagaaa    75660
tctctggaac ttttgagctc ttaggcgaat ggttcccaga taatgctccg gtagatgcac    75720
aaggagatgg taaagttttt gttgaaattg acggtaaacg tcgcggtgtt tgggtttaca    75780
aatcagatat ttcatatgat ggtgtaaaag ttgaagaagt taaagaatca tatgaagata    75840
tgaaaacccg cattaataaa agatttaatg ttatgggaat gatgacgaat ggtattatta    75900
acggaaatat tcgttcatta attatctctg gcgcagcagg tattggtaaa acgtattctt    75960
tagataaagc tttaaataaa gcaaatgata ttggatacat tgaatataaa agcattaatg    76020
gtaaaatctc tggtattggt ctttatgagc agctttggaa taatcgtgaa gagaattctg    76080
tccttttgat tgatgatgta gatgttttct ctgatatgga cattcttaat cttctaaaag    76140
ccgctctgga cactggagag acccgtaaag tctgctggag cactgcgtct tcttacttag    76200
aagaaaaagg cattgagcgt gagtttgaat ttaaaggaac gattgttttt atcacaaacg    76260
ttgacattga ccgcgaatta gaccgtggta ctaaacttgc tccacattta caagcattag    76320
tgtcccgctc ggtttattta gatttgggtg ttcacactaa tgaagaaatt atggtcaggg    76380
ttgaagatgt tattctttca actgacatga tgcaaaagcg cggtctttct gatgaagaaa    76440
cttataaagc attatcatgg atgaaagtta atgttaatcg tttacgcaat gtttcactgc    76500
gtactgctct ttatcttgct gactttatta tgaccgacaa aaacggttgg gaagaaattg    76560
ctgaggttac tcttttgaaa taattcataa gaggacttct atgacaaaaa ggcagttcag    76620
aaatagatta tatggactgc cattaaaaag atgactagaa ttaaactgat gaatggaggt    76680
agtgatgtta tactcaaagg ctcgtgaaat ttacgaaact aaaattaaag aagcagtatt    76740
tcagttcgca acaacaatgc gatggacaaa tgactgggag tattcaaaaa atcataagaa    76800
gcccatggtg acaagaaagg ctcatatgtt agtgttaata gaccgtgagc agattaaagc    76860
ccgagaagcc ctccagaatc ataaaaaggc tgcctttgaa tggtttatgg ataacactgc    76920
tcctgagacc aagaaagcag tgagcgcctg gttcagtgga aaaaattgtg aaagaagtta    76980
cttttagtgg tttacaagac tgttcctctg tggtactata caactatcaa ctacggagga    77040
acagaaaatg aacgctaaag atattttcaa cttggtaaat tacaacgatg gtaaatttaa    77100
atctgaagca caaagcaagt tctttaatga catctcaatc ggaggtgaaa tcactgttga    77160
tggaggacaa atttacaaat cccgttggaa ttggatcgtt attattgatg agattggtat    77220
tgtagaaatt tataagaata cgaataaaaa tcgtacatta cactggtctc gtgatactaa    77280
```

```
cgaacagtac aaaaaggata aagcatctaa attatctcgt gtaactcaag aagatattga   77340
gttcatcaag aaagatattt taatgtatga taacttaatt gctgaagagc aagctgttat   77400
tgataaattt gacgagatta aagcttctcg tcaaattcct gattttatga agaatcagt    77460 aaatgaacga tacactctca tttcagagcg tattgaaact tacaaaaagc aaagagctga   77520
acgccaaaat actcttcgga agtttgaaga acggttaaag acggtactcg cataaccgct   77580
ttataccaag gatggtataa tggttctaag ccctttaat tgagattatt atgaaacagt    77640
tgataattaa aagattgaat ttattgatat gttgtttatg tgtagtaatt gcatatggtt   77700
attacgcaat taatgattat atgcattata aagattatga tgttactgta gttaatacca   77760
ttacaggaac acaaggaaaa gggtctagtt tatcgtttat tgccgtatat gaactcaaag   77820
acggttatag atttagtgaa tatatttccc cagagatgta ttcttcaata gaaaaaggtg   77880
ataatattac tgtaagttta cgtcctttcg acgtaaaaca gacatggttt gataatatta   77940
tttggttctt tggaatggca ttagttcagt ctatatgcgg tacttatata gtctgttcaa   78000
tcttatttcg cgtaattagt aaaattgagt gaggaaaata tgtcagtagt aattaataat   78060
gtcaatgcag taattaaatc tttagttaat aaaaaaaatg atgaatgaat ggactgtatt   78120
tcgccgtgga gagccggata aattttttca tagatttaac ccaactttgg atttgaatgt   78180
tattgacaga gatgttcatg cagaaatttt agataagttt aaagttgata ttggatttgg   78240
attagaaaaa catttgcagc gaacaaatgg gtctggaatg agtttatcta atcgcattat   78300 gaaagcccctt aataaaattg gagcattgtc tcgtattaac gcgagtgaaa tccttcgtaa   78360
ttataataaa ggatatgacc tttatggtcg actaatgcca aaattatcat tcgatcaaat   78420
gattgcggat ttgtgggaaa atcaaagacg attattagca ttaggcgctc gattagctaa   78480
aggtctagat aaacaaatga tttttaagac taataataca gaagacctta aatgctttaa   78540
atttagtact cgtggcgatg attattacat cagagctcac tctacagatt atgttaatat   78600
ggggcatcat ctctgtttag cttttgaagt tttaaaagaa tctggaacat tagaatattc   78660
atctggtgca aaatgcccta ttggttcaag ttgtatttta atttatcgcc cggatgaatc   78720
cagttcaatt acattgccta caaaacctgt accagttcat agtaacgaaa acatttga    78780 acaaattgat tattttaata aacagattga agagctgaat atttctattc aacaatatga   78840
tgatgaaatt ttcagactat ctggactgaa tagtaaagct aaatctgagc gtgaaaagtt   78900
aattaaaatt gttgatttac ttaaatctta aggaacacca tgaaaactcg ttctcaaatt   78960
gaagatatgg ttcgtactgc cagcgatact cgtaatgtta tgcattttt gtgtgaaaat    79020 aatttagacc ctgataaagt taatcgtgct attcatcact ttaaatatct aaatagcagt   79080
gaatgggtga gtaattttag taaagcgggg tatattacac aaatgactgc tcgtgagcag   79140
ctcacagatt tctgtaaaac tattgattat aaaaatcctc tatttgttca aggcgttggt   79200
caaagtaagg tcgatttatc atctggattt ttcaatccaa atcattatcg tattgaatgg   79260
agatttattg ctctattccg taaacaatta aagcaaattt tgtcgacggc tagtcgatta   79320
aaaggttctg acattaactt aaagaacctg aaatttgatg gttatactct tcagatggaa   79380
gtaagaccat taaagaaaaa taacagaact gcacgaatta gctttaaacc taatacaaaa   79440
aattctcttt caatttgcga atgccttaaa tcgcagttga cagaagcatt taagtatatg   79500
gatgttgttg ccgctgttca gtctaagatt ttacctcgtt ttgagcgatt taaattagac   79560
acaacaacat atgaacttga tatgatcgtt tcatttaaat acgattttt gagaaaggac    79620 gaagtcccgc aagagaaaaa gcaggaagtg caagatatct taaatttatc caattactca   79680
```

```
tcaaacgatc ctaaattttg gatgtatagc tcaagcaata tagatgcatg taaacttaat    79740
aaagtgagtt ttcttcctac tgaaaattca aattttaaac ctgtagaaaa atggcacgcc    79800
gatgcgattg agaagtctct taaggcagta gatgatgaac tcgttaaagc gaccaatgaa    79860
gtgctagaag ctgaaaaggt gttagaacaa gctcagtcaa gggttcaaaa tctgacaaag    79920
caacgttcta aactgaacaa tgcactaaat gcactgaact agtttacttt gccacaagga    79980
tgtggtataa tgttcttact ttctactgag gagattaata tgactcgtaa cgaatatatc    80040
aaatcgttca atagcgttat tgatgataaa gttaaaccta tgtctagtca gaatagtgtg    80100
atttctatta tcaatcaatg gatcaataat actagtgcaa gtattgtttc ttccgacaaa    80160
tttatttatg aagtttgtga aatttctagt cgtacatata aagatgacat taaggaaacc    80220
tttaaaggtt ctcgtcttct ttcatactta gtcaacagag atattcttag taaatttggg    80280
aaagaaatta acgaactaa agatgtagta ggatataatt ggttcggtga tgttaattct    80340
tatcatctta ataataaaga agaccctgag aatatttta ctcgtcgttg gattagtaat    80400
ttcagacttt tcaaaggaca aattctaaaa tcagcttcta aattatgtta tggcgattat    80460
cgtcaaattc atcctttggc ttctgatatg attatcgtaa aagaaaatga gcttgataaa    80520
aataaagtag ctatttttgt gaattatgga tttttacac caaacgctaa ccaaaagaat    80580
attaataaat ttttctcaat tgctagcact ataacttatc aattgagagc ggctttgggc    80640
tgtatggaaa ctgtaaaaag tattcataca tatcctttca aaatatgtg tggttgggaa    80700 ggatataaaa ttataattag ccttcgtgaa gtgaaatgtg cgtactcacc gactgataaa    80760
gaaatttacc aacaaaaatg tgaagaaatt gtgaatactc ctaaagaaga aactacccctt    80820 gaggaactaa tggataatct tgatgattca cctgaaccgg tagaaattcg tccagaagtt    80880
attgcattag aaaaagctta taggaagtt ctagaaattt ctaataaagc gcagaaagaa    80940
tatgagcagg ctaaaaggat ttgggaagaa tctgttaatc gcctggatcg tcttgaacaa    81000
gctttacaat taattaagta atttaaagcc aaggatggct cggagtataa atcattaacc    81060
aagtgagaag aacatgaaaa ctcgtaaaca ttatattgat tattttgaca gtcttattac    81120
taaacaccgt aattatcaga tcggacacag agcagtaatc aataatattc ttcgtgattt    81180
ccttcaatat gttggccagg aaaatcatat ctgtaaagat actcaaaacg cttattctca    81240
ttcgttaggc aatttgcttg aatggtttaa acgttctcgt atgttatctt ctactgtagc    81300
tcgcgataac attaaaaaact ttatgaagcc gagcttcatt aaatctacga catctataac    81360
cgatttggtt gaatttacta ttgttaacga tgttaaaaag acccatttgg ctgattggtt    81420
atctaccatt cctgaaacta aatttgctga taaatttgct tgtcaattca atgcccaagt    81480
gaatatgctt ttaagcatg ctcgcaaact atttaccgca ggcgatgacc gtacaaatac    81540
agttcatgtt aaggactggg ttattgctga tgaagtaaca cacaagccag gtggttcatc    81600
agtattaatt aatatccagg ttccttatta ttactcacgt aatctcggca ccatgacagc    81660
taaagaaatt aataagcaca acaaaactat tcgttcgttg tcttataaac ttcgcatgat    81720
gttaaaaatt atggacgtag tggaaatgta tgatgaaacc gaagataatg gttcaatgtt    81780
atacagctca cgcattctaa ttaaactgaa gaaccctaat acgtataagc cagttgtaaa    81840
agaacctaaa gtagaaaagg ttgataacct gagcgaagaa cgtgaatatc tcaatgctcg    81900
tttaattgaa gttgaagccc agattgccga acacaccaaa ttgttaaaag ctcttaatgc    81960
aaaagcaaat ggtttacgta atgctattga ggtattgaaa tgaaaaagcg cttattagaa    82020
```

```
gatattgcag cttcaagtaa ttccagtcta attaaaatta ttatggctgg tgaagaagac    82080
gatctggaaa tgcgtggaaa gattcatggt tgtgacgatt tagattttaa acctccagca    82140
tgggatgcta ttatggctat ggttgaacgt cgcgaaaggg cttctaaaaa cgttcctaat    82200
tgccctgaat gcggtactga acaggttcaa ttaattcatt ggcagactag tattcttcgt    82260
tataaatgcc gtcattgcaa acaccgattt aaccgagaag aaaatgacaa agcgtaaaga    82320
atatatggag actgctgaaa aggcagtccg tgaattagca atagcgtatt ataatgaaca    82380
tggtaaattt cctgatagat acagcgtgct taaatctgct ttaactcgtt catataaaaa    82440
tatgctatca gaagtaagtg atattatata caaacataaa gaacaaacgg gccaaagtct    82500
tgattacgac gagactttta aacaagtact aggaattaag gaataatatg tttaaagtat    82560
atggttatga tagcaacatc cacaaatgtg tgtattgcga taatgcaaaa cgtcttttga    82620
ctgtgaagaa acagccgttt gaatttatca atattatgcc ggaaaaaggt gtttttgatg    82680
atgagaaaat cgctgagctt ctgacgaaac taggtcgtga tactcaaatt ggtttgacaa    82740
tgccacaagt atttgctcct gatggaagtc atattggtgg atttgatcaa ttgcgggaat    82800
actttaaatg atgctcgaaa gaactgatta tatccatgac taccgcggaa gcgcggtata    82860
tgtaggtgat gaggttgcag tttattatgg atatggaact ttgatgacag caaaggttat    82920
tcaaattaaa aatggccgcg ctaaactcga agtttattat tctaatggtg aaaagtctat    82980
ttctaaatgg aaatatggcg attgtatggt caaactgggg taaatatgat ttacgatatt    83040
agtgtatcaa gagctccatc aatggttact attccagctg aagaactgga tcgtcttcag    83100
aaaattgaag aacttctttg ggaaattgaa tctgatttgc catcaggact agaatcctgg    83160
attgattatg aagaacttaa taaattgcga aattaattgg tgaaaaatga atattgaaaa    83220
taaattagat gttgatgcag ttctgagcga aatcatcgaa gaccatgatg gattttcaga    83280
aaattatgat ttcgatttt cggattatct aaacctgtc gaaatagaag attgggtaca    83340
agatggcaaa tgccaatatc gtcagtgtgt ttattttagt ccaaaacata acgttcatgt    83400
gtctgtaaat gaaactcgct caggttctta ccattctgac tggtattatg cagttccgac    83460
tgttgaacta gtcgagcccc atgaacgtgt agtaactcag acaatacgag aatggattac    83520
gctataaaac cttggtgggc ggctagatgg gaaactgtag agccagagcc ggaagaaccg    83580
gtttacactg atgaagaaac agtatataat gaaccaacga taaacgactt aattgatatg    83640
gagatgggat atgattgcag tagataagtg gtttaaaatt aatcgtgctg ataaagagct    83700
gtgtaattac tggccggaac ttggtgcagg tactgtctttt aaagttcgtg aacttgtaaa    83760
agaatgtgaa gatgatatag aacctgatac tggaattatt gaaattgaac tttctggtgg    83820
aaagattatt aacatctacg ataagccaac tgcctattgg tgcttatgga atactgaatc    83880
agtagaaaat ggcgaaattg aagaggtcgt agaacgagtt gatcaagtta ttcggaaacc    83940
tgaagccgct tttcaaggtg aacgtatttc atacgcatta gctaaattag ctgcacaaga    84000
aaataacgat ggttatgaag gaaatttaat gcaagctgcg gcagaatata ttgaatggct    84060
tgaaactcaa aattctttttt ctgaccgagc gttttaatga aaccgaatt aatttatact    84120 gaaaagttaa atggtggtaa ggtttggaaa ctttttatta aaggaagtca taccgactct    84180
aatatgacca cttgtgtagg aacttattct cgtcctacta aaaagatgat tcggcaatat    84240
aagcgattgc atcgaatgtt ttacaatact tgaaaataat aaatacccctt atctattcaa    84300 ggtaagggtt ttattatgtt attgactggc aaattataca agaagaaaaa acagaaattt    84360
tataacgcac aaaacggtaa atgcttaatt tgccaacgag aactaaatcc tgatgttcaa    84420
```

```
gctaatcacc ttgaccatga ccatgaatta aatggaccaa aagcaggaaa ggtacgtgga   84480
ttgctctgta atctctgcaa tgcagcggaa ggtcaaatga aacacaaatt taatcgttct   84540
ggcttaaagg ggcaaggcgt tgattatctt gaatggttag aaaatttact tacttattta   84600
aaatccgatt acacccaaaa taatattcac cctaacttcg ttggagataa atcaaaggaa   84660
ttttctcgtt taggaaaaga ggaaatgatg gctgagatgc ttcaaagagg atttgaatat   84720
aatgaatcta acactaaaac acaattaata gcttcattta agaagcagct tagaaagagt   84780
ttaaaatgac aattgaaaaa gaaattgaag gattgattca taaaactaat aaagaccttt   84840
taaacgagaa tgctaataaa gattctcgtg ttttccaac tcaacgggac cttatggctg    84900
gtattgtgtc taaacacatt gccaaaaata tggtcccgtc ttttattatg aaagcgcatg   84960
aaagcggaat tatccatttc catgatattg attattcccc tgctcttcca tttactaatt   85020
gctgtttagt agatttaaaa ggaatgcttg aaaacggatt taagctcggc aatgcacaga   85080
ttgaaactcc taaatcaatc ggcgttgcca ctgcaattat ggcacaaatt actgcacagg   85140
ttgcttccca tcaatatggc ggaacgactt ttgcgaatgt agataaagta ctttctcctt   85200
atgttaaacg cacctatgca aaacatattg aggacgcaga aaaatggcaa atcgctgatg   85260
cgttgaatta cgcccagtct aaaacagaaa aagacgtata cgatgcattc caagcttatg   85320
aatatgaagt aaatactctc tttagttcaa acggacaaac gccttttgta acaattacat   85380
ttggtacggg aactgactgg actgaacgaa tgattcagaa agcaattctg aaaaatcgta   85440
ttaaaggtct tggtcgcgat gggataactc ctatttttccc taagcttgtt atgttcgttg   85500
aagaaggcgt taatctttat aaagacgatc cgaactatga tattaagcag cttgctctag   85560
agtgtgcaag caaaagaatg tatcctgaca tcatttcggc taagaacaat aaagctatca   85620
ccggttcatc tattcctgtt tctccaatgg gttgtcgtag tttcttgggc gtatggaaag   85680
attcgactgg taatgaaatt cttgatggac gtaataatct tggcgttgta acactgaatc   85740
ttcctcgtat tgcgttagat tcttatattg gaacacagtt caatgaacag aaatttgccg   85800
aattgttcaa tgaacgaatg gatttatgtt ttgaagcatt gatgtgtaga attagttcct   85860
taaaaggagt taaagctact gttgctccta ttctttatca agaaggtgca ttcggggttc   85920
gtcttaaacc tgatgacgat ataattgagt tatttaaaaa cggtagaagt tcagtgtccc   85980
taggatacat tggtattcac gaattgaata ttcttgtcgg tcgtgacatt ggacaagaaa   86040
ttttaactaa aatgaatgca catcttaagc agtggactga agaactggtt tttgctttta   86100
gcttgtattc tacacctgct gaaaacttgt gttatcgctt ctgtaaactc gataccgaaa   86160
aatatggaag tgtaaaggat gttactgata aaggctggta cactaacagt ttccacgttt   86220
cagtagaaga aaatattact ccgtttgaaa agatttctcg cgaagcacca tatcatttca   86280
ttgcgacagg tggtcacatt tcttatgttg aacttcctga tatgaaaaat aacctaaaag   86340
gtcttgaggc tgtatgggat tatgctgcac aacatttaga ttattttggt gttaacatgc   86400
cagtagataa atgttttacg tgtggaagta cccatgaaat gactcctact gaaaacggat   86460
ttgtttgttc tatttgtgga gaaactgatc taaaaagat gaacacaata agaagaacat   86520
gcggctattt gggaaatccg aatgaacgcg gatttaatct cggcaaaaat aaagaaatca   86580
tgcatagggt taaacaccaa tgaattatga tagattttat ccttgcgatt tgtgaatga   86640 taaattatct ttaatatttg aagaaaataa tgatttacta ttgtcatatg ttgatttgat   86700
aacaaaaaat tataataatc ctaaaataaa aggaaaaacg gaagcacatc acgtgcttcc   86760
```

```
caaatctata tttcccgaat ataaaacaga taaatggaat attgttaatt tgtcatatta    86820
tgaccacgcg ttagctcatt actatttagc taaaacaagt aatagtaaaa tgtgttatgc    86880
ctttcataga atgataaact cgaataccga tagatttaat acagatgaat tggatgaaat    86940
tcttaaattg tattccagtg aaaaggaatt atttcaccgc tctatgtcaa aattatcgaa    87000
aaatatatgg aaggatgacg atttttagaaa aagacataga gaactaacta agttagcaat    87060
gcaaaaacct gaagttagaa ataaaacttt attaaatttg tcaaatgcaa tgaaaactga    87120
cgaagttaga aataaaattt ccaggctaac taagttagca atgcaaaaac ctgaagtaaa    87180
agaaaaacat agaaattcat tgaggttggc gtatgcaaat cctgaggtta tgaaaagaaa    87240
acatcaacgt cttcgagaaa aatatactct taatttattt ggcgcatata aagatggtgt    87300
tcttttaaaa acatttaatt atataccaga cgcagcaaaa tatttaata tttctagcaa    87360
aggaaatatt ttaaaatgtt taaatggcga acgtaaaagt gttgaaggct ataattggaa    87420
atatataaat gaattatgac agaatatacc cgtgctgctt tgtgaatggc cctggatgca    87480
ggaccgttct tttcgttacc ggttgtttgc ataaatgcga agggtgttat aataaatcaa    87540
cgtggaacgc tagaaatggt gttccattca cgggtgaaac actagaacaa ttaattgaat    87600
gtttgaataa tgattatata gaaggattaa ctataactgg aggagaccct ctctatcctg    87660
ataaccgaga tgatgttcat tgcattgttc aaacagtaaa aaatctttat ccaaataaaa    87720
gcatttggtt gtggacagga tataagtttg aagatattaa acaactagaa atgcttaaat    87780
atgttgatgt tattattgat gggaagtatg agaaaaatct tccgactaaa aagctgtggc    87840
gaggatcaga taatcagcga ctttggtcaa ataccgatgg ggtgtggaaa catgattaaa    87900
ttgaattata ttatggacac tataaatgat atgattttc attttggtcc agaattttat    87960
tcgcaatata gtttagtgct tatcaatgct tggttaatca attaagggta aaatatgtat    88020
aaatttcgca aaggtttagc tgattttctt acaactgtaa cattctttct gtttatggca    88080
gttggagcta ttttccttat tccttttatt gctatatttt tcgtgattag tttgatttct    88140
ccagaaaaag gactgtcttc tagcgagttc aatgagcgtc tggataaaat tactaataag    88200
ctgaatgctg ctcttagtaa ggaatagttg tgaaacagaa caagattgaa gtctatggaa    88260
ttccagatga agtaggtcgt tgtcctggat gtcaatcagt tacaaaactt ctaaaggagc    88320
tcaatgctcc ttttactttc tataaagttc ttacaaataa tggtaagatt gagtatgatc    88380
gtccactgat tgtatctctt gctaaacgcg ctggattcac atctcttaac attcgttatc    88440
cagtcatttt catcaatgat tctagacaaa agaacattaa acacttcaaa gaaactctca    88500
tttcacttgg atatgataga gatatcatag aagactaaga tgggccctct gggcctttct    88560
ttctcacatt ctgtatatta ccattctaac tatcgttccc ttcttatcat tccctaaaat    88620
aattttcaca aagttgttta caagaagttc aaactgtggt attattaaca catgaattgc    88680
ctttgaggaa ttgatatggt tgtggttgat aaagaaatta aaaagggaca gtattatttt    88740
attaatggta atgttgttcg tgttacttat gtaaacggtt ttgaagttta ttatcttata    88800
ctcaagttac ataaacagat gatttgtgac cgtgctgtat ttagttcagt tgctaaggaa    88860
attaaactcc atgggtaaaa catatcgtcg taaagattta aaagtacgtg attatgacta    88920
tttcggaaag cgtaaagctc ctgatggtgt aagtcataaa gatatggttg aaaacatttt    88980
tcgctctgat aaatggcgta gaatgaaagg cattgattca gaagttaaag atgagttaaa    89040
tcgtcaattg cgcggtgaag taagaaagtt gaaaaaatca gtttacattg acgatgattt    89100
tgattacaat acttcccaac gagttgctaa gcgcaaatca aacgagtgtt atcgttacag    89160
```

```
ctgaggaaaa tatgaatatc aaacgcatgc tttttaaaca aggattatac actttaaatg   89220
ttgctccaaa aggcgatacg accaagtggt cagtaaatga ctggattaaa tttattgatg   89280
aaaatggtaa ctggaaaatt taaatgaatc ctgaatctaa attatcgcaa cgaattgctg   89340
aagctcgtcg tcagttcttt gaaaatatga tagcccaagg tattgatgac gaaattttc    89400 taaactggtt ttggaatcac aaatattcaa aatgcgcagg agcaatatta atatcagccg   89460
caatgatgta tgaaggctgg aagggtgcca aacagtttag ctaagggctt cggccctttt   89520
tggataataa aattttaatg taattgagga taatgtatga ctattcaaat taaaaacgcc   89580
atcaattctt acgcatatga taaagtagtt tctttgctag aaaaaggcga tattgtaact   89640
cctcaaattt tggataaatg ggaaaaagag cttcatcaga cgatgaaaca gaatgatcag   89700
aaaattggtc gcaatactgt ccgtgaattg ttggttcaat atatcttgtc agaatttgat   89760
gttaaagctt ttggcgtaga atctaaagct tatcaaaagc atgaaatttc cgataaaact   89820
attcgtcgta tgaaaaatca acgcaagaaa aaatttgctg acctgaaaat tgctaaggta   89880
tgaatatgaa cgaagctctt attaacgatt tgcgtcttgc cggatatgaa gtaaatacaa   89940
acggcattgg tttaactcaa attgaaggaa atggattcat ccttgagtat gaatttagcc   90000
aatggtggtt atacgctaat tatggcgaat tgattgaata cgttgaccag tttgattcac   90060
tagatgcagc tcttgaagcg gctaagttga tgaatgcatg aaatttatta atatttctat   90120
tactattgaa aattatggca ttttctatgt tgatcaatac atgaaaattt cattttccc    90180 aaataagact ggtgttggat attgggaaag ccatgtttct gaattaaatg aaagtgaata   90240
tgctagcaca catgaaaagt ttttagactt tttatatcat gctgatttaa ctagtcatta   90300
tatagatatt catgaattta aaaagatgat ggagaaagtg ttccaggcat actgcttact   90360
tagataactg atatcctcta tgctttaaga tagatcttca aatattatga tataatagat   90420
ctatgaattg agctaagagg tgaaaatgtc agaaactaag cctaaatata attacgtaaa   90480
caataaagag cttttacaag ctattattga ttggaaaaca gaattagcaa ataataaaga   90540
cccaaataaa gtagttcgtc agaatgatac tatcggattg gccattatgc ttattgcaga   90600
aggcttatct aaacgtttca acttttcagg atacacccaa tcctggaaac aagaaatgat   90660
tgcagatggt atagaagctt ctattaaggg gcttcataat tttgatgaaa cgaaatataa   90720
aaacccacat gcatatataa ctcaagcttg ttttaatgca ttcgtccaac gtattaaaaa   90780
agaacgtaag gaagttgcaa agaaatacag ttacttcgtt cacaatgtct atgacagtcg   90840
tgacgacgat atggttgcgt tagtagatga aactttatt caagacatct acgataaaat    90900
gacgcattac gaagaatcaa cctatagaac accgggggct gaaaagaaaa gtgttgtaga   90960
cgattctcct agtttggatt ttttatatga ggctaacgat taacctctcc ggattcttgg   91020
aagaaatacc tgaagttgaa gctattccct atttacttaa aatgtatctc agggaagttt   91080
tagctcttga cattgatatt gatccagaaa atccgtatga taccgctttt aaatctaatg   91140
gtgtagaatt aaactatcgg tatcatttaa cagatgatga tttttatttt atattagaga   91200 aataaatatga ctgataaacc cgaaattaat gatgaagtgg aaaagcttat ttcttctatt   91260
gaagaaaaga accgtcttga agcagaaaga aaagcaaata agttattgtc taaaaacaaa   91320
cgcgaactga accgtctttta taagcacgct cagattgcag ctgaaaacaa taattttgct   91380
caatacgaat atgctatcaa gaaaagtcgg atattctaa aacagccata taacgatgaa    91440
ctcattagta ttctttggaa gactactaga tcgcagattg aggatatgat tgatgcttac   91500
```

```
acacgtaaaa ttcaagcgtc ttaaaattaa tgcaggattt actgaatctt tgaatggtca   91560
tctttgtgtg aaaatttctg aaaaagaata ccacgatagt tcaattaaag aagttaatcc   91620
tcctattgta agagcagacc ctaatatgaa agtgtgggtt gattcttatc aagtcaaaaa   91680
atggtggcaa ctgtgaaaga tgaacaccca gacttctgaa atagattata ataaaattcg   91740
ttcctctaaa gtagaaatga tgagacgctt taaagagtct catgataaag ctaaagcaga   91800
aggaactata acatataagc gtataaaatt tagaagctct aatgagcctc tgtatggtgt   91860
attatgcgga taggagcttc ggctcctata ttgctttata aattttggt aaaataaacc   91920 aaaacaatga ggatattaaa tgaaagtatg cattttatg gctcgaggtc ttgaaggttg   91980
cggcgtaact aaattttctc tcgagcaacg tgattggttt attaaaaatg gtcatgaagt   92040
aactttggtt tatgctaaag ataaatcatt tacccgtaat tgcgcgcatg attataaatc   92100
attttcaatt ccggttttat tggcaaaaga atacgataaa acacttaagc tggtaaatga   92160
ttgtgatatt ctaattatta attcagttcc tgctacttca gtagaagaag acactattaa   92220
taactataaa aaaattattg ataacattaa accttcagtt cgtgttgtag tttatcaaca   92280
tgaccattct tctctttctt tgcgccgaaa tttgggatta aagaaactg ttcgtcgagc   92340 tgatgttatt tttagtcatt ctgataatgg cgattttaat aaagttttga tgaaagaatg   92400
gtatccagaa acggtttctc tgtttgatga tattgaagaa gcaccgaccg tatataactt   92460
tcagcctcct atggatattg cgaaggttcg atcaacctac tggaaagatg tttctgaaat   92520
taacatgaat atcaaccgtt ggattggtcg tactactaca tggaaaggct tttatcagat   92580
gtttgatttt cacgaaaaac atcttaaacc tgctgggcta agtactatta tggaaggtct   92640
ggaacgttct ccagcgttca ttcctattaa agaaaaagga attccatatg agtattatcg   92700
tcttcatcaa gtagaccaaa ttaaaattgc tcctaatttg ccaacgcaaa ttcttgaccg   92760
ttatgtaaat agcgagatgc ttgaacgcat gagtaaatcc ggatttggtt atcagttgag   92820
taagttggac aaaaaaatatc tacaacgttc tttagaatat actcatctcg agcttggtgc   92880
atgtggaaca attccagtat tttggaaatc tactggtgaa aatttaaaat tccgcgttga   92940
taatactccg ctaatttcac atgatagtgg tatcgttggg tttgatgaaa atgacatgga   93000
atcaacattt gagcgtatta agaactgtc atctgaccga actctttatg accgtgaacg   93060
cgaaaaagct tatgaatttt tgtatcagca tcaagattca agcttctgct ttaaagaaca   93120
atttgacatt attacaaaat aaagggcttc ggccctttag ctttatacgg agtttgatat   93180
aatgatattt cttggatatg tgatacttt tctcgcattt tatctattca ctagagcatg   93240
ttggattggg ttctttagca ctccagatgg atttatttca ataattttat tttgcatttc   93300
aatgacggtt cttgatatat gaaaatttta aatttaggtg attggcatt aggtgttaaa   93360 gccgatgatg agtgggttca atccattcag ttggatggaa ttaaacaagc aatagaatat   93420
tctaagaaaa atgaattac tacatggatt caatacggcg atattttga tgtgcgaaaa   93480 gcaatcacac ataaaactat ggagttcgct cgtgaaatag ttcaaatgct tgatgacgct   93540
ggaatcacat tacatactat tgtaggaaat cacgatctcc actacaaaaa tgtaatgcat   93600
ccaaatgcct ctactgagct tttggctaaa tatcctaatg ttaaagtata tgataagcct   93660
gctacagtag attttgacgg atgttgatt gatttaattc cttggatgtg cgaagaaaat   93720
actggtgaaa ttcttgaaca catcaaaact tcatctgctt ctttttgtgt tggtcactgg   93780
gaactgaatg gatttatttt ttataaagga atgaaatctc acggtcttga acctgatttc   93840
cttaagactt ataaagaggt gtggtctggt cacttccata ctatctctga ggctgctaac   93900
```

```
gtcagatata ttgggacacc atggacacta actgcaggtg acgagaatga ccctcgcggg   93960
ttctggatgt tgatacaga aacagaacga atggaattta ttccaaacaa caccacctgg   94020
catcgtcgaa ttcaatatcc atttaagggg aaaattgact ataaagattt tacaaatcta   94080
tcagtacgtg ttatagtaac tgaagtagac aaaaatctaa cgaagttcga atccgaacta   94140
gaaaaagttg tgcattcatt acgagttgtg tcaaagattg ataactctgt cgagtcagat   94200
gatagtgaag aagttgaagt tcaatctctt cagacgttga tggaagaata cattaatgca   94260
attccagaca tcactgattc tgatcgcgaa gcacttattc aatatgcaaa ccagttatat   94320
gtagaggcaa cacaatgact tttgatgaat ttaaaaatgt tatgatgagt cagcattttg   94380
aatgcgaagt aaaagatgat attgggcata agaaattat tgaatattgg tttgaaccgc    94440
tagaggttga agataattgt attaaaaagg ttacggtctg cactgattgg gccgtatctt   94500
ttaacttcaa cattttagat aatgacacac ctaaatcatt acaagatatg ctgtatctt    94560 gtattaagga tgcatactgt gaagttttcg acatttgaca ttaacgatga attcatagca   94620
aatattgatt acaccgaaga agattctaga tatgttggaa taatttatat cacatcaaaa   94680
gcagcacaag gtgttgtttg catggctgaa tttgatgaat acttttaga ttatgatgat    94740 atgatagaat ggtctaaaag atacattaaa aggaatcttt tgtgaagaat tttaaactaa   94800
accgagttag gtatcaaaat ataatgtcag taggtggaaa tcctattgac attcaactag   94860
ataaggttca aaaaactctt attactggac gaaatggcgg tggtaagtct actatgttag   94920
aagccatcac atttgggctt tttggcaagc catttcgtga tgtaaagaaa ggtcaattaa   94980
taaacagcac aaataagaaa gaactttag ttgaactgtg gatggaatat gatgagaaaa    95040
agtactatat caaagagga caaaaaccaa acgttttcga aatcaccgtt aacggtacac    95100
gtcttaatga atctgccagc agtaaagatt tccaagcaga atttgaacag cttatcggaa   95160
tgtcatatgc cagtttcaag cagattgttg tccttggtac agcagggtat accccttttca  95220 tgggtttgtc aacccctgca cgaagaaagc ttgtggaaga cctgctcgag gtaggaacat   95280
tagctgaaat ggataagctt aataaagcac taatacgtga attaaattca caaaaccaag   95340
tgcttgatgt taaaaaagat agtattatcc aacaaattaa aatatataat gataacgttg   95400
aacgccagaa aaaattaact ggtgataacc ttactcgtct acagaatatg tatgatgatt   95460
tggcaaaaga agctagaacg ctaaaatcgg aaatagaaga agctaatgaa agattagtta   95520
atattgtttt ggatgaagac ccgactgatg catttaataa aatcggccaa gaagcatttt   95580
taattaaatc aaaaattgac tcgtataata aagtcattaa tatgtatcac gaaggtggat   95640
tatgtccaac ctgtttgtca caattaagtt ccggtgataa agttgtttct aaaattaaag   95700 ataaagttc tgaatgcacg cattcgtttg aacagctttc aacacatcgt gataatttaa   95760
aagttctcgt cgatgaatac cgagataata ttaaaaccca acagacgttg gcaaatgata   95820
ttcgcaataa aaagcaatct ctaatcacga ctgtagataa agctaaaaaa gttaaagcag   95880
ctatagaaaa agcatcatcc gagtttattg accatgctga tgaaatagca ctgcttcaag   95940
aagaacttga taaaattgtt aagacaaaaa ctaatttagt aatggaaaaa taccacagag   96000
gaattttgac tgatatgctc aaagattctg gtattaaagg tgctattatt aaaaagtaca   96060
ttccattatt taataagcag attaaccatt atcttaaaat aatggaagca gattatgtgt   96120
ttacattaga tgaagaattt aatgagacaa ttaaatcccg tggtcgtgaa gattttagtt   96180
atgcttcatt tagtgaaggt gaaaaagcgc gaattgatat tgctcttta tttacttggc    96240
```

```
gtgatattgc ttctatcgta tctggtgtta gtattagtac attaattctt gatgaagtgt    96300
ttgatgggtc atttgatgcc gaaggtatta aggtgtagc taatattata aattcaatga     96360
aaaatactaa tgttttata atttcgcata aagaccacga cccgcaagaa tatggtcagc     96420
atcttcaaat gaagaaagtt ggtcgattta ctgtaatggt ttaatttata agagattatg    96480
ctttaattta ttagagtata atctctatgg aggaaaaaca tggaatattc aactggacag   96540
catctattaa ctattcctga aataaaacga tatattctga gaataatttt ttctaatgaa    96600
gagcatatag ttactgaatc tatgcttaag aatgcattta aatcagaata tacgaaaata   96660
atgtccaaca ggaatgaagc ttggactgtt actgattatt atgactaaag gtgtattatg   96720
actaaaatta ctgtgaatta tactgttgat gtaaaagata ttcagccaaa acacgtgcgt   96780
tctgaatcaa atccgcaaaa ccaaaataaa attcgtcgag catgggtttt gtctctttct    96840
gataacgcaa tggaagttat tcagaataaa attaaatctg cacctgctcg tcatgcgtat    96900
tatgaagcta tcgatcgtga agtgagtgat aaatggattg aactaatgcg caaacatacg   96960
acagaatctc taaatgctgg tgctaaattt attatgactt catgcggtga acgccttgaa    97020
gatgattatt gcggtaatgc agatgaacgt ctaattgttg ctgctcaaat tgttgcagaa    97080
acaattgctg ctgattttaa tcgttaattg ctttattaaa ttagttataa aattaaatct    97140
catttgaatt gaaggaaatt acatgaaact gtctaaagat actactgctc tgcttaaaaa    97200
tttcgctact attaactctg gtattatgct taaatctggt caatttatta tgactcgcgc    97260
agttaatggt acaacttatg cggaagcaaa tatttccgac accattgatt ttgatgtagc    97320
aatttacgat ttgaacggtt ttctcggtat tctgtcccta gttaatgacg atgcagaaat    97380
ttcccagtca gaagatggaa atattaaaat tgctgatgcc cgttcaacaa tttttttggcc  97440 tgcagccgat ccgagtacag tagttgctcc taataaacca attccattcc cggtagcatc    97500
tgttgttact gaaattaaag ctgaagacct tcaacagctg ttgcgtgtat ctcgtggtct    97560
gcagattgat acaattgcta tcacagtaaa agaaggtaaa atcgtaatta acggttttaa   97620
taaagtagaa gattctgctt tgactcgtgt taaatattct ttgactcttg gtgattatga   97680
tggtgaaaat acatttaatt tcattatcaa tatggcaaat atgaaaatgc aaccaggaaa   97740
ttataaactt ctgctctggg caaaaggtaa acaaggtgct gctaaatttg aaggtgaaca   97800
cgcgaattat gtagtagctc ttgaagctga ttctacccac gatttttaat agagggcttc   97860
ggccctttat aatttacact aaaacttgaa tgaggaaatt atgattactg taaatgaaaa   97920
agaacacatt cttgaacaga aatatcgtcc atctactatc gatgaatgta ttcttcccgc    97980
ctttgataaa gaaacctta atctattac aagtaaaggt aagattccgc atattattct     98040
tcattctcct tctccaggaa caggtaaaac aactgtagca aaagcattgt gtcatgacgt    98100
aaatgctgat atgatgtttg tgaatggatc agattgtaaa attgatttcg ttcgcggtcc    98160
tttgaccaat tttgctagtg cagcttcatt tgatggccgt caaaaagtaa tcgtcattga   98220
tgaatttgac cgttcaggat tagcagagtc tcagcgacat cttcgttcct ttatggaagc   98280
ttatagttca aactgtagca ttattattac tgctaacaat attgatggta ttattaaacc   98340
acttcagtca cgctgccgag ttattacatt cggtcaacca accgatgaag ataaaattga   98400
aatgatgaag cagatgattc gtcgattgac tgaaatctgt aagcgtgaag gaattgctat   98460
agctgatatg aaagttgtag cagctttggt taaaaagaat tttcctgatt ttcgtaaaac   98520
tattggagag ctcgatagtt attcatctaa aggtgttttg gatgctggta ttttatcact   98580
ggttactaac gatcgtggtg ctattgatga tgttcttgag tctctcaaaa ataaagatgt   98640
```

```
taaacagctc agagctttag caccaaaata tgcagctgat tattcgtggt tcgtaggtaa    98700
acttgccgaa gaaatctata cacgcgtaac tccacaaagt attattcgta tgtatgaaat    98760
tgttggtgaa aataaccagt atcacggaat tgcggctaat actgaattac atttagcata    98820
tcttttcatt caattagcat gcgaaatgca gtggaagtga tatgagctta tttgaagatg    98880
atattcaatt aaacgagcat caagttgctt ggtattcaaa agattggaca gctgtccaat    98940
ctgctgctga ttcttttaag gaaaaagctg aaaatgaatt ttttgaaata attggagcta    99000
ttaataataa aactaaatgc tctattgctc aaaaagatta ttcaaaatac atggttgaga    99060
atgcattatc acaatttcct gaatgcatgc cagctgtata tgctatgaat ttaattggat    99120
caggtttaag cgatgaagcc cattttaatt atctgatggc tgctgttcct cgtggtaaaa    99180
gatatggtaa atgggcaaaa ctggttgaag attctactga agtattgatt attaagttac    99240
ttgctaaacg gtatcaagtt aatacaaatg atgcaattaa ctataaatca attcttgcta    99300
aaaatggaaa acttcccttta gtattaaaag aactaaaagg tttagtcacg gatgattttt    99360
taaaagaagt gactaagaat gtaaagaac agaaacaact caaaaaacta gcattggaat    99420
ggtaaaatga ttgaaattac tcttaaaaaa cctgaagatt ttctgaaagt aaaagaaact    99480
ttgactcgta tgggaattgc taataataaa gataaagttc tgtatcagtc ctgccacatt    99540
cttcagaaaa aaggactata ctatatcgtc cattttaaag aaatgcttcg tatgatggc    99600 cgtcaggttg aaatgacaga agaagatgaa gttcgccgtg attcgattgc gtggctgtta    99660
gaagattggg gactgattga aatcgttcct ggtcaaagaa cttttatgaa agatttaacc    99720
aataacttcc gagttatttc ttttaaacaa aaacatgaat ggaaactcgt tccaaaatat    99780
acgattggta attaagcaag gggcttcggc cccttatttg gagtataata tatcaagagc    99840
ctaataactc gggctataaa ctaaggaata tctatgaaag aattttatat ctctatcgaa    99900
acagtcggaa ataatattgt tgagcgttat attgatgaaa atggaaagga acgtactcgt    99960
gaagtagaat atcttccgac tatgtttagg cattgtaagg aagagtcaaa gtacaaagac   100020
atttatggta aaaattgcgc tcctcaaaaa tttccatcaa tgaaagatgc acgagactgg   100080
atgaaacgaa tggaagacat tggtctcgaa gctctcggta tgaacgatt taaactcgct   100140 tatatcagtg atacatatgg ttcagaaatt gtttatgacc gaaaatttgt tcgtgtagct   100200
aactgtgaca ttgaggttac tggtgataaa tttcctgacc caatgaaagc agaatatgaa   100260
attgatgcta tcactcatta tgattcaatt gacgatcgtt tttacgtctt tgatttgttg   100320
aattcaatgt acggttcagt atcaaaatgg gatgcaaagt tagctgctaa gcttgactgt   100380
gaaggtggtg atgaagttcc tcaagaaatt cttgaccgag taatttatat gccatttgat   100440
aatgagcgta tatgctcat ggaatatatt aatctctggg aacagaaacg acctgctatt   100500
tttaccggtt ggaatattga gggatttgac gttccgtata tcatgaatcg tgttaaaatg   100560
gttctcggtg aacgtagtat gaaacgcttc tctccaatcg gtcgagtaaa atctaaacta   100620
attcaaaata tgtacggtag caaagaaatt tattctattg atggcgtatc tattcttgat   100680
tatttagatt tgtataagaa attcgcattt actaatttgc cgtcattttc tttggaatca   100740
gttgctcaac atgaaaccaa aaaaggtaaa ttaccatatg atggtcctat taataaactt   100800
cgtgagacta atcatcaacg atacattagt tataacatca ttgacgtaga atcagttcaa   100860
gcaattgata aaattcgtgg gtttatcgat ctagttttaa gtatgtccta ttacgctaaa   100920 atgcctttt ctggtgtaat gagtcctatt aaaacttggg atgctattat ttttaactca   100980
```

```
ctgaaaggtg aacataaggt tattcctcaa caaggttcgc acgttaaaca gagttttcca    101040
ggtgcatttg tatttgaacc taaaccaatt gcccgtcgat acattatgag ttttgacttg    101100
acgtctctgt atcctagcat tattcgtcag gttaacatta gtcctgagac tattcgtgga    101160
cagtttaaag ttcatccaat tcatgaatat atcgcaggaa cagctcctaa gccaagtgat    101220
gaatattctt gttctccgaa tggatggatg tatgataagc atcaagaagg tatcattcca    101280
aaggaaatcg ctaaagtatt tttccagcgt aaagattgga aaagaaaat gttcgccgaa    101340 gaaatgaatg ccgaagctat taaaaagatt attatgaaag gtgcagggtc ttgttcaact    101400
aaaccagaag ttaacgata tgttaagttt aatgatgatt tcttaaacga attatcgaat    101460
tacaccgaat ctgttcttaa tagtctgatc gaagagtgcg aaaaagcagc tacacttgct    101520
aatacaaatc agctgaaccg taaaattctt attaacagtc tttatggtgc tcttggtaac    101580
attcatttcc gttactatga tttgcgaaat gctactgcta tcacaatttt tggtcaagtt    101640
ggtattcagt ggattgctcg taaaattaat gagtatctaa ataaagtatg tggaactgat    101700
ggtgaagatt tcatcgcagc aggtgatact gattcggtat atgtctgtgt agataaagtt    101760
attgaaaaag taggtcttga ccgctttaaa gaacaaaatg atttagttga attcatgaat    101820
cagttcggta agaaaaagat ggaacctatg attgatgttg catatcgtga gttatgtgat    101880
tatatgaata accgcgagca tctgatgcat atggaccgtg aagctatttc ttgtcctccg    101940
cttggttcaa agggcgttgg tggattttgg aaagcgaaaa aacgttatgc tctgaacgtt    102000
tatgatatgg aagataagcg atttgctgaa ccacatctaa aaatcatggg tatggaaact    102060
cagcagagtt caacaccaaa agcagtgcaa gaagctctcg aagaaagtat tcgtcgtatt    102120
cttcaggaag gtgaagagtc tgtccaagaa tactataaga actttgagaa agaatatcgt    102180
caacttgact ataaagttat tgctgaagta aaaaccgcga atgatatagc gaaatatgat    102240
gataaaggtt ggccaggatt taaatgtccg ttccacattc gtggggtgct aacttatcgt    102300
cgagctgtta gtggtttagg tgtagctcca attttggatg gaaataaggt aatggttctt    102360
ccattacgtg aaggaaatcc atttggtgac aagtgcattg cttggccatc aggcacagaa    102420
cttccaaaag aaattcgttc tgatgtactg tcttggattg actactcaac tttgttccaa    102480
aaatcgtttg ttaaaccgct tgcgggtatg tgtgaatcgg caggtatgga ctatgaggaa    102540
aaagcttcgt tagacttcct gtttggctga tagaataaat ctagggacct ccgggtccct    102600
ttttcataca agtaatataa atctatactt aggaaaaata gatgattctg gacctctgga    102660
attcattaaa aaattttca caaaatggtt tacaagactg ttcctctgtg gtactataca    102720
actatcaacc aatacagatt tggagaatga atgaaaatc gctattttag ttattgcatt    102780
gggtcttact ggttgtgtag ctcaaggacc agtagtaaat cagtctgatg caggaaaaat    102840
tgtaaactgt tcaagcaaat tttataatcc taacgtcaag tgttataaag aagctccaaa    102900
acagacagta gaagaaatgc aggcgaattt tgacgaagct attcgtccag atgaatctgc    102960
tcaagcatat cgtaattcag atgtgattac gcgtgaagaa aaaattgaaa actactcgc    103020 tgaactttgg gctaattggg ctaataatta ccaatggcgt actggtaaaa atgctccgat    103080
ggagtatgta gtaaattctt acaattcatg cgtaaaaaat ttgactaagt gaggaaacat    103140
ggaaacttta gtagcaggtt caattttat ggttttagtt tcaggcgtgt tggctattat    103200
tatatacatg cttccgtggt tcatcgcctt gatgcgtggg tcaaaatcga cagtaggaat    103260
cttttttaca tctttactgt ttaactggtc aatcattggt tggttatta catttatttg    103320 gtcaattgcg ggtgaaacta aaaagtcaac acagccaaat caagtaatta tcatcagaga    103380
```

```
gaaggaatga aaagcaaaat tataacagtg ttgcttttaa tcttgatgat tataataagt    103440
atatactata gtgtaacggt tcctcttatg attccaacgc ttattatagg gtggagttta    103500
ttactgttac aagttaaata tgaatgtatc aattgaggtt taaatgatta atgactctat    103560
gacagttgaa gaaattcgtc ttcatttggg aattgcatta aaggaaaaag attttgtaat    103620
tgacaaaacc ggggttaaaa ctattgaaat tattggtgca tcatttgtag cagatgaacc    103680
tttttatttt ggtgctctta atgatgaata cattcagcgt gaacttgaat ggtataaatc    103740
taaaagtttg tttgttaaag atattccggg tgaaacgccg aagatttggc aacaggtagc    103800
atcttctaaa ggcgaaatta actcgaatta tggttgggcc atctggtcag aagataacta    103860
tgcccagtat gatatgtgtt tagctgaact tggtcaaaat cctgattctc gacgcggtat    103920
catgatttat actcgtccat ccatgcagtt tgactacaat aaagatggta tgtcagattt    103980
catgtgtacg aatacagtac agtacctgat tcgtgataag aaagtcaatg cagtagtaag    104040
catgcgttca aatgacgtag tcttcggatt ccgtaatgat tatgcatggc aaaaatacgt    104100
actagataaa ttagtatctg atttgaatgc aggtgattca actcgtcagt ataaagcagg    104160
ttccattata tggaatgtcg gaagccttca tgtgtattcc cgtcattttt atttagttga    104220
ccattggtgg aaaactggcg aaactcatat tgcgaaaaaa gattataacg gtgagtggaa    104280
atgattcaat tcgtaattcc aagctatcaa cgcgtagggg cagttctgc ccttgatatg    104340 tttccatctg attatgaacc gcatattgta gtacgtgaac atgaagaaaa agcttattat    104400
gacgcttacg ggtctagagc caaaattata actattcctg atgatgttaa tggaattgct    104460
ggcactcgta aagcaattac tgatatgtat gcaggtcaac gaatttggat gattgatgat    104520
gatactacta ttcgtatgag ttcaatgcga aaaagagatg accgtcgttg tgtagataaa    104580
gtcaatcaat taacccgtga acagttctat gaattgattc aatacgtcga agatgccatg    104640
gattgcgggt attatcatgg ccatgctcgt ctacctatt ttaaaattac ttcatcttgg    104700
ggtaattatc gtgaaaattc atatggattc acgaatacat ggtatgaccctt cggaaaactt    104760 acaacagaac aaattgggta tggaaaaatt gatttatgcg aagatatgta tgcattctc    104820 aatttaatta atcaaggtta tccgcatttg gccctgttca aatatctggt tgtatctgga    104880
aaagcgcaag ctccgggcgg gtgcagttca attcgtagta attcaaaaca taatagagct    104940
cttgagcaaa tcaatagaga gttttccagag caagctcgtt ggaaaacatc gaatattgaa    105000
aagagaaaat cgttgggtga agaagacgag ccattaaagg ttcttcgcat gtgtgtttcg    105060
cgcaaagaaa aatcagaagc gtttcataag tttaatgcta ttcatccaat agcagttgat    105120
taatgcctaa atttattgtg ttataattac tttatcttta accagtgagg aaaatataat    105180
gatgcctatg gaaaaaatga atgtctattg cagatttaaa atcccgtttg attaaagctt    105240
ccacttctaa aatgactgct gaactgacta catctaaatt ctttaatgaa aaggatgtaa    105300
tccgtacaaa aatcccaatg cttaatattg ctatttctgg tgcgattgat ggcggtatgc    105360
agtctggttt aactattttc gcagggcctt ctaaacactt taaatcaaat atgtctttga    105420
ctatggttgc agcgtatttg aacaaatatc ctgatgcagt ttgtctattc tatgatagcg    105480
aatttggtat tactccagct tatttgcgat ccatgggagt tgacccggaa cgagtaattc    105540
atacaccaat ccagtcagtt gaacagctga aaattgatat ggtgaatcag cttgaagcta    105600
ttgagcgtgg tgaaaaggtt attgtattca tcgactcaat tggtaatatg gcttctaaga    105660
aagaaacgga agatgccttg aatgaaaaat ctgtggcaga tatgactcgt gctaaatcac    105720
```

```
tgaagtcatt attccgtatt gttactcctt attttagcat taaaaatatt ccatgtgttg    105780
cggttaacca tacaattgaa accattgaaa tgtttagtaa aaccgtgatg acaggtggta    105840
caggcgtaat gtattcagct gatactgtat tcattatcgg taagcgtcag attaaagatg    105900
gttctgatct tcaggggtat caatttgttc taaatgtaga aaaatctcgt accgttaaag    105960
aaaaaagtaa attctttatt gatgttaaat ttgacggtgg tatcgatcct tattctggat    106020
tgttagatat ggctcttgaa ttaggatttg tagtaaaacc taaaaatggc tggtatgctc    106080
gtgaatttct tgatgaagaa accggcgaga tgattcgcga agaaaaatct tggcgtgcaa    106140
aagataccaa ttgcactaca ttctggggtc ctttatttaa gcatcaacca ttccgagatg    106200
ctattaaacg tgcttatcag ttaggtgcta ttgatagtaa tgaaattgtt gaagctgaag    106260
ttgatgaatt gattaactca aaggttgaaa aatttaaatc tccagaaagt aaaagtaaat    106320
cagcagctga tttagaaact gacctagatc agttaagtga tatggaagaa tttaatgaat    106380
aaagatgatt tagatttaga tctagaaatt atcgacgaat cccctcttc ggaggggaa     106440
gaagaaagaa aagaacgcct ttttaatgaa tctcttaaga taattaaatc tgccatggaa    106500
aatgttatcc aggagattgt cattaaacta gaagacggtt ctacacacat tgtgtatgtg    106560
acaaaattag attgggttga tggaaaagtc gtaatggact ttgctgttct tgaccaagaa    106620
agaaaagctg agttagctcc tcatgtagaa aatgtatta caatgcaact acaagatgca    106680
tttaataaaa ggtcaagaa aaatttaaa ttcttttaag gagtaagtgt ggtagaaatt     106740
attctttctc atctcatatt tgatcaagct tatttttcaa agtttggcc atatatggat     106800
tcagaatatt ttgaaagtgg tccagctaaa atacattca aattaattaa atctcatgtt     106860
aacgagtacc atagcgttcc atctattaat gcgttaaatg ttgcgctaga aaatagttca    106920
tttactgaaa cagaatattc tggtgtaaaa acacttattt caaaactggc cgattctccg    106980
gaagaccata gctggttagt aaaagaaaca gaaaaatatg ttcagcaaag ggcgatgttt    107040
aacgccacat ctaaaataat tgaaattcaa accaatgctg agcttcctcc agaaaaacga    107100
aataagaaaa tgccagatgt aggtgctatt cctgacatca tgcgccaagc attgtcaatt    107160
tcatttgata gctacgtcgg tcatgattgg atggatgact acgaagcacg ttggctatct    107220
tatatgaata agctcgtaa ggttccattt aaactcaaaa ttctaaataa aattactaaa     107280
ggcggagctg aaactggaac actgaacgtt ttaatggctg gtgttaacgt tggtaagtca    107340
ttaggattgt gttcattggc agcagattat ttgcagctcg acacaatgt tctttacatt     107400
tccatggaaa tggcagaaga agtctgtgct aagcgtattg acgctaatat gctcgatgtt    107460
tctcttgatg acattgatga cgggcatatt tcttacgctg agtataaagg aaaaatggaa    107520
aaatggcgtg agaaatctac tcttggccgt ttaattgtta aacagtatcc tactggtgga    107580
gcagacgcta atacatttcg atcgctttta aacgaattaa aactcaagaa gaattttgtt    107640
ccaacaatca ttattgtcga ctatctaggt atttgtaaat cttgccgcat cagggtttac    107700
tcagaaaata gttacacaac tgttaaagct attgcagagg aattgcgtgc tcttgctgtt    107760
gaaaccgaaa ctgttctttg gactgcagcg caggttggta agcaagcttg ggactcttcc    107820
gatgttaaca tgagcgatat tgcagaatct gccggtcttc cagcaacagc cgattttatg    107880
cttgcggtca ttgaaaccga ggagttagca gctgctgaac aacaactcat taagcaaatc    107940
aaatcacgat acggtgataa gaataaatgg aataagtttt tgatgggggt tcaaaaagga    108000
aatcagaaat gggtagaaat tgaacaagat tctactccaa ctgaagtgaa cgaagtagca    108060
ggttcacagc agattcaggc tgaacagaac cgctatcaaa gaaatgaatc ggctcgagct    108120
```

```
cagttagatg ctttggcaaa cgaattaaaa ttttagttta caagccgaca agactatggt   108180
atagtagtct tgttggttaa atgaggagat tgttatggaa ttggtaaagg tagtttttat   108240
ggggtggttt aagaatgaaa gcatgtttac taaagaaatc gcaatgatga aagatgacgt   108300
tcaatgggct actactcaat atgctgaagt taataaagca ttagttaaag ctttcattga   108360
tgacaagaaa gtatgtgaag ttgattgtcg aggataatat gcatattgtt ttatttaaac   108420
ctactccata tagtgttagg aaaaatactc aattcaaagc acttatcgca gatacgtggg   108480
aattggtatt agatattcca gcagaagaaa gccctccatt tggtcgagtg gaatttatta   108540
agtttgctgt gcgccctacg aagcgacaga ttcgccaatg caaaagatac tttcgtaaaa   108600
tcgtcaagtt agagaaacag tttgtaacgt gtgattatac agaagtttta aataactgt    108660 ttacttttat tggaaaatga gatattatat aaacataaac tactgaggag attattatga   108720
aaaaatttat ctttgctgca attttttgctt tatcttcttg cgctgctcag cctgctatgg   108780
cgggttatga caaagatttg tgtgaatggt ctatgactgc agatcagact gaagttgaaa   108840
ctcaaattga agcggatatt atgaatatcg ttgagcgtga tcgtcctgaa atgaaagctg   108900
aggtgcaaaa acagcttaag tctggtggtg taatgcagta taattatgtt ctgtattgcg   108960
ataaaaactt taataataaa aatatcatcg ctgaagtggt aggtgaataa ttagaggtta   109020
atatgtatag ttctgaattt ccatatttaa aaatggaaaa aatttcatac gattttatag   109080
atgaaaaggt ttattacagt tttcatgagc cgcgttttaa cagtgaagtc ggtttttattg   109140 tagtaaaaga taatttcatt ttaaaaatat attcggcatt aaaggatttt cactacgaaa   109200
atattaacct aaaatttgat aaagaaaacg ttcgtaattg cgcagtaaca attacaggaa   109260
ataaaggtac atgtgttatg ctatctgatg aaattaatga tttgctaaat aatgcagaaa   109320
agattaccat tccatctatt gatgaccaaa tttttaatgc ttttatgaat agaggttaat   109380
atgaaaacat ataagaatt tattaaagaa gatatggtag ctggagattc aggtggtaat   109440
cctgaaaata tctctactgg aacaacgtca ggtgctgtag taaataaagg tcctgaacag   109500
attcctaaaa agaaaaaaga ggaatctaaa gaaaaagaag agtaaaaatg tcatcaatac   109560
cttggattga taatgagttt gcgtatcgtg cattagctca tttacctaaa ttcacacaag   109620
taaataatag ttcaactttt aaattgcggt ttagatgccc tgtttgtgga gattcaaaaa   109680
ccgaccagaa taaagctcgt ggatggtatt atggtgataa taatgaagga aatattcatt   109740
gttataactg taactatcat gcaccaatag gaatatattt aaaggagttt gaacctgatt   109800
tatatcgtga gtatatcttt gaaataagaa aagaaaagg taaagtcgt ccagtagaaa    109860 aacctaaaga acttcctaaa caacctgaga agaaaataat taaatctctt ccgtcatgtg   109920
ttagattaga taaactggcg gaagaccatc caattataaa atacgtaaaa gctcgttgta   109980
ttccaaagga taaatggaaa tatctttggt ttacaactga atggcctaaa ttagttaata   110040
gtatagcacc aggaacatat aaaaaggaaa tacctgagcc tcgtcttgtt attccaattt   110100
ataatgctaa tggaaaagct gagtcttttc aaggacgcgc attaaagaaa gatgctcctc   110160
aaaaatatat caccatcaaa gcttatcctg aggcaacaaa aatctatgga gtcgaacggg   110220
ttaaagatgg tgatgtatat gttctagaag gacctataga ttcgctttt attgaaaatg    110280 gtatagctat tacgggcggt caattagacc tagaaattgt tccatttaaa gatagacgtg   110340
tatgggtttt ggataatgaa cctcgtcatc ctgacactat taaacgaatg actaaattgg   110400
ttgatgcagg agaaagggtt atgttttggg acaaatctcc ctggaaatca aagatgtta    110460
```

```
atgatatgat tagaaaggaa ggtgcaaccc ctgaacaaat tatggaatat atgaaaaata   110520
atattgccca ggggttgatg gctaaaatgc ggttatctaa atatgctaag atttaaatta   110580
acccaactaa agcaaatgct aaatctacga atgtatcaag agtaactact ggaatattaa   110640
taccatgtgc aattgcaatg ggtgataaaa taaagttcca gagtaaaatt cctaccatag   110700
cagaaatagt aaaagctata cgttttttat tacctttat ggcatcaaca agtgccatta   110760 attttttgtgc catgtgtcct cctttaaatt aatatttatc ataaatttgt ttactttctc   110820
agcttgttat gatattataa ataaaattgc tgaggatgat atgatgatta ataaaattgt   110880
gcatgaaatg gctttaaatg gagattcata taaaatatct gccgtagttg aaaatttcat   110940
acttaataaa gtaaaagaat atttcactga ttgttcagtt agttatcaag aaaaaatggt   111000
tttaaccgat gatactgaaa aatcaaataa tttgttttgt tctaattta taactaagaa   111060 gcgtactaga agatttgata ttgttatttc tcgcaacggt aaaaagcata taattgaaat   111120
taaacatcaa gttggtggag gtacagctat tgattcggtt ggaatatatt tagaagataa   111180
agagaaatta aaagaataca caaaaactga aaaccctgtg tcattgatga tattagattt   111240
tttgccatgc ggatattatc cacgtaataa atggacaaaa agagaatcat ttactgataa   111300
tccaactatt caggcgaggt ttaatgaata tgctaaatca caaaacgtgt tagtattact   111360
atcaaataca tatgatgaag aattgtataa ttcattttt gctgcaataa atgagagaat   111420
ataatgctag gagctatcgc gtatacaggt aataaacaat cattattacc tgaacttaag   111480
cctcactttc caaaatatga cagattcgtg gatttatttt gtggaggttt atcagtgtct   111540
ttgaacgtca atggtcctgt attggccaat gatattcaag aaccaattat tgaaatgtat   111600
aagcgtctta ttaatgtatc atgggatgac gttttaaaag taataaagca atataaacta   111660
tcaaaaacat caaagaaga gttttgaaa ttacgtgaag attataataa aactagagat   111720
cctcttttac tttatgttct tcatttca ggatttagta atatgattcg tataaacgat   111780
aaaggaaatt ttactactcc gtttggaaaa agaactataa acaaaaatag tgaaaaacgc   111840
tttaatcact ttaaacaaaa ttgtgataaa ataatctta gttcattgca tttttaaagat   111900 gtcaaaattc tagacggcga ttttgtatat gtggaccctc catatcttat aacagttgct   111960
gattataata aattttggtc agaagaagaa gaaaaagacc ttttaaatct ttagattct   112020 ttaaatgaca gaggaataaaa atttggactg tcgaatgttt tagagcatca cggaaaggaa   112080
aacactcttc ttaaagaatg gtctaaaaaa tataatgtta agcatcttaa taaaaaatac   112140
gtctttaaca tatatcattc caagaaaaag aatggaactg atgaagtata tattttaat   112200 taattgctta cataatcaaa tgatataatt atttaactta ttaatgaatt gaaaggaaaa   112260
ataatggctt actttaacga atgtagtcaa ctgatcgaag gcgctgataa agctcaaaat   112320
gaatactggg atattctcgg tgatgaaaaa gacccgctgc aggttatgct tgatatgcag   112380
aaatctttgc aggttcgttt agcaaatgac cgcgaatact gctaccatcc agataaatta   112440
gaaactgccg gtgatgttgt ttcttggatg cgtgaacaaa aagactgtat tgatgatgaa   112500
ttccgcgaac ttctgacttc tcttggtgaa atgtcacgtg gtgaaaaaga tgcatctgca   112560
gtttggaaaa aatggaaagc acgttatatt gaagcgcaag aaaaacgcat tgatgaaatg   112620
tccccagaag atcagcttga aattaaattt gagcttgtgg atatatttca tttcgtatta   112680
aatatgtttg ctggccttgg aatgaatgcg gaagaaatct ttaaactta ttatttgaaa   112740 aataaacata attttgaacg tcaagataat gggtattaaa caaaattttt atagaacata   112800
tatagtaaaa gttaggacgc cgaaaggcgt cttttggtac gctgggaaac atgaatcatt   112860
```

```
tattgtaaat ccatatgatg ataaatatcc gggttcaggc aaaatattat ggaacatata   112920
tcgtaagtat ggttttaatt ataaaatacg ttggtcaaaa tgccatggtt ctagagaaaa   112980
atcatatgaa gttgaacgcg agctaatatc tgcattaaaa cgtaaacacc cagatacttg   113040
cattaatatt tctcctggtg gtcagggtgg agaaggaaga aaatggactg agcaacaacg   113100
attagaacat aaacttagat taaacaaccc tgaaacaaaa actcggatga agaattcaca   113160
acgtatagcc caaaatagag cagaacgaaa agctcggcaa tctgaagtaa tgaaaaagtt   113220
ttattcgaat ggcggaaata aaagatttc agaaggaact tcaagggcgc aagaaaagc    113280 accgcattgg catgaaccgc ttaaaagcga aatacacgag ttatgggttt ctttaggtaa   113340
accagcaaca ggcccggttg taaaggcgct taaaggaaaa tatgatgtaa caagttcagc   113400
tcttaagaat ttaatttact tattcagaaa agaaagatgta taaataatca tgtaatttaa   113460
ataaaaggag aattacatgg ctagtactcg cggttatgtt aatatcaaaa catttgagca   113520
gaaattagat ggaaataaga aaattgaagg aaaggaaatt tccgtagctt tccctcttta   113580
ttctgacgtt cacaaaattt ctggtgctca ttaccagaca ttcccttcag aaaaagcagc   113640
atattctaca gtatatgaag aaaatcaacg tactgaatgg attgctgcaa atgaagattt   113700
gtggaaagta actggtgaat aaattcaagg actccttcgg gagtcctttt tcattttacc   113760
ggtttacttt ccaaaatgag tatggtataa tagaattatc ttatagagga gagcgctatg   113820
ttaaatcgct ggattaaacc aaatgaagac ctccagaagg ttcttgataa agctatctct   113880
gataaatggg gcatgaaaag ctgggattgt gatatcgtca cgcattcatt catgatgcat   113940
gcagatggtt cagtcgagtt caatgctgaa atgcgataca ctgactgggg tggatttcaa   114000
agaatcgaat ttcaaagagg cttttttgtaa tgtttatctt taattggttt aaaagtttct   114060
ttacggattt tttctctacg actcctgggg aaggtgtagt tcctatttca aatgactacc   114120
ttcctttaac tgtagttgag tatgtttata tgggagatgg aacagtagaa gcagttacta   114180
tgacttatga agaagcccaa gaatattata aaaatccttg gcgctggtca gtacctacgt   114240
ctgcaccatc taatacacag tctagttctg attcatatga tactaatgtt cctgttcatg   114300
tatgggcggg cgattcatgt ggaagttctt gtgattctag ttgttcatct acatcttgtg   114360
attgaggaaa attatggaag cgattttgtt tgaaatgtat attagcagta atagcatgtc   114420
gtttgctaaa gatgttccaa ttaccgtagc agtaatgatt gataagggtt attgtgaccc   114480
aatgtatctc gtagaaaatt tcgtttcaat gccagttcca aagatgctg aaataaaact    114540 taaaagatt agtattattg aaactgtgcc aaatattccg tttagagcaa ttgaagcatt   114600
tactaaatcc gaatacatta atgttagcgc agaacaatat aatgataaac ctttatcatt   114660
ttattcatac gattcagtat atagttggaa aatagataaa ggaaataaat ttataattgc   114720
gagtgaagac gctttatcat attttatttc ttctgtatgg aatagtttac atccaaattt   114780
gctaaaaatt catgaatttg acgatgctcc tactgtcgtt ttaggtaaaa caatgaaag    114840 ttctgaagaa aatacttgaa tggtttagta gaccaaactc aatgtacatt gatgatggtt   114900
gggttgaaca agcaaataaa gaatgcagaa acgaatcgga agaatggatg aaatcaatga   114960
ttagtgctga gaaagaaaag aaattagaac gctcagcgct taaattgatg agagacatct   115020
atggtgataa atcatgaaca aagatatgac attggaagag gctaaagcaa aagcaaatga   115080
agcactggat ttgcttctta aaattggcag taaaatgatg gaagaaaatg agaaatatat   115140
ccaggaaaac aaaattcccg atggtccatt agtaggcaaa aggaaatcac atgattgaag   115200
```

```
tagcaaaaca ttattcaata gaatttatgt ctaaagaagg taaatcagta aatacacttg  115260
ataaaaaatg ctcattaatt attcctttag cagaaaatcc ggatttttta attgaagata  115320
taaaagaaag aaaatatcca gaaaatgtta ttctaattat aaaacatact gaagatattt  115380
tgcaggatac tgattcaccg ttttcttctt ctgaagcttt aattattaaa ggctataaaa  115440
gagttcatga atatggtctt tttgacctgt ttgaagacga taaagttaaa ttagcgagtc  115500
aaccttcaaa aagtaaaaca ttcattattg aagatattaa agatataaat gcatttgtta  115560
agatggtctg ggctcatttt gacgttggac tacgctggag aatgtccgaa gaagaaagaa  115620
agattattga agctaatcgt caatttggtt tttatcgcta ggaattaata tggatttatt  115680
tgagatgtta gaagataatc attctacgaa tatccagaat gattctagtg attataagaa  115740
agagtaccgt atagtattac agaattatgg aattgaagcc ccagatgctc ttctagaaga  115800
actagcttca taccatcttg accctccgcc ctgggctccc tgggcaaaat aattcaaaaa  115860
gttgtttact ttccttttcta acgatgatat gatagcttct gaagtatacg gaggctatca  115920
tgattattaa tcttgcagat gttgaacagt tatctataaa agctgaaagc gttgattttc  115980
aatatgatat gtataaaaag gtctgtgaaa aatttactga ctttgagcag tcaattcttt  116040
ggcaatgtat ggaagctaaa aagaatgaag ctcttcatca gcagttgaat aaaatcgtta  116100
aaaagcattt aactaaatca ccttatcagt tatatcgtgg tatatcaaaa tcgacaaaag  116160
aacttattaa agatttacaa gttggagaag tgttttcaac gaacagagta gattcattta  116220
ctactagttt gcacacagca tgtggttttt cttatgctga atatttcact gaaacaatac  116280
ttcgtttaaa aactgataaa gcttttaatt attctgacca tatcagcgat attatacttt  116340
cttctcctaa tactgagttt aagtacacgt atgaagatac tgatgggcta gattcagagc  116400
gtactgataa cttaatgatg attgtacgtg aacaagaatg gatgattcca attggaaagt  116460
atagaataac ttctatttca aaagaaaaat tacacgattc atttggaaca tttaaagttt  116520
atgatattga ggtagttgaa tgaaatactc agtaatgcaa ctaaaagatt ttaaaataaa  116580
atcaatggat gcatcggtgc gtgcttctat tcgtgaagaa ttactttctg aagggtttaa  116640
tttatctgaa attgaacttt taattcattg tattactaat aaaccagacg atcattcttg  116700
gttaaatgaa ataatcaaat ctcgtttggt tccaaacgat aaacctcttt ggagaggtgt  116760
tccagctgag actaagcaag tattaaatca aggaattgat attattacat ttgataaagt  116820
cgtatcagct tcatatgata aaaatatagc tctacatttt gcttctgggt tagagtataa  116880
cacacaagtt atttttgaat tcaaagctcc tatggtattc aatttccagg agtatgctat  116940
aaaagctcta cgctgtaaag aatacaatcc aaactttaag tttccggata gccatcgtta  117000
tcgtaatatg gaattagttt cagatgaaca agaagtaatg ataccggctg gaagtgtatt  117060
tagaattgca gatagatatg agtataaaaa gtgttcaaca tacactatct atactcttga  117120
ttttgaagga tttaatctat aatggaagga cttagattca ttataccatg aaagttttaa  117180 agcattttc ataaagttgt ttacaagtta agtaaaaat gttatagtat aagtagttaa  117240
ccgtccgtaa gatgtgagaa aaatatgaag ctgtctaata accaaattcg taaaattaaa  117300
cgtcgtctag agcatactca ggcatctgca aaaagacgtt ctaaagattt taacttagac  117360
ttcaattaca ttaagaacat tttagatcag aaagtttgtg cttactcagg agaacctttt  117420
gataatcgta ttgaaggaga gaaattatca ttagaacgtt ttgataataa cgttggatac  117480
attaaaggga atgttattgc agtaaagaaa agtataata catttcgttc tgattatact  117540
ttagaagagt tgattgaaaa gcgtgattta tttgctttgc gaattggtcg ttcatctgcg  117600
```

```
aaaaaagttc ataaactaaa tttagatgaa agaaatgggg ctaaaatcaa aaagacttat 117660
aatcaaatta aagctataca gaaaaaacgt gaaaaccgaa ttgaacacat ttctcagctt 117720
tctaaatcaa aacagacctc tgacattaag ctaagaatta tagcactcaa agctcgtatt 117780
gatggttctc gtatagcaga aggcgctgaa gttgttaaat tgaacgttct tcttaaaggc 117840
tcggattgga aaaccgtgaa aaagttgtca gaagcagaaa tgcaatatga tatgtgtgat 117900
aaaattattc aaggtgtaga gcggtatcaa aacttgtctt ttattgataa acttaaactg 117960
aaaagaggat acccgctaaa ttgttcaatt tttaaactta tccgaggata atatgtttta 118020
tgtatatgcg atagtgtata gagataaaga tggatttgtg gtgcctgttc ctcttgatga 118080
acatcgtcct gctgtatttt ttgaaaggga gattgctgat aaagtattta ctactcttaa 118140
agagcagtat caactagctt taggtatggg aattccgaga ttagttgaga ctccacgcaa 118200
gttttggttt aataaaatag aagttaaaca cgttaagcct gatgtagaca cgcaaagatt 118260
atatcggcga attttagata ctgggcgtat tgttagtata ccaattgcag ggaatttacg 118320
atgacatttg atgatttgac tgaaggccag aaaaatgcct ttaacactgt tatgagggct 118380
attaaagaaa agaaacatca tgtaactatt aatggacctg ccggtactgg taagactact 118440
cttactaagt tcatcattga agctttaata tctacgggcg aaactggcat tatttttagca 118500 gctcctactc atgcggctaa aaagattctt tcaaaactgt caggaaaaga agcgagtact 118560
attcacagta ttctcaaaat taaccccagta acatatgaag aaaacgttct ttttgagcaa 118620
aaagaagtac cggatttggc taaatgcaga gtattaatct gcgacgaagt gtcaatgtat 118680
gatagaaagc tatttaaaat tctgctttca actatcccgc cgtggtgtac tataattgga 118740
ataggtgata ataagcagat tagacctgtt gacccaggag aaaacactgc ttatatcagt 118800
ccattcttta cacacaaaga tttttatcag tgtgaactca ctgaagttaa acgcagtaat 118860
gctcctatta ttgatgtagc tactgacgtt cgtaacggta agtggattta tgataaaatt 118920
gttgacgggc atggagtacg tggatttact ggtgataccg ctttacgcga ttttatggta 118980
aattattttt caatcgtcaa atctctagat gatttgtttg aaaatcgcgt aatggcattt 119040
acgaataaat ctgttgacaa gttaaatagc attattcgta aaaagatttt tgaaactgat 119100
aaagatttta ttgtcggtga aattattgta atgcaggaac cattaattaa aacatataaa 119160
attgatggaa agcttgtgtc agaaattatt tttaataacg gacaattagt tcgtattata 119220
gaagcagagt atacatcaac ctttgttaaa gctcgtggtg ttcctggaga atatctaatt 119280
cgtcattggg atttaacagt agaaacttac ggcgatgatg aatattatcg tgaaaagatt 119340
aaaataattt catctgatga agagctgtat aagtttaact tattttttagg taaaacggca 119400 gaaacttata aaaattggaa taaggcggaa aaagctccgt ggagtgattt tgggatgct 119460 aaatcacagt ttagtaaagt gaaagcactt cctgcatcaa catttcataa agctcagggc 119520
atgtctgtag accgtgcttt tatctatacg ccttgtattc attatgcaga tgctgaacta 119580
gctcagcagc ttctttatgt tggtgtaaca cgtggtcgtt atgatgtgtt ttacgtatga 119640
ttaaattcga ggaagctatt cgtggaaata actaaagatc agtttttatct gctccaagat 119700 aaagtaagcg aaatttatga aatagcttat agtaaaaatc gcaaaacgt gaaaattgaa 119760 tcaggcaagt taatgcttca attggaagaa attgaacgag atttgattgc gttagaattc 119820
ttttgcggtg aagtgaaaac tgttacaatc agtgattaca ttttaggtga aattagccat 119880
ctttataagg cggttattaa tgattgaatt aagttggtgt cagtttaaat ttcttatgac 119940
```

-continued

```
aaatgttaaa gctgtcattg agaaaaattc tggtcctgaa atattacta ttcgcgaaaa    120000
agctttaaag ataatataca gtcttgaaga gatgcaaaaa gatattgaat ctatggcaaa    120060
atttattgat gaacctatta ataaagttta tattcaagac tatactgtag gtcaaattcg    120120
cgatttagca aggaaaattt aatgtttgat tttattatag attttgaaac aatgggaagt    120180
ggtgaaaaag cagcggttat tgatttagct gtaattgctt ttgaccctaa tccagaagtt    120240
gttgaaacat tcgatgaact agtttcacgt ggcattaaaa tcaaatttga tttaaaaagc    120300
caaaaggac atcgtctttt tactaaaagc actatcgaat ggtggaaaaa tcagtctcct    120360
gaagctcgaa aaaatattgc accatcagat gaagatgtaa gcactatcga tggtattgca    120420
aaatttaatg attacatcaa tgcgcataat atcgatcctt ggaaatctca aggctggtgc    120480
cgtggaatgt cgtttgattt tccaatttta gtcgatctca ttcgcgatat tcaacgcctt    120540
aatggtgtat ctgagaatga gcttgacaca tttaagttag aaccatgtaa attctggaat    120600
cagcgtgata ttcgtaccag aattgaagca cttctgcttg ttcgtgatat gaccacatgc    120660
cccccttccaa agggaacttt agatggattt gttgcgcata attctattca tgactgtgcg    120720
aaagacatcc tgatgatgaa gtatgctttg cgatacgcta tgggtcttga agatgctccg    120780
tcagaggaag aatgcgatcc tctgtctctt ccaacaaaac gataaaaagt tgtttacttc    120840
ctcggttagt tgtggtatta taacaccata gctactgagg ataataaaat gaaaatttat    120900
cgtgttgaat catcgtttag tattcttaat aatgaagatg ctataacaat acgtcgaaat    120960
cttttgcgttc aaataacgcc atacaggagt ataatagatt catggagcga agagtggcta    121020
ttacacgtag gttatgacag acctaatttt atgcatcata gcgataataa taaaagaatt    121080
ccttttaccac acgaagataa actattagtt aaaaacgcta atatagtaat taatactaag    121140
ttcaagaaag attatgttgg agtagaatat catattcctg gatggtttat agctctttat    121200
cattttgctt tcgctagcga atatgatatg atgagatggt tcacacgaga agagcgggaa    121260
gaattatctt ctaaaggatt ttatctcgct gtatacgaag ttcctgaaga tgaagttatc    121320
attggtgggc accaagtaat gttccgcaaa tcgcatgctg aactcgtaga ttttattgaa    121380
atgagataat tatgaaattt aattataatc ctgaatacac accgaatcct gtagataaac    121440
tgattgattt tgatgttgta agcacttatg tatgccctat taaaccactg gaaattaagg    121500
aacctactat gactaccgct attgaaatcg gcaaaaccta caaactggtt gaacctaaaa    121560
ttaaaactaa tgccttgatt tctggtcata aaactctgac tgatgttttt ggcgaaggcg    121620
aatttattgt tgaagaattt gccaaaagtg agtggtttga caaatcttac gtcatccacg    121680
gtcgccggtt agataataac aaaataaaga aaaacctggt ttatgaagat gagttcatcc    121740
tgttccaaga agttgaagaa caagaccccta cagacctgtt gtgtgctgct gtgtctatcc    121800
gtcgtccttt tgataatcct atctgtggtt gggtaacaga ccagtggatt gaagatggtg    121860
ttgagcttct gaacgttgtc catgcaggag atttttagtgt agtacctcgt agtgcggtgg    121920
tagctatttt gaattaatag tttacaaact cttgggacca gagtataatg gtcctgtgga    121980
gtataaaatc tttttaacaa gtgagagata actatgatta ttaatattgg tgaaattgct    122040
cgtgtatctg ataaatcccg ttctaaagca gcaggaaaat tggtcgaaat tgtaagcatt    122100
cagcttaaac acggcgttaa agatgaagat tctgaagtaa aagtgcgtat cattcctaaa    122160
gatggaaagt ctaaacctca gtttggctat gttcgtgcga aatttcttga atctgcgttt    122220
ttgaaagctg ttcctgctaa aggaattgaa acgattgata cttcgcatgt aggtgtgagac    122280
tttaagtgga aactcggtca ggctattaag ttcgttgctc cttatgaatt cgaatttact    122340
```

```
gaagatgagg aaggggttgt tcaaaaacac catactcgcg ctatgtgtgc atacattact    122400
gatcaatggg tagaagatgg tgttaagctg tacaatgcgg tattttagg aacatacaaa    122460 gtcattcctg aaagttggat taaacactat agcaaagctc gctgtgcata aagtttaaaa    122520 tttttcata aaactatata catcagtagt tgattgtggt actatatcaa tatcaactac    122580
tgatacagaa aacaacttga agaataaaat ggataattcg ttaaaggtgc gctgatactc    122640
ttctgaaacg catcgctcca atgttcaatt aatgaggaaa ttatgatgaa acgtaaaatt    122700
gttcagaatt gcactaatga tgaatttgaa gatgtattat tcgatccaga tttggtagta    122760
gttcaaaagg aacatactag caagtttact cacttgactt ctgtttatgt gtatgagaaa    122820
gtcggtgata aacaaccaat ttatggtgta tttcgtgaaa ttactgaaaa tggcacaact    122880
tattggaagg aaatttatta atggctatta aatttgaagt taataaatgg tatcaattca    122940
aaaataaaca agctcaagaa aatttatta aagaccatac tgataacgga atctatgcgc    123000
ggcgtttagg tatggaacct tttaaaattt tagatgttga ctattacggg cgtcctacta    123060
aaattgtgac atctactggc atagttggat attcatcacg aggtacagtc attgacgaaa    123120
actttatctg gctttctagc aacgaagccg agttctttaa tgaagtggaa aatccatatc    123180
aggctactga agagcaggaa gaccctgcac cagtaactga accatctgaa ttcccggtaa    123240
tgaaagttac tattgaaaat aatgaacaag catggtcctt gtatcagatg ttgaaagctc    123300
actttaagga ataattatgc cgctttatga ttataaatgc caatccgaag actgtgcaaa    123360
agaatacgaa aaaatcaaga aaatttctga aagagatact gatgtatgtc ctgattgtca    123420
tcggattgct attcggttag tttccgctcc taagcatgtg aacggtggat tttacgactt    123480
acttaaaggg taattatgaa atatgttaat cgttctatcg cggcattagt attagcagta    123540
tctttagtag gatgtactga tgctgataat gcaaccaaag ttttgtcttc aagcggtttt    123600
actaatattg aaatcactgg atataattgg ttcggttgct ctgaaaatga tttccagcat    123660
actggatttc gtgctattgg acctactggg cagaaagtag aaggaacagt atgttctgga    123720
ctattcttca aggattcgac tattcgtttt aaataaaagg ccttcgggcc tttagcttta    123780
tgattattgg agtataatat tcccgaaacc aaacgaggat aagtgatgat taagaatgaa    123840
attaaaattc tgagcgatat tgaacatatc aaaaagcgta gtggcatgta tattggctct    123900
tctgctaatg aaatgcatga gcgctttctg tttggtaaat gggaaagtgt tcagtatgta    123960
cctggtcttg ttaagcttat tgatgaaatt atcgataact cggtagatga aggtattcgt    124020
actaagttta aattcgcgaa taaaattaat gttactatca aaaacaatca agtaacagtt    124080
gaagataacg gtcgtggtat tccacaagcg atggttaaaa cacctactgg tgaagaaatt    124140
cctggtcctg ttgccgcctg gactattcca aaagcaggtg gtaacttcgg tgatgacaaa    124200
gaacgcgtca ctggtggtat gaacggtgtt ggttctagtt taactaacat ttttttctgtg    124260 atgtttgtcg gtgaaactgg cgacggtcaa aataatattg tagttcgttg ttcaaatggc    124320
atggaaaata atcatgggaa aactattcct ggaaaatgga aaggaactcg tgttactttc    124380
attcctgatt ttatgtcatt tgaaactagt gagctatctc aagtttatct tgacattacg    124440
ctagatcgtc tccagacact tgcagtagtt tatcctgata ttcaatttac ctttaatggt    124500
aaaaaggttc agggtaattt taagaaatac gcacgccaat atgatgagca tgctattgtt    124560
caagaacaag aaaattgttc tattgcggtt ggtcgttcac cggatggttt tcgtcaatta    124620
acgtacgtca ataacattca tactaagaat ggtggccatc acattgattg tgttatggat    124680
```

```
gatatttgtg aagaccttat tccacaaatc aaacgcaagt tcaaaattga tgtaactaaa   124740
gcacgtgtta aagaatgttt gactatcgtt atgtttgttc gtgatatgaa aaacatgcga   124800
tttgattctc aaactaaaga gcgtttgact tctccttttg gtgaaattcg tagtcatatt   124860
caacttgatg ctaaaaagat ttcacgtgct attttaagta atgaagcaat tttaatgcca   124920
attattgaag ctgccttggc tcgtaaattg gcggcagaaa aagcagcaga aactaaagca   124980
gctaaaaagg cttctaaagc taaggttcat aaacatatta aagcgaatct ttgcggtaaa   125040
gatgctgaca ctactctttt cttgactgag ggtgattctg ctatcggata tcttattgat   125100
gttcgtgata aagaacttca tggtggttat ccattgcgcg gtaaagttct taacagttgg   125160
ggcatgtcat atgctgatat gcttaaaaac aaagaactgt ttgatatttg cgcaatcact   125220
ggattagttc ttggtgaaaa ggctgaaaac ttgaattatc ataatattgc tattatgacc   125280
gatgctgatc acgatggtct aggaagcatt tatccttctc tgctcggatt ttttagtaat   125340
tggccagaac tgtttgaaca aggaagaatt cgcttcgtca aaactcctgt aatcatcgct   125400
caggtcggta aaaacaaga atggttttat acagtcgctg aatatgagag tgccaaagat   125460
gctctaccta acatagcat ccgttatatt aagggacttg gctctttgga aaaatctgaa   125520
tatcgtgaga tgattcaaaa cccagtatat gatgttgtta aacttcctga aactggaaa   125580 gagcttttg aaatgctcat gggagataat gctgaccttc gtaaagaatg gatgagccaa   125640
tagtttactt taccacaagg atgtggtata attaattggg caatgagga tattgaaatg   125700 aaatcatata aagtaaattt agaacttttt gataaagcag ttcatcgaga atatagaatc   125760
attcaacgct ttttcgatat gggagaagct gaagagttta aaaaccgctt taaggatatt   125820
agagataaaa ttcaatccga caccgcaact aaagatgaac tactagaagt tgctgaagtt   125880
attaaacgca atatgaatta atgaggaaat tatgattatc accactgaaa agaaacaat   125940 tcttggtaat ggttctaaat caaaagcatt tagcatcaca gcatctccta agtatttaa   126000 aattctgtca tctgacttgt atacaaacaa gattcgcgca gtagtccgtg aattgattac   126060
caacatgatt gatgcccatg ctctcaatgg aaatcctgaa aaatttatca ttcaagttcc   126120
aggacgatta gatccgcgat ttgttttgtcg agattttggt ccgggtatga gcgatttga   126180 tattcagggt gatgataatt ctcctgggtt gtataattca tactttagtt catctaaggc   126240
tgaatctaac gatttcattg gcggatttgg tttaggttct aaatctccgt ttagttatac   126300
tgatacattt agtattactt catatcataa aggcgaaatt cgtggttatg tagcttacat   126360
ggatggcgat ggtccacaaa ttaaacctac atttgtaaaa gaatgggtc cagatgataa   126420 aactggtatt gaaatcgtag ttccagttga agaaaaagac tttagaaact ttgcttatga   126480
agtttcttat atcatgcgac cattcaaaga tttagctatc attaatggtc ttgaccgcga   126540
aattgattat tttccggatt ttgatgacta ttacggcgta aatccagaaa gatactggcc   126600
agatcgtggt ggattgtatg ctatctatgg tggtattgtt tatcctatcg atggtgttat   126660
tagagaccgt aactggttaa gcatccgtaa tgaagtgaat tacattaagt ttccaatggg   126720
ttcacttgat attgctccat cacgcgaagc tctttcacta gatgatcgta ctcgtaaaaa   126780
tattattgag cgtgttaaag agcttagtga aaggcattc aatgaagatg taaaacgatt   126840
taaagaatct acatctcctc gtcatacata ccgtgaattg atgaagatgg atattctgc   126900 tcgagattat atgattagta attcagtcaa atttacgact aaaaatctgt catataagaa   126960
gatgcaaagc atgtttgaac cagatagtaa gctatgcaat gcaggagttg tgtatgaagt   127020
aaatcttgac cctcgactga aacgcattaa gcaaagtcat gaaacttcag ccgttgcatc   127080
```

```
aagttatcgt ctgttcggta ttaatacaac aaaaattaat atcgttattg ataatattaa   127140
aaatcgcgtt aatattgtcc gtggattagc gcatgcgtta gatgataaag aatttaataa   127200
cactttgaat attcatcata atgagcgtct tttgtttatt aatccggaag tagaatcgca   127260
gattgattta ctccctgata ttatggcaat gtttgaaagt gatgaagtta acattcatta   127320
tttgtcagaa attgaagctt tagttaaaag ttatattcca aaggcagtaa aaagtacagc   127380
tcctcgtcct aaagctgcta ctgcgtttaa gtttgaaatt aaagacgggc gctgggaaaa   127440
agaggaactg tttacactta cgtcagaagc agatgaaatt actggttatg tagcatacat   127500
gcatcgttct gatattttct ctatggatgg cactacatcg ctttgtcatc catctacgag   127560
tattttgact cgtatggcta atcttattgg cattaatgaa ttttatgtta ttcgtccgct   127620
tttacagaaa aaggtaaaag aacttggtca gtgccaatgt atttttgaaa ctctgcgtga   127680
tttatatgta gatgcttttg atgctgtaga ttatgataag tatgtaggtt attcaagttc   127740
agctaaacga tatattgata aaattatcaa gtatcctgag ttagatttta tgatgaagta   127800
cttcagcgta gatgaagttt ctgaagaata tacacgactc gctaatatgg ttagttcatt   127860
acagggtgta tatttcaacg gtggaaaaga taccatcggt catgacatct ggacagtaac   127920
taatcttttt gatgtattat caaataatgc ttcaaaaaat agtgataaaa tggttgctga   127980
gtttaccaag aaattccgta ttgtttccga cttcatcgga tatcgcaatt ctttaagtga   128040
tgatgaagtt tcccaaatcg ctaaaactat gaaggcccct gcggcctaat aaggaaaatt   128100
atgtacaata ttaaatgcct gaccaaaaac gaacaagctg aaattgtcaa actgtattca   128160
agtggtaatt acacccaaca ggaattggct gattggcaag gtgtatcggt ggacacaatc   128220
cgtcgtgttt tgaaaaatgc tgaagaagct gagcgctcca aagttaccat tagcggtgac   128280
attacagtta cagttaagag tgatgcagct attgctccag ttgctaaatc tgacattatt   128340
tggaatgcat ctaaaaaatt catttcaatt accgttgacg gcgtaactta taacgcaact   128400
cctaatactc attcaaactt ccaagaaatt cttaatctgc ttgttgcaga taaattggaa   128460
gaagctgcgc aaaaaattaa cgttcgtcgc gctgttgaaa aatatatttc tggcgatgtt   128520
cgaattgaag gtggaagctt gttctatcaa aacattgaat tacggtctgg tttagttgat   128580
cgtattctcg attcgatgga aaaaggtgaa aactttgaat tttattttcc gttcctggaa   128640
aatctgctgg aaaacccaag ccaaaaagca gtatctcgac tctttgattt cttggtagca   128700
aatgatattg aaattacaga agatggttac ttctatgctt ggaaagtagt tcgcagcaat   128760
tactttgatt gtcactcaaa tacctttgat aacagccctg gtaaagtagt taaaatgcca   128820
cgtactcgcg tgaatgacga tgatacgcaa acttgttctc gtggtctgca tgtgtgttct   128880 aaaatcttata ttcgtcactt tggcagttca accagccgag ttgtaaaagt taagtgcat   128940 cctcgcgatg tagtatcaat tccgattgat tataacgacg ctaaaatgcg tacctgccaa   129000
tacgaagtag ttgaagacgt tactgaacaa tttaaataag gcttcggcc cttaactaag   129060 gaaaattatg ttaggttatc aagcacgagt aaaagaagaa tacgatcaat taatgctcaa   129120
aattaatgca ctgagcaaat ttttagaaag tgaaagtttt caacggtta atgcagttga   129180 gcaagaactg ttgctttcgc agttcatctc aatgaaatct tacgcggatt gtttagaaa   129240 aagaattgca caatttaaat aaaataaggg gcttcggccc ttttgtttta aggaaaaatt   129300
atgatttatt gtatgaatat cggtgattcc gacataaaag agattaaact gcacggaaat   129360
catcacgcta atattgtgta ctgtaataaa tttgagtttg gtcacgaaaa acttgggtt   129420
```

```
ctttattgta atgatgttat aatcatggat aaaaaggaac tcgatgaact cgaccgtgag   129480
tctttagatg aaaatgatcg aatttattac ggcactctta aagtacataa cgcttatctt   129540
agtggtaaaa aggaaagtct aaatgcagaa aacgaatcca ggtttacaga gactatttca   129600
gattccgaca tttaccctat cgaacaatga tttgactagt gaaatgaagg tcaaaattgc   129660
tgatacagca agatactctt taaaacaaaa cccgaaccag gataaagcag aagtcattga   129720
aagatgtcgt atcgctgtgt atgcagagtt ttttgtagca gattggttga gcgggtatgt   129780
taacaaaggc caagaggatg ttaatgaccc gtatacatat gcatgggatg tattggcgca   129840
tccaagatat tgcgggcttc gtgtagaagt caaaacacac caaactgact cacgttggat   129900
ttctgtaaca acaggatgca gcggagagta tccatacggt tctggaataa atctagggcc   129960
cattctgaat catcaggtcg ctgactgtat aattatattc aacactaaag aaattcatcc   130020
aggtgtcatc cagtacactc cgaagttcat cggtgataga gaagaccttc gtaaggttgt   130080
aagaaaaagc aactacaacg gatggtatct ttccatttaa aaattttcac aaaacggttt   130140
acataccaca aggactgtgg tactatacaa ctatcaactg atacggattt ggagaacaaa   130200
atgtttacta cagctgaatt aaaacgagca aaagctaaga aagggcaagg aaaatataaa   130260
gctgaattag ttaaagaact tcagtttgct gaggctgaat tgaattcaat gattattcaa   130320
aatgctccag aaactgaaat tgctcttaag cgtattgcga ataagtgtct tcgtgatgca   130380
atcgtcgatc ttttagcgga ttattgagta aaatgaaatt taaattttat tacgctaaac   130440
ataaaataac tgatgagttt gtgtcagttg aatattctag cgatgatgaa ggtatgattt   130500
atactcgctt agggtatcg cactgggagt ctgatacgcc ttattttca actcccgaag   130560 aaattacacg tttagttaat ggtcatatga atgaccactg gaatgtaatt ctttcagata   130620
gtcttaaagc ggctattaat agtaatgaaa tgaaaatcgc tgagattgaa ctatgagttc   130680
attatggtgg tgtttcgttt ggttaattag tattccattg atttgtttag catttacttt   130740
tgtgatgagg ttattatgaa aattttgaat tctgtactta ttgcttgtgc gtggtgggtt   130800
gcacaagttt cagcggtagt agttggtatt cacatttatt acgaatattt ttaaaaagtt   130860
gtttacaaga ctgttcctct gtggtactat acaactatca actacggagg aacagaaaat   130920
gaaaaagatt gttaaagcta tatggaatgt agttataata ctagtagttt tgagtatatt   130980
cccaatcgtt ttaatgattg atgtattaaa cgcttacttt ggatttatgt gaggaaaata   131040
tgaagcgtaa acgcagtgct tttacattta ttgaatggtt tttcgataat atttttccag   131100
ctttattcat tttcatgctg attttttgcct taggttcagt tgtagttgga atctatttga   131160
tggcagttgt cggaatggat attcaccaaa atggcttaaa atctgtggtt gaaacaattt   131220
ggaatggtgt aaaataatga atttactaag catttggttt tatattctta tgttttacat   131280
tggtgcaaat ttcccatatt ggatgggatg gtcaacaact gcatttggat tttatactcc   131340
ttgaggtgaa ttatgaaaat ctttaaagat gtaaagttg gtgaaatttt ttgcttagat   131400
aatggtgatc agttaattcg tatttcgcct cttaaaagca ctagcgagaa aatgacagtt   131460
aacgctactt tagcaaataa cagcaatgaa cgtttctgta ttgaaaatga tactgaaact   131520
tatactgtag aagagttctg ggaattaagc gtcgactgcg acgattaatt tatcggccgt   131580
atgtattcat gcggccttgg agtagaaaat aatttagagg aaattaaaat gaaatatatg   131640
actgttactg atctgaataa tgcaggggca actgttattg gtacaatcaa gggcggtgaa   131700
tgggtttttg gaactccaca taagacatt ttgtctaacc ctggatttta ctttttagtt   131760
agcaaatttg gtggtccatt tgatagtccg tgtgtatctg cgcgattta tgtaggtaat   131820
```

```
cagcgctcta agcaagggtt cagtgcagtt ctaagtcata ttcgtcagcg tcggtctcag  131880
cttgcgcgta ctattgcaaa taacaatgtt ccatacacgg tattttattt gcctgcttct  131940
aagatgaaac ctctgacgac gggatttgga aaaggtcagt tagctttggc gtttacccgt  132000
aatcatcatt ctgagtatca aacacttgaa gaaatgaacc gtatgttggc tgataatttt  132060
aaatttgttt tgcaggcata ttaatgagca atttccataa cgaacatgtg atgcagttct  132120
atcgtaataa tcttaaaact aaaggcgtct tcggacgcca gtgaggaaaa tatgaatatt  132180
gcaaaattat taggagttat ttcatttatt tgttggatag tagcatgtgt tttaactatt  132240
tgtattgatg ccagcagcgt gttttcacaa gctttagctc agggtatgtg tgcatattta  132300
acatttgtgt tgttatctac taatgattaa gaaaatcttg ggctactcag tagcccttgc  132360
tgctttattg gtagcgctat attatggaat aatgttcggg ttaattcaag tcgtgctttt  132420
catttctgat gttattatgg cactacattc actagtatgg taaatttatg caactgaata  132480
atcgcgattt aaaaagtatc attgataatg aagcattggc ttatgctatg tacacggttg  132540
aaaatcgtgc tattccaaat atgattgatg gatttaagcc agttcaacga tttgttatcg  132600
ctcgagctct tgatttggca cggggaaata aagataagtt tcacaaactc gcttctattg  132660
caggtggtgt agctgacctt ggatatcatc atggcgaaaa ctccgcacaa gatgcggggg  132720
ctttgatggc taacacttgg aataataact ttcctttgtt agatggtcaa ggaaactttg  132780
gttctcgtac cgttcaaaaa gcagcagcaa gtcgttatat ttttgctcgt gtaagtaaaa  132840
atttctataa cgtatataaa gatactgaat atgctccggt acatcaagat aaagaacaca  132900
ttcctcctgc tttctatttg cctattattc ctactgttct tcttaatggt gtttccggta  132960
ttgcaactgg ttatgcaact tacattcttc ctcatagtgt ttcttctgtc aagaaagctg  133020
tactacaagc tcttcaagga aagaaagtaa ctaaaccgaa ggtagaattc ccagaatttc  133080
gtggtgaagt cgttgaaatt gatggccaat atgaaattcg tggaacgtac aagtttactt  133140
cacgaactca aatgaatatc actgagattc cgtataagta tgatcgtgaa acttacgtga  133200
gtaaaatctt agacccgctt gaagataaag gtttcattac atgggatgat gcttgcggtg  133260
agcatggttt tggcttttaaa attaaattcc gtaaagaata ctctttgagc gataacgaag  133320
aagaacgcca tgcaaaaatc atgaaagact tcgggttgat tgagcgtcgt tctcagaata  133380
ttacagtcat taatgagaaa ggaaagctgc aagtttacga taacgtagtt gatttaatta  133440
aagacttcgt tgaagttcgt aaaacttatg tccaaaaacg aattgataat aaaattaaag  133500
aaactgagtc agcttttcgt ttagcctttg ccaaggcaca tttcattaag aaagtaattt  133560
caggtaaaat tgttgtacag ggtaaaactc gtaaagaact gaccgaagaa ctttcgaaaa  133620
tcgacatgta ttcttcttat gttgataaac tagttggaat gaatattttt catatgactt  133680
ccgatgaagc aaagaaactt gctgaagaag ctaaagccaa aaaagaagaa acgaatatt  133740 ggaaaactac tgatgtagtt acagaataca ctaaagattt agaggaaatc aaatgagtcc  133800
attcattggt attacaagcg cggcattagt atctggtagc atttactgg cgggtttagg  133860 tgttgttcct gccatagcag gaggtcttct tgcgttcgga attcaacgtg ttatcatgac  133920
agttatcaca gtcatgcagt aattttaggg agagcctcgg ctctcccttt tttatttcaa  133980
aaattttttc acaaaacggt ttacaaccaa agcatactgt ggtactatac aactatcaac  134040
tactgataca gaattacgga gattagaaaa tgtctaaagt aacttacatc atcaaagctt  134100
ctaacgatgt tctgaatgaa aaaactgctg cgattttaat taccattgct aagaaagatt  134160
```

```
tcattacagc tgcagaagtt cgtgaggtgc atccagattt aggtaacgca gtagttaata    134220
gtaatattgg ggtattgatt aaaaaaggcc tggtggagaa atctggtgat ggattaatca    134280
ttactggtga agctcaggat attatttcaa atgcggcaac tttatatgca caggaaaatg    134340
ctcctgaact gctgaaaaaa cgagcaactc gtaaagctcg cgagattact tctgatatgg    134400
aagaagataa agacttcatg ttaaaacttt tagatgaaaa tggatttgtt cttaaaaagg    134460
ttgaaactta tcgtagtaac tatctcgcta ttttagaaaa acgcactcac ggaattcgca    134520
attttgaaat taacaacaat ggaaatatgc gaattttttgg atacaaaatg atggaacatc    134580
```

```
tcattacagc tgcagaagtt cgtgaggtgc atccagattt aggtaacgca gtagttaata    134220
gtaatattgg ggtattgatt aaaaaaggcc tggtggagaa atctggtgat ggattaatca    134280
ttactggtga agctcaggat attatttcaa atgcggcaac tttatatgca caggaaaatg    134340
ctcctgaact gctgaaaaaa cgagcaactc gtaaagctcg cgagattact tctgatatgg    134400
aagaagataa agacttcatg ttaaaacttt tagatgaaaa tggatttgtt cttaaaaagg    134460
ttgaaactta tcgtagtaac tatctcgcta ttttagaaaa acgcactcac ggaattcgca    134520
attttgaaat taacaacaat ggaaatatgc gaattttttgg atacaaaatg atggaacatc    134580
atattcagaa atttactgat atcggaatgt catgtaaaat cgctaaaaac ggtaatgtgt    134640
atcttgacat taaacgctcg gcagaaaaca ttgaagctgt aatcaccgta gcatctgaac    134700
tgtgaggaat aaataatgaa caagttagaa attgttaatg aacttcgtcg ttgtgcagaa    134760
cccactcaag agggggtggga catctggtac catggggctt atcttggaac tattgtaaag    134820
attaagactg gtaaatacat gattattcgt gaaagtaaag atgctccagt aggtattcgc    134880
aataatttta tggcagcgat aagttccttt acgatgcag cttacgaaat ttaccttgct     134940
gattataaag aatttcagga atctcaacca gttattcgct caattggcgt taacaaagct    135000
caacagaaaa ctttatggca gcgtattaaa ggatggttta atgaaaaact tttaaagaac    135060
gtttagctct gttagataaa gctttgtcac gtgagactcc agaaagtttg gctgctaaat    135120
tagcttctta cagtggtgaa tacacagaag aagatatttt aaaagaagtt cctgaaatct    135180
gttggcagac cgcatactgg gatgaaaatc aaaagtatca acgaagaatt gtttgcgcag    135240
ccaatcgttt taaattaaaa gatggacgaa ctcttgttat tccaggtgct cgtcattatt    135300
ctaaagatat ggccgaagtt ttagatgtag ttaaaccccca attagttact cagcaagttt    135360
gtgatgatga ccaagggttt attgaccaat atagtaatta ttggacacgt gaagaagcaa    135420
tgattattgc aacttatgct ggacaagtac gtattgaacg tggtggtagt gaaaaagaac    135480
tttactctga ggacctttac taatgaatat taaaaagttt caaattgatg gaattatgaa    135540
tcaaattcag gcgctggaat atgccaataa aatgatgtca actaaatggg gaatttatgc    135600
caatgaacca gcatttcagt tctgtaatat ggaattcact aaaaagctcg taggaaaaga    135660
ttatgtatgc ccatttagtt ctccaataaa tggaatgtta aaacctgctt tacgcgatct    135720
ttatattgcg atgaatgaag agatgataaa agagctaaaa cgtcaactga aggtgattca    135780
atttggccag ggaaattaat tcaaaatccg attattttaa ttctctcaat gataaagata    135840
aaaatctaat acggcatttt attgttgaga tgggatatac tgacacacgt gatttaagag    135900
aacatatatt tgaatgtggt gtagctaaaa agttttcatt cacatgcaaa tgcttaagag    135960
aggtaattca gcactatgaa caatttagtc gcaaaacata attttaataa agcttctgtc    136020
cataaagata aaagaaagc gtttaaagaa tctaatcgca aacagaaaca taaggggaag    136080
gtctatgatt attgattctc aatctgtggt tcaatataca atcaaaattg atattctaga    136140
aaagctatac aagtttctac caaatttata ccactcaatt gtcaatgaat tagttgaaga    136200
attacatctc gagaataatg atttcttggt tggaatttat aaagataact caaaggcggg    136260
atatttttac gtaattccag ctccaggaaa aagtattgat gatgtattaa aaactataat    136320
gttttatgtc catgattacg aaattgaaga ttatttcgaa tgagtcataa tcttgaaatg    136380
gtaatcgagc ataatgtagc tcaggaacgt aagtcgttca aggaattcgt agaaaaaatt    136440
tttgaagaaa ataacacaga ccagtttaca aatcaagcgt ctgatgatat tataataaag    136500
tcaactaatt gagtggtata gttaatgaat aaaaacattg atacagttcg tgaaattatt    136560
```

```
actgttgcgt ctattttgat taaattttcc agagaagata ttgttgagaa tcgtgctaat    136620
tttattgcat ttctgaatga gattggagta acgcatgaag gtagaaagtt aaatcagaat    136680
tcattccgta aaattgtttc tgaattaacc caagaagata agaaaaccct catcgacgaa    136740
ttcaacgagg gttttgaggg tgtatatcga tatctagaga tgtatacaaa caaataatta    136800
tttagcccct cctaatattc tggccgcctg agaacatatt gattcaaggc ggtcattact    136860
tatgtgatca tttctatacc agtacatagt tattgttcca gcatagatat tatccaaatt    136920
aaaatatgga caactataca tgtaatttat ttcgggagta ggcttttag ttggtaaaaa    136980 agcaaatttt gagttagaat aataatgacg tccattaaa tgaactgcat attcatccat    137040
agttttatca acaggatatc ctccaagtga ttttcgctt attgttgaag gtaattttcc    137100
ttcatatgct atgatatcaa caaaatagtt aagttttta gggcggaaag aatacaccgc    137160
actaaagtct gcctcagatg atatatgaac tatctggagt tgttccaggg cgacagattc    137220
aaagcgtgca tttctttcct tttcaataat ttcactgtat gtttcatact ttgattgctt    137280
atagtactca aagaaactat ctcccctata ccaaacaatc gccatcataa ataaaagaat    137340
tacgacagct actcgggaag caagaaccctt cccggtagcg ttatctttga acaagcgatc    137400
tagaacacca aacagaatac cagagggcga aaatgatatt ctaggtgctg ccatattacc    137460
tccaatttat caatatttat aactgagagg tattatcgtt taaatccagg agccgtagat    137520
cgtgcctgta gcgccccatg atggtgaaga accgaatact gccctgcctg gagcaccacc    137580
gccagatcta gataagtgat tacccatcc atctccgccc cgacctccag catcaccgcc    137640
attgcctccg ccgaattggg aagtgtaacc ggcaccgccc ggggcgtcat aactagcatt    137700
accaccaggc caattaacgc cgcctccgcc gatgccaaat ggtctaccac caccgccacc    137760
tgctgtagca tttggcgccc agctattctg taatgacact gcaccaccac caccgccgcc    137820
tgatgcaata acgccatagt tccaaatacg aagtcttccg ccaatatcat tttggattac    137880
atcgccgcca tttgtgcctg ggtttccgtt tacagtaccg ttaccacctc gtccccacat    137940
atgaactcca ccatgaatat tcaaagtaac atattcattt ggcgtatcgc catacataaa    138000
gaataatgga acatctttac tatatgatac caaatttccg gtgatattaa acactatagg    138060
tgcactacct gcctcaaaac atctatctcg gaaccattga ccattgaagt tatggtctgc    138120
tccaagcgtg tgaattactt caacagatcg acctatcata ttactcatcc aaaatggaac    138180
acccattctt aatcttacgg ctgctcctgc catccaaggg tctccagtct gtacccttgc    138240
agaccatcct acccacggtc cttcaactgc catataaccct ccaaggggcc gaagcccctc    138300
ttattatttt aacaatgatt taactaattt tttaagctct tcaatctctg acttaagtcc    138360
tgcaatttct gcagtatgct cattgattgc agctgtattt aaaccaatta caccgttata    138420
gttcaaacga agtaaagctt caccattagg gtcaccttca accaattcag gtaaaatagc    138480
ttgaacttct tgggcaatta aaccagcgtt aggttcccat ttctgattgc cttcttcatc    138540
taggcctcgc ttctgcatat aagtgtaacc gttaattta gaaagcttct cagaagcatt    138600
ttcaaattta acaaggtctt ttttaacgcg aatatcagaa cggacataaa catcacggac    138660
atatgtagaa tagttgtcat tcgcctgaac gagatgacca taagacataa tagctcttcc    138720
ttgctcagtc cacaaagcgc cagtggtatc ccaaagacct tcatggatat gataagagct    138780
agaccatgaa gcaatatgca tgccattggc aaccatattt attcggccgt caccacccca    138840
tactaagcca gtgtcattat caccaataac aacacatgcg cctgtccatg caggatcacc    138900
```

```
tccaccagct gatattctta ctccagcttt aaccatgtca ggaacgtaca tgtttccatt   138960
atggtggaat tcgaagatag cttgcggatc gctagcattt tcctggttac caacacgaat   139020
aatagcctga gcccattggt tagtgatacg gcgcatacca aaatctacgc ctgatacgta   139080
tccttcgtta gtaataccag attttccttt aataatagga taataggagt cattgctgac   139140
ggatccaaaa tctacaaata caggcgcttc taaacccat tggtcacccc aggcgccaga    139200
tttatgcgca acccattgtg cagcctttat ataaagtcgg tccctattaa aataaaaagt   139260
atccgaccct tgaggagcta aaccaacttc tccgctatta tgaatactaa cgcctgaatt   139320
agtttggaaa ctataaaacg ataaggtgtt ctcagtgccg ccattaccaa cataccagtt   139380
attaacgcct gctttttgtc ctttcacata acaagattcg gttgcagcac tgttaataac   139440
aatagcatcc gagtttgcat tcagagttaa acggcctgtc atcgtgtcgc cttctttagc   139500
cacacgggag gcaatggcat cgcgaatatt agttacgtcg cctgctgaag taaacgtttt   139560
ccagatatca gaccagatat taccattgcg agcaatagta gcttcaccac caccgacaga   139620
aacgttatct gggaagttaa cagtaccgtc ttgattaaaa cgagatgtat ggccttgtga   139680
accatcttct ttgatatggt gtaaaacaaa tgtacccgaa ttaatttcag tacctaaaga   139740
ccaaacagct ttactgttta aaaacttctg tttaacaata ggataatatt tacttactgc   139800
gtcatcatcg atttcctgga aaataggagc tgcttgaaca tattgaatat cataaccacc   139860
agcgcccgcg ccgtgaccag taaatttaat ataaccgtta gcagcaaacg tattgtaact   139920
tgattgtaaa tctggaatag taactttacc agtatctaaa gccatactaa acgggcgaag   139980
tggaccgata tcaccatgtt taccttcacc ataagcagtt ggaataatat gaagactacc   140040
ttctgaacgt ctaaaaatag ctccataatc tgcgttccaa atacgaagcg cattcacagc   140100
cccagatgaa atttcgcctg ttgtgtgaac tcctttattt ccagcagtaa caccggatga   140160
ttcaaatgaa ccattgacgt tcatttctac ttcgccggta gtaagtcttt gaatatagct   140220
catccaacta gttgcgtcag aaatttccat gacatttta cgggtgcctt cactaggatt    140280
agtaaaggta ttaccccata cagaaattgt catattatca actgaactgt taccagttgt   140340
gttacctcta aacatcagcg tagaagaatt attacgacca tcaatattaa ctgaaccacc   140400
aataacgtca atattaccag gagtaactag caaaccgcca tgagtattaa tgtttgtggt   140460
acccttaccg cggaaataat gatgataatt accaccttgg taatatccta aaagagtctg   140520
accatctcca aacgcattat tatcatggta agtaacaaca gtagcgagag catagttttc   140580
agtaggagga gtagttaaat cattgccatt tacagaataa cccataacca tttttctaag   140640
gcttacggtt gattcaggac tataaaggaa agttctcgta ccattgttta ctacatagaa   140700
ataaccatct tgataccatt ttaatccggt atcattatca cccaaagcaa tagaaccttt   140760
acctaaggct gaatacgtca taggccctgc tgattccata cctactgcaa tcgaatgccc   140820
agcttgaaaa ccacctgaat aagcaaaaga caacatgaaa tcagtagggg ttgaaccaga   140880
ataccaactg atgccgttat tttcacaaat ttcatggagc attgcggccg ctgggttggt   140940
acgtacaacg cgcaaatagt ttttatctgt gtcagaatta ttattggcca ttgaatagat   141000
atcataatcg ccgacaactt taccatttgt aataacttta ttagtataaa ttacgggagt   141060
tgatacagat ttccacccaa aaacttctgg tgaagaaaac aaaccatttc cattaaaagc   141120
gaaagtgctt tctgaactag ctttgtaatc ttgaactctg atgttaacta cttgtgtagt   141180
taaaccgtca ttagcaggag aaaaaataat accgcgttca cggtcggcgg aatcatgaaa   141240
acgaacatgt gctgtaccctg aacttttttgt aataagttct ccgccttcag tcataatctg   141300
```

```
cccggcggca ataatatcgc gagttactcg agcaatacca gttaaattaa aattaccagt   141360
ctgagtgaag gttccattta aagtataatc accagtttga ttataatttc ctatatgaat   141420
aacattcccg tcaatgctac cgcctttagc aaaacccaga tcaatgatat ttccttggtc   141480
atctttagta aaaagtacgc ggtcttttaa atttatagcc aattcacctt cggctaatac   141540
tgaagcggca ggacgtgctc ctgcagtttt gcttctttta aattgtattt gttttaaagt   141600
agccataagt cctcttaata atagccgaaa tcttgaacag aatccttaat aacaatttga   141660
tcaaatcgtg aacatgcga aggttgagat gcaggattct gtgaaaaaag gtttggcgca    141720
gttaaattac ctgtcatagt atctccagag cgtaatactc tagagtttgc gtttgctgta   141780
acaatattta ttgctccatc gacataatct ttgcgagtta agtgtgctgg gccggtcggt   141840
actgaagcat tagaaataac ttgttggcca gaaacaatat tgccaactgt ttcaacttta   141900
ccactcctgg cattaaacca gattgtgcgt ccctggatcc catcacttgt gcatgtgttc   141960
caaataccaa tgccgtacca tgaacgtaaa tccatgttag cttttttctct ggaagctcca   142020 tctccattgc cagaatataa cccattcagg tctgaaccgc cagaaaacgt tgcagaaatc   142080
ctaacgcctt ctttaaattc tacttctttt tggaaacctt gagactttgt gccaccatta   142140
gctttagaaa cgaaatcgtt atcagttgcc tgtggtttat tgtattctga atatattta    142200 aatgatttat agagtacatc gtcaccggct ggattcaatg gaaaatttcc ttgatgccaa   142260
atgacagagc ctccagttgt tgaacctact tttaaatcag ccattgtatg ccccttatt    142320 ttaatagtat ttataaagaa aaagggaacc cgaaggctcc ctcaatttat acttctctaa   142380
attcttgccc aaatacttta ccagctttag acgatgcttg cgtaggaagt accattatat   142440
ccggaggtga agcagattca cagatataat taactcgaat accattgacg ccaaattcag   142500
caggttttga aattccgcca tttcttgaca cttccgaaaa gcttaaattc ctcatgccac   142560
cttgaccagc ttgtgcagtc ctttgcgcgt atatcgtaaa tcctactgca ttttctggaa   142620
taactacata atcttccttt aattcccatg acccagcttg tccagtaaac tcagcatgtg   142680
ttgaagaaat atatccattc gattcatcat aaaaacggat agatatattt gtagttccaa   142740
gcgcaagtaa atcggcatca gcatatagct gtgctttaag ataaagaaca tcgccaggaa   142800
ttaaattata atcagagagt ttacttatcg cggatgaagt tggtaaacgt gcaatttcgt   142860
tattagttcc accaaccgct gacataaatt gctcaacgct ttcgtatgtt cttttaggaa   142920
atcctgtagc tccaacgtct tctaaactat caaatacaac atctaaaata gtttgatagt   142980
catctgtgct ttttctatta cttagtttaa catgctctaa tgcaatagct cttttagaag   143040
aagtgtaaaa agcagcatat gatacgtcga atcttgacaa tacagaatca gatggaaaag   143100
cagacgttcc tgcggttctt atccaagata ctacttcagg aggaaaatta acttttccgt   143160
tagttaatat agcaacaagt ctattattcg tcaaagaatt catgaaacta acaaaagcag   143220
ctgatgtagt atcatttgaa gtcgaaaaag catatgactt actatcaact aatgctcctg   143280
tagaagggtc aaaaactctt aaatgaagtc ctgcgctaaa tgtttgactt ccgacaggat   143340
tatcctgaaa tttaacgtat ggtccttctg cagtagaaag cgggcaagaa cccgctatac   143400
ttattttata tcttactgaa ttgctttccg ataaaaatgg cgtttggaca tatccttgtc   143460
caaactctgc cataaatttt tccataatac ctcttattca atccattcaa atttaacaga   143520
tttattcact gggtcaggaa taatgcgaac attaccaatt cgtaagaaat cacgaatagt   143580
aagattcccc attgtagcat tatcagatgg taaagcaccg atatcagatg gctgaggagg   143640
```

```
gttacccca  tcaaatacct  gaacaaaact  tgaccaagag  ttttttggttt  tctgccatgt  143700
acgcgtccag  cgagtggtgc  gcgcttctgg  ggtcgttgga  taagtaatcc  aatcttggta  143760
aagcgaatcg  agtgtgttac  caaactgagt  caatgtacca  ggagatttaa  cctcttcgcc  143820
acgttctaag  tatggaagtc  cagtcacttc  attagttttt  tcaaccattt  caaaataacc  143880
cgggaactgg  ttataagtgg  ctgaatcatt  aatatcgatt  gaccagaatc  ctacagtatc  143940
agatgttggc  gcacgggtat  ataaatcaga  ggttttagta  ccctgagaac  gaattctcga  144000
gttaacagtt  aaaccacctg  aacttatagt  agcacctttg  gcaatgatta  agctttcacc  144060
aatcgttact  tgaccagatt  gattattaat  tgataatgga  cgtaatccat  aaatccacc   144120
gctctgatca  ccggctgcag  tgagcataaa  ataggtgtca  ttaccagcgt  tacgaataaa  144180
gaatccataa  ttaccatttta  ttgctctgaa  agcattcgat  gatttactga  taaattcgcc  144240
attagcagta  actgaactac  cgaatgttgc  aacgccattc  gcattcaaag  aacctaaagc  144300
attcacattt  attggcatta  cagtaccatt  aatgctaaat  gctatattac  catctttatc  144360
gcgttgagaa  taaaagtgat  aagatgtttc  atcactaact  tcaaatacgg  tagaacgtgt  144420
tgtgtttgat  tccccactaa  attgattccc  ccacacgctg  actgtcatcg  tttgagccgg  144480
gttcgttcca  gtttgaggtc  cttttctcaaa  aatcagacga  gttgctgttc  catcagtatt  144540
agaaatggtt  agtgtactat  ttgctgaaac  tggtccaccg  aacgtagcag  tactagatga  144600
tacaagaggg  gcactcagat  tcgtttgttg  cgttaaggtt  agtgaaccat  taactgtctg  144660
tgcaatatcc  ctacgaatga  actgagatga  atctagacca  tctaataaat  tactatctgc  144720
agcttttgct  tttaacggca  aataatttgc  taatacgcgg  tttaattcat  atggcgatac  144780
tgcatagcta  tttttctcat  ataattctaa  tgactgtgtt  gaaccaacta  tatcattacc  144840
aacgaatgta  attgaaccag  atgaagtttt  aacaaaacct  cttaccaaag  tagtagctgc  144900
ccaagtaggt  tcactctgta  caacccattt  taaatttttt  ggagatacag  cagtatttgc  144960
tgacgttcca  gctacagttt  cagcctgagt  tgcaacttta  ataacgcctt  cttgcgattc  145020
ggtagattta  gtacctaaaa  gctttttagg  agttattaga  acattatcca  atgttcctgc  145080
agcagcttca  acttgtgtag  ctacacgaag  tgtaccacgt  tgtgtctcat  ttgcttcaag  145140
aatattaagg  gtataatggt  cccagagagt  tcctgattca  actaatccag  atagagcaac  145200
aacagaagta  cgatcagtac  tattaaatct  ggttttaatt  tttaatggtg  tagagatacg  145260
agtatcgtcg  acgcctgcgt  cgaattcaac  ttgcgtagca  atttcagcta  taccacttaa  145320
accttcagtt  gctttacgat  catttaaagt  tttaggagtg  actgcacgag  tataatcagt  145380
tcctgtatta  acttcacttt  gcgtagcaat  ttcaattaaa  ccaattcttc  catcagttga  145440
tgtcttttta  tgtaacgttt  ctggcgttac  aaccgcattt  gcccatcctt  cttgactctg  145500
tccagcaatt  acttcacttt  caactgctaa  aattactgca  ccttgttgtg  ttggagtagc  145560
tttatactga  tctaaagctt  taggcgaaac  aactaaatta  ttagtgtttt  tattgtaaac  145620
atttgtacca  tttaattcac  ggctagaagc  tggagtagct  cctgcggtag  atacaaaagt  145680
tacgatacca  gataatgatt  cagaaccttg  acgagcttga  agctttttag  gagtgatgat  145740
tgtagtatca  tcggttcctg  tattagtttc  ttgctgcgta  gcaatttctg  cgacacctct  145800
gcgagtttca  gtagcagttc  tttcattcag  cttttttagga  gtgatgataa  tatcatcagc  145860
aaaagagaat  gtagtgtcct  ggttcacttg  ggcagtagtt  gctattcttg  cgatacctct  145920
acgagtttct  gtagcagtac  ggttagctaa  tgttctggt   gtaattgcta  attctttctg  145980
tggagaattt  tctaaatcag  catttgcttg  agcttgtgta  gctaaagcaa  ttacgcctaa  146040
```

```
tcttgctcta gtagaatcat ttaaagaatc aactctttca actgttggaa cgttttgttg   146100
tacaacccag tattttccgt cagaatcttc gatataagca agttgtaaaa ctggaacata   146160
attagtttca ccgttaaaaa ctaattcttg aacagtcacc cattcagctt caggcggata   146220
ctctgaacgt tttgggaatt gcagcaattg aactgaagaa gcaattttat cttcaccggc   146280
ggctttgatt ttaactgttt gtccttttct catgtaattc atggaaattt taacagtatc   146340
accaacagaa atattagttg gaagctgaag ttcaattgtt tgagttgttc cgttattcgc   146400
accaaatacc ataacttctt catttggacg aatactagaa ttagttgtta taatacgtaa   146460
acgtgcttta ctatccccgt caaacaatct ccacaatttt tcattatcat catacatcaa   146520
gaaaccgtca atcgatgtac gtccttcaat agaatgagtt ccatcttctt gtattgaagt   146580
agtttcatcg tatgtagtaa caattgtatg ataaagtgga tttagtttat ctaaatcgac   146640
gaaattaata atatcgccat gattagcaaa tctcggaagt ttaatattaa tcggcgcagc   146700
ggaagtaaat ctacgcacga taaatcgtt agattgcgcc tgataaagac ttgccggtgt   146760
tacaattgca gcttctctgc tataatcagc aacgtacatt tgccacagac gattactaaa   146820
aattaaaact atctgtgatt ttggatgagt cattagtact gatcgtactt gctgacctct   146880
aaaatttaca atgctttgca ccggagctgt aattaaaact tggttaactc caggttttcc   146940
tccaatgtct tggagaacga tagtatctcc atcaattggg gaagatggta agtaaatgt   147000 aatgtcatta ccagctgcag tatcaactga aattgattcg cctgacttta attgataagg   147060
tcctgatgaa acagttgtcc aattagcatc agtacgtaat gatctccaac gtacgctatt   147120
aaaagctcct gctggttttg gaatatcatt tatagcagcc caaaagcggt tatcataaat   147180
gattacaaaa tcttttaaat atccacgagt tggatcatat tgttgaactg tgttttcttg   147240
aattaagtaa tcaacgttga caccgtcagt tcctacggta cgatcagcta aagctacgtt   147300
gattatttta tcgccacctg cgtccagacc gtcttctgct ctgaactttc ttttaatctc   147360
ggccattctc ccgggctcct aatgtgtttt caataataag tatttatact tgtttacttt   147420
aagatttgga tagtatataa tagaaatctc actaattgaa cgaggttcat atggatttag   147480
aaatgatgct ggatgaagat tacaaagaag gaatttgctt aattgacttt agtcaaattg   147540
cgctttcaac tgctttggta aactttccag ataaagaaaa aattaattta tcaatggttc   147600
gtcatttgat attgaactca attaagttta atgtcaaaaa agcaaaaact cttggataca   147660
ctaaaattgt actgtgtatt gataacgcga atctggata ctggcgtcgt gattttgctt   147720
attattataa gaaaaaccgt ggaaaagcac gagaagaatc tacttgggat tgggaaggtt   147780
attttgaatc cagtcataaa gttatagatg aactgaaagc ttatatgcca tacatcgtta   147840
tggatattga taagtatgaa gcagatgacc atattgctat tcttgttaaa aagttctctt   147900
tagaaggaca taagatttta atcatttcat cggatggtga ctttactcaa cttcataaat   147960
acccaaatgt taagcaatgg tcaccgatgc acaagaaatg ggtaaaatt aaaagcggtt   148020 ctgctgaaat tgactgtatg actaaaatcc ttaaggtgaa caaaaggat aacgttgctt   148080 cagttaaagt acgatctgac ttttggttta ctagagttga aggtgaacga actccttcaa   148140
tgaaaacctc tattgttgaa gctattgcta atgaccgtga gcaagctaag gtgcttctta   148200
ccgaatctga atataatcgt tataaagaaa atttagttct aattgatttt gattatattc   148260
ctgataatat tgcttcaaac attgtgaatt actataattc atataaatta ccaccgcgtg   148320
gcaaaattta ttcatatttt gtaaaagcgg gtctttctaa attaactaat agcattaatg   148380
```

```
aattttgagg tgaataatgg ctaaaaaaga aatggttgaa tttgatgaag ctatccatgg   148440
cgaagatttg gctaaattta ttaaagaagc atctgatcat aaactgaaaa tttctggtta   148500
taatgaattg attaaagata ttcgaattcg tgccaaagat gaacttggcg ttgatggtaa   148560
gatgtttaat cgtctgttag ctttgtatca taaagataac cgtgatgtgt ttgaagctga   148620
aactgaagag gtagttgaac tttatgacac agttttctct aaatgatatt cgtccggtcg   148680
atgagaccgg tctttcagaa aaagaacttt caattaagaa agaaaaagat gaaattgcaa   148740
agcttcttga ccgtcaagaa aatggattta ttattgaaaa aatggtagaa gagtttggaa   148800
tgagttatct tgaagctaca acagcattct tggaagaaaa ttctattcct gaaactcaat   148860
ttgctaaatt tattccttcg ggtataattg aaaaaattca gtcagaagct attgacgaaa   148920
atcttttacg tccttctgtt gttcgttgtg aaaaaactaa tacattagat tttctactat   148980
gattaaactc cgcatgcctg ctggtggtga agatatatt gatggtaaat cagtttataa   149040
attatactta atgataaaac aacatatgaa tggaaagtat gatgtaatta agtataattg   149100
gtgcatgcgg gtgtctgatg ccgcttatca aaagcgaagg gataagtatt ttttccagaa   149160
gttatcagaa aaatataaat taaggaact tgctttaatc tttataagca atcttgttgc   149220
taaccaggat gcttggattg gtgacatctc tgacgctgat gcacttgtgt tttatcgtga   149280
atatatcgga cgcttaaagc aaattaaatt taagtttgaa gaagatattc gcaatattta   149340
ctatttcagt aaaaaagttg aagttctctgc ttttaaagaa attttgaat ataatccaaa   149400 agttcaatca agttatattt ttaaactact tcaatcgaat ataatttcgt ttgagacgtt   149460
tatcttgctt gattcgtttt taaatataat cgataaacat gatgaacaga ctgataattt   149520
agtctggaat aattattcta taaagttaaa ggcttataga aaaattttaa atattgattc   149580
acagaaagct aaaagtgttt tcattgaaac tgtgaaatct tgtaagtatt gatatgaata   149640
tagtatattg gtttacattt gaagaccgtg tcaaaaataa gactccgccg tactactata   149700
tcggcagtaa attaaattgc tcatttgaga atggaataat atatgactct tccggaaagg   149760
aatactggag ttcgtgtaaa caaaaaagat ttttaaatgc ggtaatgctt caaaaaccga   149820
gcgttaaaat aattcaaatt gatgatgatt tggatgttat tgaagcagag cgaaaatacc   149880
aacttgaagt aaatgccaga gataatccag actattttaa tctggtatat gctggcggcg   149940 ggttggtgt gagtggtgaa actcatccag ccaaagaccc ggaagttaga gagcatatga   150000
gattggctaa ttatatgaac cgtgacgatt ttagaccttg gaaaacatca cgagctaata   150060
tagagtcttg gaaattatct catattgctt acgagaatta tgtgttatta ttatcctcta   150120
atctgtacgg taaaactcct ggatggcgaa gagttaaagg taatataaat ataactgatg   150180
caactgctaa atcgatggta aagtatttca actcaggttg gatacctctc gaagacccag   150240
agtattgcga attatgccag ctatgaggta aagtgtcata gcaccaactg ttaattaaat   150300 taaaaggaa ataaaaatgt ttaaacgtaa atctactgct gaactcgctg cacaaatggc   150360
taaactggct ggaaataaag gtggttttc ttctgaagat aaaggcgagt ggaaactgaa   150420
actcgacaat gcgggtaacg gtcaagcagt aattcgtttt cttccgtcta aaaatgatga   150480
acaagcacca ttcgcacttc ttgtaaatca cggtttcaag aaaaatggta atggtatat   150540 cgaaacatgc tcatctacct acggtgatta cgattcttgt ccagtatgtc agtacatcag   150600
taaaaatgat ttgtataaca ctgacaataa agagtacggt cttgttaaac gtaaaacttc   150660
ttactgggct aacattcttg ttgtaaaaga cccagctgct ccagaaaatg aaggtaaagt   150720
atttaaatac cgtttcggta agaaaatctg ggataaaatc aatgcaatga ttgcagttga   150780
```

```
tgttgaaatg ggtgaaactc cggttgatgt aacttgtccg tgggaaggtg ctaactttgt    150840
actgaaagtt aaacaagttt ctggttttag taactacgat gaatctaaat tcctgaatca    150900
atctgcgatt ccaaacattg acgatgaatc tttccagaaa gaactgttcg aacaaatggt    150960
tgacctttct gaaatgactt ctaaagataa attcaaatcg tttgaagaac tgagcactaa    151020
gttcagtcaa gttatgggaa ctgctgctat gggtggtgcc gcagcaactg ccgctaagaa    151080
agctgataaa gttgctgatg atttggatgc attcaatgtt gatgacttca aaacaaaaac    151140
tgaagatgat tttatgagct caagctctgg cagttcatct agtgctgatg acacggacct    151200
ggatgacctt ttgaatgacc tttaacagat tatattacta attaattggg gaccctagag    151260 gtccccttttt tttatttcaa aaattttttc acaaagctgt ttacatcctt gtccttccat    151320
ggtactatac aactatcggc aatactgctg atgattaaag aggaaaataa tatggctaaa    151380
gttgatattg acatcgttga ttttgaatat attgaagaga ttattcgtaa tcgttatcct    151440
gaacttagta tcacaagcgt gcaagattct aagttttgga gtattcaaat cgttattaaa    151500
ggtcctcttg aagacctcac cctctttatg gctaatgaat attgtgatga catgggttct    151560
gaagacgcag aattttacat gggattgatt gaacaataat tatcaagggg ctatcaagcc    151620
cctattaaaa tgaggaaaat caaaaatgga atcggcaaa aaatatgagt taaatccaca    151680
ccgtattaaa tctttcattg atattagttc atcaaatgct agtatggtcg gcatcattca    151740
agaaaatggc ggttggtttg aagttaaatc aatatcaagt ttagatggat ttgattatgt    151800
aaccgaaatc atttgcgcca atggtgaaat ctataatgat gatggtatgg gtgatgatta    151860
ttttgaactt agtgaagaag agtttttattg ttttcgcgag tataaagaac caactttga    151920 agaagatgaa gtcgaagaca ggatttctgg cgtaacaaaa attcactgca ttgtagatga    151980
aaacaatgta gatgaaatca ttgaactttt gcgaaaaact ttcaaaaagt agtttacaga    152040
agggtagtag cgtgatacta ttaccctatc aattaaggag aataaaatga gattacaacg    152100
ccagagcatc aaagattcag aagttagagg taaatggtat tttaatatca tcggtaaaga    152160
ttctgaactt gttgaaaaag ctgaacatct tttacgtgat atgggatggg aagatgaatg    152220
cgatggatgt cctctttatg aagacggaga aagcgcagga ttctggatt accattctga    152280 cgtcgagcag tttaaagctg attggaaaat tgtgaaaaag tctgtttaag gaaaataata    152340
tgatttttgt atttgaattt atgaatgatg aattcgatta tgcaattttt aacgcattgc    152400
ataatcctga tttaagtgaa tttaatgaaa tgttttctga cgctttgagt atgtcagaag    152460
aatactgtga agaatgtcaa cgtgtttgtg tgacagtttt tgaaaacaaa gaaagagcat    152520
atgaagaatt attctttgac gctaataaag ccactgaatg gtttattgaa aggggctttg    152580
cgtaatgatt aaattggtat tcgcttattc tccaactaaa accgttgaag ctttaatga    152640 attagcattc ggtttaggtg atggtttacc atggggacga gttaaaaagg acctccagaa    152700
ttttaaagct cgtactgaag gtacaattat gattatgggt gctaaaacgt tccagtcatt    152760
atctacatta cttcctggac gtagccatat tgtggtgtgt gaccttgcgc gtgattatcc    152820
tgtaactaaa gacggcgatt tagcacattt ctatattact tgggaacagt atataactta    152880
catttctggc ggtgaaattc aagtgtcaag ccctaatgca ccattcgagg ctatgcttga    152940
ccagaattct aaagtaagtg taattggcgg acccgctctg ttatatgctg cattaccttta    153000 tgcagatgaa gtagttgttt ctcgtattgt taaaaggcat cgtgttaatt caactgttca    153060
attagatgca agttttcttg atgatataag caagcgtgaa atggttgaaa cgcattggta    153120
```

```
taaaatagat gaagtaacaa cccttacgga atcagtatat aaatgaaata acgcgtggca    153180
gaaaatatga attttaatta ttaccctatt ttattagaaa aagacgcgaa acagccaaag    153240
tggcagggtc ctcagtttat aaaggtgtc tatcaattag tagttcctaa agacaagatt    153300
tatagcagtt gtttcactga atccgcttgc agtattttcg gtaatagttc tccgtattgg    153360
aattttgaca taaagctgga tagaaatatc gatatttggt tgaaagctat ggatattggt    153420
aatatcacgt ttgatgagaa taattatcat attattggtc gcttttccaa acgcggtaaa    153480
gaattatatt tcacgcctga aattgagaga aaatttgatg ctaaaccgta ttgattattt    153540
agcttcataa aatgtattat aatttatata aggtactaaa tgaaacaata ccaagattta    153600
attaaagaca ttttttgaaaa tggctatgaa accgatgacc gaacaggcac aggaacaatt    153660
gctttgttcg gtactaaatt gcgctgggat ttaaccaaag gttttcctgc agtaacaact    153720
aaaaagctcg cctggaatgc atgcattgct gagctaatat ggttttatc aggaagcaca    153780 aatgtcaatg atttgcgatt aattcaacat gattcattaa ttcaaggcaa acagtctgg    153840 gatgaaaatt acgaaaatca agcaaaagat ttaggatacc atagcggtga acttggtcca    153900
atttatggaa aacagtggcg tgattttggc ggtgtagacc aaattataga agttattgat    153960
cgtattaaaa aactgccaaa tgataggcgt caaattgttt ctgcatggaa tccagctgaa    154020
ctcaagcaga tggcattacc gccttgtcat atgttctatc aatttaatgt gcgtaatggc    154080
tatttggatt tacagtggta tcaaagaagt gttgacgtgt tcttgggctt gccattcaac    154140
attgcatcat atgctgcgtt agttcatatt gtagctaaga tgtgtaatct tattccggga    154200
gatttgatat tttccggtgg taatactcat atctatatga atcacgtaga acaatgtaaa    154260
gaaattttac gtcgtgaacc tatggattta tgcgaattgc aattaaaatt tccagatgaa    154320
tttgatgaat gggacacaga atcgcaggta ttttggttga gtcaattcgc aaagccgcat    154380
aattttgttc ttaacaacta tgaatcacac cctcctatta aggaaagat ggcggtgtaa    154440 ttttaattta attgcgagga tatatgattt tacgatttaa agatacttct ggtgtagttc    154500
tttttacact tcctaatcca agtgagttag aagttccagg accaaatcag cctattatca    154560 tttatgcaa aaaatattat actcataaaa tgactcgtga gtattttgat aataaaattt    154620
ctacagttaa aacttcttct gactgttact acgatattac tgttttaacg gaagaacaat    154680
atgaacacct acaaccgcgc gggccgtcta tgccgggtag tgaataaata taaatccgac    154740
tttgatgtta atattcaccg tggtacattt tgggggaatt acgtcggtaa agatgctggc    154800
agccgggagg ctgccattga attattcaaa aaagatttta tacgtcgaat taaatccgga    154860
gaaataacta aagcacattt agagccttta cgtggaatga ggctaggatg cacatgtaaa    154920
ccaaagccgt gtcatggtga tataatagct catatagtta accgattgtt taagacgat    154980 tttcaagttg aggacttatg caattaatta atgttatcaa aagtagtggt gtttctcaga    155040
gctttgaccc acaaaaaatt attaaagttt tatcttgggc agctgaagga acatcagtag    155100
atccttatga attatatgaa aatattaaat cttatctccg tgatggaatg acaactgatg    155160
atattcagac tattgtcatt aaggctgctg cgaattctat ttcggttgaa gagcctgatt    155220
atcaatatgt agctgcacgc tgtttaatgt ttgctcttcg taagcatgtt tatgggcagt    155280
atgaaccacg ttcatttatt gaccatattt cttattgtgt aaatgaaggt aaatatgacc    155340
ctggattatt gtcaaaatat tcagcagaag aaattacatt tttagaatca aaattaagc    155400 acgaacggga tatggaattt acttattccg gggcgatgca attaaaagaa aaatatctag    155460
ttaaagataa aaccactggt caaatttatg aaactccaca gtttgcattt atgactattg    155520
```

-continued

```
gaatggcact gcatcaagat gaacctgttg acagattaaa acatgttatt cgttttatg    155580 aagcagtatc tactcgacag atttcattgc caactcctat tatggctggt tgtcgtactc    155640
caactcggca gtttagttca tgcgttgtta ttgaggcagg tgattcgctg aagtctatca    155700
ataaggcttc cgcttcaatt gttgagtata tttctaaacg cgctggaatt ggtattaacg    155760
ttggtatgat tcgtgccgaa ggttctaaga ttggcacagg tgaagtgcgt catactggtg    155820
ttattccttt ttggaaacat tttcagactg ctgttaaatc atgctcacag ggtggaattc    155880
gtggcggcgc tgctactgct tattatccta tttggcattt ggaagttgaa atcttctcg    155940 tttttgaaaaa taacaaaggt gtagaagaaa accgtatccg tcatatggat tatggcgttc    156000
aactgaatga tttgatgatg gaacgttttg gaaagaacga ctacattact ttgttcagtc    156060
cacacgaaat gggtggcgag ctttattatt cttatttaa agaccaagac cgtttccgtg    156120
aattgtatga agccgcagaa aaagacccta atattcgcaa aaagcgtatt aaagcacgtg    156180
aactgtttga attgctcatg actgaacgat caggaacagc aaggatttat gtacagttca    156240
ttgataatac gaataactat actccattta ttcgtgaaaa ggcacctatt cgtcagagta    156300
acttgtgctg tgaaattgct attccaacaa atgatgtgaa tagtcctgat gctgaaattg    156360
gattgtgcac gttatctgca tttgtgttgg ataacttcga ttggcaagac caagataaaa    156420
ttaatgaatt ggcagaagtc caagttcgtg ctcttgataa tcttttggat taccaaggat    156480
atccagttcc tgaagcagaa aaagctaaaa agcgtcgtaa ccttggtgta ggtgttacta    156540
actatgcagc ttggctggca agtaactttg cttcttatga agatgctaac gatttaacac    156600
atgaactatt tgagagatta cagtatggac tcattaaagc atccattaag ctcgccaaag    156660
aaaaaggacc ttgcgaatat tattcagaca ctcgttggtc tcgaggcgaa ttacctatcg    156720
actggtacaa taaaaagatt gaccaaatcg cagctccaaa atacgtttgt gactggtcgt    156780
cgctgcggga agaccttaag ctcttttggca tccgtaatag cacattatca gcacttatgc    156840
catgtgagtc atcttcccaa gtttctaaca gtacaaatgg tatcgagcct ccacgtggac    156900
cagtctctgt taaagaatca aaagaggggt cctttaatca agtcgtgccc aatattgagc    156960
ataacataga cctatatgat tatacgtgga aattagctaa gaaaggtaat aaaccttatc    157020
ttacgcaagt agctattatg cttaaatggg tatgtcaatc agcttcagct aatacatatt    157080
atgacccgca gattttttcca aaaggaaagg ttccaatgtc aataatgatt gatgacctttt    157140 tgtattttg gtattttggc ggaaaaaatt tctattatca taatacccgt gacggttctg    157200
gtactgatga ttatgaaata gaaactccaa aagctgaaga ttgttcatcc tgtaaattat    157260
gatataattt gactcacgga cgagtcacta tctattaact aagcggaaaa tttatgagca    157320
cagtttttaa tacaaatcca gttgatgttt taaagaacc tatgttcttc ggttcaggtc    157380
ttggtattgc gcgttatgat attcaacgtc ataaagtttt tgaagattta accgaaaagc    157440
aattatcatt tttctggcgt cctgaagaag taaacttgat gatggatgct gcacaattta    157500
acaagcttcc tcaatatcag caagatattt ttactaataa cctgaagtat caatcacttc    157560
tagatagcat tcagggtcgt gcaccatctg ctgtacttat gtcgttaatt tcagaccca    157620 gccttgatac atgggttgct acatggactt ttagtgaaac tattcacagt cgttcataca    157680
ctcatatcat gcgaaatctt tatactgatc catcaaaggt atttgatgag attgtattag    157740
ataaagctat tatgaaacgt gccgagtcca ttggtcgcta ttacgatgat gttctagtta    157800
agactcgtga atatcagaat gcggttgaag attatgaagg aatttttatca gaaggatttc    157860
```

```
ataaagaaga gctaggcaaa gttgttgaat atactaaacg ggcactaatg aaatctcttt   157920
atctttgcct tcatgtaatc aacgcattgg aagctattcg ttttttatgta tctttcgcat   157980
gtacctttaa cttccataaa aacatggaaa tcatggaagg taatgccaag attatgaagt   158040
tcattgctcg tgatgaacag cttcacctta aaggtaccca atatattatt cgtcaacttc   158100
aacttggcac tgatggtgat gaatgggtta aaatcgccca agagtgtgaa caagaagcag   158160
ttgatatttt tatggaagtc aaccgccaag aaaaagactg ggcagttcat ttatttaaag   158220
atggcgatgt tcctggatta aatacaaata gcatgtggag ctttattgat tacttaactg   158280
tatctcgtat gaaacagtgc ggtcttccat gcccaattac cgtagctccg gttaaacacc   158340
cgtatccttg gattcgtgaa tatcttaatt ctgataatgt tcaatccgcg ccacaagaag   158400
tagaactgtc atcttatctt gtagcacaga ttgataatga tgttgatgat aaagttatga   158460
tgagttttaa aaaatatttt taaggagtgg gccgcaaggc ccatttttatt atgaaagaaa   158520
ttgcaacaga atattcattt attaaatata ctgagctaga attagacgac aacggaagta   158580
taaaacaatt atccattcca aacaagtata acgtaattta tgctattgct ataaatgatg   158640
agcttgttta tattggaaaa actaaaaatt tacgtaaaag aataaattat tatagaactg   158700
ctattaatcg taaagacaaa acgtctgatt ctactaaatc tgcattaatt catgctcgc    158760
taaaggaagg aagcaaagtt gaattttacg cccgccaatg ttttaatctt tctatgacaa   158820
atgagttagg tacaatgaca atcgcaacga ttgacctaga ggagccgcta ttcattaaac   158880
tgtttaaccc gccttggaat attcaacaca agaaaaaatg atgcttccac atggagtgtg   158940
gtactatatt caaaacacaa aagaggatac acaatgcaag aacttttaa caatttaatg   159000
gaactatgta aggattcaca gcgtaagttt ttttactcag atgatgtaag tgcatctgga   159060
agaacttaca gaattttctc atataattat gcatcttatt ctgattggtt acttccagac   159120
gcattagaat gtcgtggaat tatgtttgaa atggatggag aaaaaccggt aagaatcgct   159180
tctcgtccta tggaaaagtt ttttaacttg aatgaaaatc cattcacgat gaatatcgat   159240
ttaaatgacg tcgattacat tctaacaaaa gaagacgggt cttttggtatc aacttattta   159300
gacggtgatg aaattctgtt caaatcaaag ggttcaatca aatctgagca ggctttaatg   159360
gctaatggaa ttttgatgaa tattaatcat caccagttgc gcgacagact taaaaaatta   159420
gccgaagatg gatttactgc taactttgaa ttcgttgctc cgacgaatag aatcgttctt   159480
gcttatcaag agatgaaaat cattttattg aatattcgtg aaaatgaaac aggcgaatac   159540
atttcatatg atgatattta taagatgct attcttcgtc catatctagt tgaacgatac   159600
gaaatcgata gtcctaaatg ggtagaagaa gctaaaaatg cagaaaacat cgaaggctat   159660
gttgccgtga tgaaagatgg ttctcatttt aaaattaagt ctgactggta cgtgtctctt   159720
cacagcacaa aaagttcatt agataatcca gaaaaattgt ttaagactat tattgatggt   159780
gcatcagatg atcttaaagc aatgtacgct gacgatgaat attcatatag aaaaattgaa   159840
gcatttgaaa cgacttatct gaagtactta gaccgagctc tgttttttagt tcttgactgt   159900
cacaataagc attgcggcaa agatagaaag acttatgcaa tggaagcgca aggcgttgct   159960
aaaggtgctg gaatgaaca tctgttcggt atcatcatga gcctctacca agggtatgat   160020
agtcaagaga aggtcatgtg tgaaatcgaa cagaattttt tgaaaaatta taaaaattt    160080
atcccagaag gatactaagc tgtttacaag tccctcgtgt tgtgttatag tagtcttact   160140
gacataacat gaggacttta tgatggattt gcagcttatt actactgaga tggtcgttga   160200
agcatacggt gatactacag atgggatttc tgtatttaaa ggaaatcgtc gagttggata   160260
```

```
tatcaccgat cttaagaaag atttagctaa gcaagtcaag cggaaaacga ccattaaaga   160320
atatcgaaat cgtcgtcttg agcaagcccg tgatatgctt cctgatgcgg ttgaggagat   160380
gaaagtcttt ttagaaaatc agcttgcgaa atatgattgt gatgtgttca ttaatcagac   160440
tcaacctaat gttcatatta acaactgtaa atgctatatc atcgttaatc ctttaacggg   160500
aaaacatcgt cttggaatta gtaatccaaa tcgtagtgca tcggatatgg cagaagatgt   160560
tgaggcatgc tttaaaattt ctaaatctcc ggctgaacat catattttaa ttaacggtct   160620
ttctcaagac gatattatag aggttattaa aactttatgc aattaagtaa tacgacaaca   160680
ggcttgctat taattgtaat tgcattgggc ggaacttctt taattttaaa aaataaaatt   160740
gaaagattag aaacgtctgt tgtagaaatt acaaaaacgg ccaatgaaaa cgctttagca   160800
ttaaataatt tgcgaattca gtataattat attgatgcga tgaataataa aaatcgtgag   160860
gcaattgctg ctattgagcg tgaaaatgaa aaactgcgca agacgcaaa gaaggcggat    160920 gtggtggctc ataagccagg attggttgaa aaacaaatca acaactcctt caacaagttc   160980
gcagaagaca tccaggacct ttctaaatga ttaaactatc agcagtaata ttatctattg   161040
gtcttctagt tggttgttcg acaaagcctc tagaagtaaa gaaagaaaca gttcatccta   161100
attggccagt acaaataaag tcatacgatg aagctaaact atcctggcaa gttaaagtta   161160
ttgatggtaa agcttgggtc ggtatgccat tcgaagattc ccaggaattt cgtatttggc   161220
ttaatgatgt aaaacgatat gtacatgatc agaaaactat gatatgttat tatcgccaag   161280
agttaaaaga ggataaatgc aaatgatttc atggcatcaa tttgaacatc tcaaaggatt   161340
gatttatgaa tccgagatgg ctgcaatgat ttacggacgc cagattcagc ggttagaatc   161400
tttacctcca actaatgatg ttttattagc tcaatctcgt gctaatctta aaaatgaata   161460
ccaaaataag tggggtaaag catctaaaga cctgcatgat tatattcaat cattggttga   161520
gaaataataa atgaaaactc tgttagaacg ttatattgaa tgttcagacc gttacattga   161580
tgcatgccgc ggtgcagtat atatggattt ggaccgcggg gtagtattaa atgatgaaga   161640
ccctgcgaaa gctttagatg atgcaggtaa agcattacga aaagaagcaa aagcccgtgg   161700
gcttgatatg tatcagctta aaaatcacat gataaaattt atttcatcca atgttcagag   161760
caaatcggtg aatcaatcaa cagctgaatt gtataaagga cggcgtgagc ataatattcg   161820
tattcttgaa gttttcttag gaattaaatg atgaaaaaga ttattttgac tgttggatgt   161880
cctggttcag gtaagagcac ttgggctcgt gaatttattg ctaaaaatcc tggattttat   161940
aatatcaatc gtgatgatta tcgtcaatcc atcatgggcc atgaagaacg cgacgagtat   162000
aagtatacca aaaagaaaga aggtatcgta actggtatgc agtttgatac agctaaaagt   162060
attctgtacg gtggcgattc tgttaaggga gtaatcattt cagatactaa cctgaatccc   162120
gaacgacgac tagcatggga aactttttgcc aaagaatacg gctggaaagt tgaatataaa   162180
gtgtttgatg ttccttggac tgaattggtt aaacgtaact caaaacgtgg aactaaagca   162240
gtaccaattg atattttacg ttcaatgtat aaaagcatgc gagagtatct cggtcttccg   162300
gtatataaag ggactcctgg taaaccaaaa gcagttattt ttgatgttga tgcacatta    162360 gcaaaaatga atggtcgcgg tccttatgac cttgaaaaat gtgatactga tgttatcaat   162420
cctatgattg ttgaactagc taagatgtac gataagcaag gatattacat tgtagtcgtt   162480
tcaggccgtg aaagtggaac cgaagaagac ccaacgaaat attatcgtat gacccgtaaa   162540
tgggttgagg atattgctgg cgttccatta gttatgcaat gtcaacgcga acaaggtgat   162600
```

```
acccgtaaag atgatgtagt taaagaagaa attttctgga aacacatcgc accgcatttt 162660
gatgtgaaat tagctattga tgaccgtaac caagtcgttg agatgtggcg tcgtatcggt 162720
gttgaatgct ggcaagttgc ttatggagat ttttaatggc gtggcatcat gaaacttggt 162780
ctattgttat tgtaaatagt ggtttagttg gtactagtaa tgggcaattt tgtgtattca 162840
ctagtgaaat cagagcttgg gaggaatgtc ttaaattaag agaaagaat cctgatgttg 162900
aactaacagt aaagaaaact aaactgcctt taccatggaa aacttatgaa taacatagaa 162960
aagatttatc aactttgcga taaaattgaa aaagaaaaga aatatctatt ttgtttatgg 163020
cctattgttg atggaagaat agacttagat attcttgatt atgaaacaga agacatagta 163080
gatggttcaa cttttgataa tgcgttggat gttattaatt ggcttgaaga aaattatgtg 163140
gggtgaatat gtttccgact tattctaaaa tcgtagaagt agtgtttagt caaattatcg 163200
ctaataatat gtttgaaaag cttgataacg cagccgagct tcgaattcat gctcaagtga 163260
ctcatgtatt gaacactttg cttccagacc aggtggattc tattgcaatt acgctgtatc 163320
cgggttccgc gcatatcatt gtcgtatttg gtcttgatgc tgagctagtt atcaaaggcg 163380
atattcgttt tgaatcgcag acatcagaat tcaaagcaat ttaatagttt actttacggt 163440
agagttgtga tattatagct ctaccaaaac aaatgaggaa attgaaatga gcgaatggtt 163500
tgaagaagat aaggtttatc gctttaaagc tggatataaa gatattttta atgaaacttg 163560
tggggctaat aaacgaattg ctcagtttat tggggaaaat tcatttaaag taaaaataga 163620
tcctgcgaaa aatgttatta gcattaaacg cgaaattgac gattgctggt ataaagctgt 163680
tgatgtaatg ggcgaatcct ataaagttag cccgttattt tcaattgctt atatgttaga 163740
atattctttt ttcgaagaag ttcaaaaaga tgattctgtc agtaaatttg aaattaaaac 163800
tgataaagaa attaagtgga agtagtagg tattactggt tgcatgtttt atatctatgc 163860
tcaaactgat acgaaggaag aagctaaaaa gaaagctcta gaatatcttg aagagtataa 163920
agaaggcccg gtaatgatta cccaagatgc cgaattagtt tctgtcaaat tagttaaaaa 163980
cgttgaaagt aaggagctgg gatcaacatg ctaagtgaaa aaccaattac tgttaaagaa 164040
ttccaagaaa aagttaaact atttgctcag gaattggtaa ataaggtttc tgaacgattt 164100
cctgaaacat cggttcgtgt tattaccgaa actcctcgtt cagtattagt aattgtgaat 164160
ccaggtgatg gtgatcaaat aacacatctt aaactggatt ttgatggatt agttgaagca 164220
caaagggtgt atggcgtact atgatgaatt taactgatat aattgataat tgtcttgaaa 164280
atgatactgg cgatcataga gcgcttgatt ctgaaacagc acagttcatt agaataactt 164340
taatgaatga tactctagtg aatagtattc atccttctgt gtatgatgct attattgtga 164400
cgaagtatcc agttgagctt cacaaaaaga tggttggtgc aattttttatt gataagaaaa 164460
accgctttaa agatgggcag aatataatta gttctgttat taaaagtata actaaacttc 164520
gtcacgaaat ttatcgtgtt gaaactgcta atctgcttta tctggtgatt atgaaatgaa 164580
agcgagtaca gtacttcaaa ttgcatattt agtatcacaa gaatcaaaat gttgctcctg 164640
gaaggtagga gcagtaattg aaaagaatgg acgtattatt tctactggat ataatggttc 164700
acctgcaggt ggtgtgaact gctgtgatta tgctgctgag caaggttggt tgctgaataa 164760
gcctaaacat actatcattc aaggtcataa gcctgaatgc gtatcgtttg gttcaactga 164820
tcgttttgtc ttggcgaaag aacaccgtag cgctcactct gaatggtcgt ctaaaaatga 164880
aattcatgct gaactaaatg cgattttgtt tgctgcacga aacggttctt caattgaagg 164940
tgctactatg tatgtaacac tttctccttg tccggattgt gcaaaagcga tagctcaatc 165000
```

```
tggaattaaa aagctggttt attgcgaaac atacgataaa aataaacctg gctgggatga   165060
tattctgcga aatgcgggta ttgaagtgtt taatgttcct aagaaaaact tgaataagtt   165120
aaactgggaa aacatcaacg aattctgtgg tgaataatga aatttcgttt ggtacagctc   165180
acagcaatta gttcttattc taacgagaac atttcatttg ctgtagagta taagaagtat   165240
tttttctcta aatggaaaca gtattataag tcagaatggg tttgtattga tagaccgtat   165300
agttggaaat ctgatttaga aaaatgccaa aaattgcttt ccactcttaa agaacgtgga   165360
acaacccata ttaaaactgt agtaggtaaa taaatgaaac tgacaactga acagaaagta   165420
gcaattcgtg aaattttgaa aactaaattg tccatggggg tttcaaacgt agttttgaa   165480
aagtctgatg gtactattcg tactatgaaa ggcactcgtg atgcggactt tatgccaacc   165540
atgcaaactg gtaaattgac tgaatctgct cggaaagaat ctactgatat gattccagta   165600
tttgatgttg agcttggtgc atggcgaggt ttttctattg acaaattgat ttccgttaat   165660
ggtatgaaag ttgagcattt gcttcaattt attggtaaat aaatgcttta agaattattt   165720
gttattatta attcatctgt taacaaaaag gaaaaacgat gtctgaagta caacagctac   165780
caattcgtgc tgtcggtgaa tatgttattt tagtttctga acctgcacaa gccggtgatg   165840
aagaagttac agaatcagga cttattatcg gtaaacgtgt tcaaggtgaa gttcctgaac   165900
tgtgtgtagt tcactctgtt ggtcctgatg ttcctgaagg tttctgtgaa gttggtgatt   165960
tgacttctct tccagttggt caaattcgaa acgttccaca ccctttttgta gctctgggtc   166020
ttaagcagcc aaaagaaatt aaacaaaaat tcgttacctg tcactataaa gctattccgt   166080
gtctttataa gtgatataaa taataatatg aattgagttt caattctatg tggtagtcta   166140
caactgagag atctgtcgaa agaagatgaa attcagaaga acgtgactac cgagttttaa   166200
tctctaacga gaattttttaa atgattaaac aattacaaca cgctcttgaa ctgcaacgaa   166260
acgcatggaa taatggtcac gaaaactatg gcgcatctat tgatgttgaa gccgaagctc   166320
ttgaaatcct gcgttatttc aaacatctga atcctgctca aactgcatta gctgctgagc   166380
ttcaggaaaa agatgaactt aaatatgcta agccactggc ttctgctgca cgaaaagcag   166440
ttcgtcactt tgtggtaaca ctgaagtaag tatgatgacg ggtttatggt tatcctggtc   166500
gttaaatatt caaaaaccta tgttcccctt gagggcttgc gcaggcaatg ccaataagtc   166560
ctgcattttc atttaaaaga gaatttataa tggcaaaaca agctaaagca aagaaagcag   166620
ttgaaaagaa agttggtgat tctaaacgcg ctggctacaa gcgtgggtcg aactctcgta   166680
tcaatcaaac tgttgagaag atcatgcgcc gagcacgtgc ggttcttcga gatgatgctt   166740
ctcgttttgg taagcagaaa gcataagttg aggactcctt cgggagtcct ttttatttt    166800
ccaaagattg cacaaagttg tttacagtat ggttcctttg tgatagtatt atcttacaca   166860
aacaaggag aataaaatga aacaattaa tctgaacgct gcagttaaaa ctaaatgctt     166920
caacggtaaa tatgatgaaa ctatgtggtt cttaatggca gttgaaggtg atattattga   166980
agtagaaaca acagaaggta tgggaacaga tttcacccttt acaattcaag ttcataattt   167040
ctttactggt tggatttatg aattgaacac agtaatcgtt ggaaaaattg aacaaaatga   167100
attgggtgaa tggtattatg ttacagctcg ccaacgtgcc gaacgcttaa ttgagaagat   167160
gaaaaaagtt ggtaaacttg acatgcagca ctggaaagta gtaaataat tgtttacttt    167220
ggtacaggat atgatattat ataccctgtac cgcaattaaa catcttggag aataaaaatg   167280
aactacatca actttgaacg taaatatgtt tctaatggta ttgcaggttc tattgatact   167340
```

```
atttgccttt ggaaacatca aaatggatca gtatgcgaaa ttgaacagta tatgacccct  167400
aactacgttt atatgcgatt tgaaaatggc atcacggttt caatcacaat ggaaggttcc  167460
aacttcaaaa tcgctctgga tgatgatttt cgtcaacgcg atttagggac tcatccttgc  167520
tggaatggtg ttaatcgcaa gcttctggtt aaaacttgga ttcgtcatat tctgagtaac  167580
agagctaaac ctgagcatct tgaagcaatc tttgatgtag ttcttaacga atttgatatt  167640
taaaataaaa caggggcttc ggcccttac tgaggaaaat actatgttta tgactactta  167700
ttttgatacc cgcaaaaatt tctgtgaagt ggttttctct aaggcgccta aagaccttcc  167760
tgctcatttg caacctacca gcgaatcgat taaaaactac gttaatgtag tctgtccttt  167820
agagttccgt acagtaaatg ggcgcgatac tttagctatc gctaaactca atcgtgaaat  167880
tgacattgac ccttcaattg cgcgtgaaat taatatttct gatattggcg gcggtaatgt  167940
taaatcgcat ggttttcaga tgaggttcta atgaaattct ttttaggtca aactgttgaa  168000
ttaaagggag ttggtatacc tggattaatt tctaaggttt tacctccatt taaatggagt  168060
ggtgttcaaa taaagaggc ttatattgtt tcttgggtag atggaaatga agaccttcgt  168120
atgggtgatg aattatctcc tatttacgga ttaaaggaat t                      168161
```